United States Patent
Manipatruni et al.

(10) Patent No.: US 12,147,941 B2
(45) Date of Patent: *Nov. 19, 2024

(54) ITERATIVE MONETIZATION OF PRECURSOR IN PROCESS DEVELOPMENT OF NON-LINEAR POLAR MATERIAL AND DEVICES

(71) Applicant: Kepler Computing Inc., San Francisco, CA (US)

(72) Inventors: Sasikanth Manipatruni, Portland, OR (US); Niloy Mukherjee, San Ramon, CA (US); Noriyuki Sato, Palo Alto, CA (US); Tanay Gosavi, Portland, OR (US); Somilkumar J. Rathi, San Jose, CA (US); James David Clarkson, El Sobrante, CA (US); Rajeev Kumar Dokania, Beaverton, OR (US); Debo Olaosebikan, San Francisco, CA (US); Amrita Mathuriya, Portland, OR (US)

(73) Assignee: Kepler Computing Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,545

(22) Filed: Jul. 25, 2023

(65) Prior Publication Data
US 2024/0211872 A1  Jun. 27, 2024

Related U.S. Application Data

(63) Continuation of application No. 18/088,413, filed on Dec. 23, 2022, now Pat. No. 11,741,428.

(51) Int. Cl.
*G06Q 10/087* (2023.01)
*G06Q 30/04* (2012.01)
*G16C 20/70* (2019.01)

(52) U.S. Cl.
CPC ........... *G06Q 10/087* (2013.01); *G06Q 30/04* (2013.01); *G16C 20/70* (2019.02)

(58) Field of Classification Search
CPC ....... G06Q 10/087; G06Q 30/04; G16C 20/70
(Continued)

(56) References Cited

U.S. PATENT DOCUMENTS

| 5,086,412 A | 2/1992 | Jaffe et al. |
| 5,383,150 A | 1/1995 | Nakamura et al. |

(Continued)

FOREIGN PATENT DOCUMENTS

| CN | 110300974 A | 10/2019 | |
| CN | 114975617 A * | 8/2022 | .......... H01L 27/1159 |

(Continued)

OTHER PUBLICATIONS

Li et al., "Effect of Annealing on Ferroelectric Properties of Nanometre baTiO3 Ceramics Prepared by High Pressure Sintering Method," Chins. Phys. Lett. vol. 24, No. 1 (2007), pp. 244-247.

(Continued)

*Primary Examiner* — Russell S Glass
(74) *Attorney, Agent, or Firm* — MUGHAL GAUDRY & FRANKLIN PC

(57) ABSTRACT

A method for monetizing ferroelectric process development is described. In at least one embodiment, the method comprises procuring a target material based on a model driven selection which is based on charge, mass and magnetic moment, and/or mass of the atomic constituents of the target material. The method further comprises applying the target material to a fabrication process to build a ferroelectric device. The method further comprises generating a notification indicative of procurement of the target material and application of the target material. The method further comprises electronically transmitting the notification to a cus- (Continued)

tomer, wherein the notification includes an invoice having a line item associated with a cost of the procuring of the target material and application of the target material.

17 Claims, 19 Drawing Sheets

(58) Field of Classification Search
USPC .......................................................... 705/28
See application file for complete search history.

(56) References Cited

U.S. PATENT DOCUMENTS

| | | | |
|---|---|---|---|
| 5,539,279 A | 7/1996 | Takeuchi et al. | |
| 5,739,563 A | 4/1998 | Kawakubo et al. | |
| 5,796,079 A | 8/1998 | Kim et al. | |
| 6,002,608 A | 12/1999 | Tanabe | |
| 6,043,526 A | 3/2000 | Ochiai | |
| 6,274,388 B1 | 8/2001 | Aggarwal et al. | |
| 6,346,741 B1 | 2/2002 | Buskirk et al. | |
| 6,368,910 B1 | 4/2002 | Sheu et al. | |
| 6,388,281 B1 | 5/2002 | Jung et al. | |
| 6,500,678 B1 | 12/2002 | Aggarwal et al. | |
| 6,587,367 B1 | 7/2003 | Nishimura et al. | |
| 6,643,163 B2 | 11/2003 | Takashima | |
| 6,656,301 B2 | 12/2003 | Kirby | |
| 6,656,748 B2 | 12/2003 | Hall et al. | |
| 6,713,342 B2 | 3/2004 | Celii et al. | |
| 6,717,838 B2 | 4/2004 | Hosoi | |
| 6,720,600 B2 | 4/2004 | Okita | |
| 6,728,128 B2 | 4/2004 | Nishimura et al. | |
| 6,798,686 B2 | 9/2004 | Takashima | |
| 6,906,944 B2 | 6/2005 | Takeuchi et al. | |
| 7,029,925 B2 | 4/2006 | Celii et al. | |
| 7,075,134 B2 | 7/2006 | Araujo et al. | |
| 7,169,621 B2 | 1/2007 | Hasegawa et al. | |
| 7,173,844 B2 | 2/2007 | Lee et al. | |
| 7,405,959 B2 | 7/2008 | Koide et al. | |
| 7,426,130 B2 | 9/2008 | Jeon | |
| 7,791,922 B2 | 9/2010 | Doumae et al. | |
| 8,300,446 B2 | 10/2012 | Qidwai | |
| 8,441,833 B2 | 5/2013 | Summerfelt et al. | |
| 8,665,628 B2 | 3/2014 | Kawashima | |
| 8,865,628 B2 | 10/2014 | Manabe et al. | |
| 9,472,560 B2 | 10/2016 | Ramaswamy et al. | |
| 9,786,348 B1 | 10/2017 | Kawamura et al. | |
| 9,812,204 B1 | 11/2017 | Yan et al. | |
| 10,847,201 B2 | 11/2020 | Manipatruni et al. | |
| 10,998,025 B2 | 5/2021 | Manipatruni et al. | |
| 11,295,358 B1 | 4/2022 | Komarevtsev et al. | |
| 11,482,270 B1 | 10/2022 | Dokania et al. | |
| 11,741,428 B1 * | 8/2023 | Manipatruni ......... | G16C 20/70 705/28 |
| 2002/0079520 A1 | 6/2002 | Nishihara et al. | |
| 2002/0125517 A1 | 9/2002 | Nakamura | |
| 2002/0153550 A1 | 10/2002 | An et al. | |
| 2003/0119211 A1 | 6/2003 | Summerfelt et al. | |
| 2003/0129847 A1 | 7/2003 | Celii et al. | |
| 2003/0141528 A1 | 7/2003 | Ito | |
| 2004/0027873 A1 | 2/2004 | Nishihara | |
| 2004/0104754 A1 | 6/2004 | Bruchhaus et al. | |
| 2004/0129961 A1 | 7/2004 | Araujo et al. | |
| 2004/0233696 A1 | 11/2004 | Kang | |
| 2004/0245547 A1 | 12/2004 | Stipe | |
| 2005/0012126 A1 | 1/2005 | Udayakumar et al. | |
| 2005/0214954 A1 | 9/2005 | Maruyama et al. | |
| 2005/0230725 A1 | 10/2005 | Aggarwal et al. | |
| 2005/0244988 A1 | 11/2005 | Wang et al. | |
| 2006/0001070 A1 | 1/2006 | Park et al. | |
| 2006/0002170 A1 | 1/2006 | Kumura et al. | |
| 2006/0006447 A1 | 1/2006 | Kim et al. | |
| 2006/0073613 A1 | 4/2006 | Aggarwal et al. | |
| 2006/0073614 A1 | 4/2006 | Hara | |
| 2006/0134808 A1 | 6/2006 | Summerfelt et al. | |
| 2006/0138507 A1 | 6/2006 | Kijima et al. | |
| 2006/0258113 A1 | 11/2006 | Sandhu et al. | |
| 2007/0275484 A1 | 11/2007 | Mitsui | |
| 2007/0298521 A1 | 12/2007 | Obeng et al. | |
| 2008/0073680 A1 | 3/2008 | Wang | |
| 2008/0081380 A1 | 4/2008 | Celii et al. | |
| 2008/0101107 A1 | 5/2008 | Shiga et al. | |
| 2008/0107885 A1 | 5/2008 | Alpay et al. | |
| 2008/0191252 A1 | 8/2008 | Nakamura et al. | |
| 2009/0003042 A1 | 1/2009 | Lee et al. | |
| 2010/0070324 A1 | 3/2010 | Bock et al. | |
| 2012/0127776 A1 | 5/2012 | Kawashima | |
| 2012/0134196 A1 | 5/2012 | Evans, Jr. et al. | |
| 2012/0313218 A1 | 12/2012 | Fujimori et al. | |
| 2014/0208041 A1 | 7/2014 | Hyde et al. | |
| 2014/0247642 A1 | 9/2014 | Madhan et al. | |
| 2015/0069481 A1 | 3/2015 | Sun et al. | |
| 2015/0294702 A1 | 10/2015 | Lee et al. | |
| 2017/0277459 A1 | 9/2017 | Rodriguez et al. | |
| 2018/0166453 A1 | 6/2018 | Müller | |
| 2018/0226418 A1 | 8/2018 | Morandi et al. | |
| 2018/0286987 A1 | 10/2018 | Lee et al. | |
| 2018/0323309 A1 | 11/2018 | Ando et al. | |
| 2019/0051642 A1 | 2/2019 | Hyde et al. | |
| 2019/0051815 A1 | 2/2019 | Kakinuma et al. | |
| 2019/0115353 A1 | 4/2019 | O'Brien et al. | |
| 2019/0138893 A1 | 5/2019 | Sharma et al. | |
| 2020/0004583 A1 | 1/2020 | Kelly et al. | |
| 2020/0051607 A1 | 2/2020 | Pan et al. | |
| 2020/0273867 A1 | 8/2020 | Manipatruni et al. | |
| 2020/0357453 A1 | 11/2020 | Slesazeck et al. | |
| 2021/0090662 A1 | 3/2021 | Mennenga et al. | |
| 2021/0111179 A1 | 4/2021 | Shivaraman et al. | |
| 2021/0142837 A1 | 5/2021 | Yu et al. | |
| 2021/0193209 A1 | 6/2021 | Swami et al. | |
| 2021/0398580 A1 | 12/2021 | Yuh | |
| 2022/0301662 A1 | 9/2022 | Yamano et al. | |
| 2022/0352379 A1 * | 11/2022 | Lin ........................ | H10B 51/30 |

FOREIGN PATENT DOCUMENTS

| | | |
|---|---|---|
| CN | 110300974 B | 5/2023 |
| JP | H10255484 A | 9/1998 |
| JP | 2003123465 A | 4/2003 |
| JP | 2005057103 A | 3/2005 |
| KR | 100481867 B1 | 4/2005 |
| KR | 20050105695 A | 11/2005 |
| KR | 100895740 B1 | 4/2009 |
| TW | 200718237 A | 5/2007 |
| TW | 200935151 A | 8/2009 |
| TW | 201725736 A | 7/2017 |
| WO | 20130147295 | 10/2013 |
| WO | 2015167887 A1 | 11/2015 |
| WO | 2021112247 A1 | 6/2021 |

OTHER PUBLICATIONS

Advisory Action notified Jul. 25, 2022 for U.S. Appl. No. 17/339,850.
Advisory Action notified Nov. 16, 2021 for U.S. Appl. No. 16/287,953.
Advisory Action notified Nov. 16, 2021 for U.S. Appl. No. 16/288,004.
Advisory Action notified Nov. 16, 2021 for U.S. Appl. No. 16/288,006.
Chandler, T. "An adaptive reference generation scheme for 1T1C FeRAMs", 2003 Symposium on VLSI Circuits. Digest of Technical Papers (IEEE Cat. No. 03CH37408), Kyoto, Japan, 2003, pp. 173-174.
Final Office Action notified Apr. 25, 2022 for U.S. Appl. No. 16/287,953.
Final Office Action notified Aug. 15, 2022 for U.S. Appl. No. 17/346,083.
Final Office Action notified Jun. 13, 2022 for U.S. Appl. No. 17/339,850.
Final Office Action notified May 11, 2022 for U.S. Appl. No. 16/288,004.
Final Office Action notified May 11, 2022 for U.S. Appl. No. 16/288,006.
Final Office Action notified Oct. 7, 2021 for U.S. Appl. No. 16/287,953.

(56) References Cited

OTHER PUBLICATIONS

Final Office Action notified Oct. 7, 2021 for U.S. Appl. No. 16/288,004.
Final Office Action notified Oct. 7, 2021 for U.S. Appl. No. 16/288,006.
Final Office Action notified Sep. 12, 2022 for U.S. Appl. No. 17/367,217.
Fu et al., "Understanding the Microwave Annealing of Silicon," AIP Advances 7, 035214 (2017); https://doi.org/10.1063/1.4978912; Published Mar. 15, 2017, (8 pages).
Gudmundsson et al., "Foundations of Physical Vapor Deposition with Plasma Assistance," Plasma Sources Sci. Technol. 31 (2022) 083001; https://doi.org/10.1088/1361-6595/ac7f53; pp. 1-33 (34 pages).
Gupta et al., "Buried Power Rail Integration with Si FinFETs for CMOS Scaling beyond the 5 nm Node," 2020 IEEE Symposium on VLSI Technology, Jun. 16-19, 2020, Honolulu, HI, US. 2 pages. DOI: 10.1109/VLSITechnology18217.2020.9265113.
Gupta et al., "Buried Power Rail Scaling and Metal Assessment for the 3 nm Node and Beyond," 2020 IEEE International Electron Devices Meeting (IEDM), Dec. 12-18, 2020, San Francisco, CA, US. 4 pages. DOI: 10.1109/IEDM13553.2020.9371970.
International Preliminary Report on Patentability notified Sep. 10, 2021 for PCT Patent Application No. PCT/US2020/018870.
International Preliminary Report on Patentability notified Sep. 10, 2021 for PCT Patent Application No. PCT/US2020/066963.
International Search Report & Written Opinion notified Jun. 19, 2020 for U.S. Patent Application No. PCT/US2020/018879.
International Search Report & Written Opinion notified Jun. 24, 2020 for PCT Patent Application No. PCT/US2020/018870.
Josefson "Evaluation of Ferroelectric Materials for Memory Applications," Thesis Collection, Dudley Knox Library, Monterey, CA; http://hdl.handle.net/10945/27767, Jun. 1990; (99 pages).
Juan et al., "Electrical Characterization of Metal-Ferroelectric (Mn-substituted BiFeO3)-Insulator (HfO2)-Semiconductor Capacitors for Nonvolatile Memory Applications," Microelectronic Engineering 86, 2009. pp. 1845-1848.
Jung, D. et al., "Highly manufacturable 1T1C 4 Mb FRAM with novel sensing scheme," International Electron Devices Meeting 1999. Technical Digest (Cat. No.99CH36318), Washington, DC, USA, 1999, pp. 279-282., International Electron Devices Meeting 1999. Technical Digest (Cat. No.99CH36318), Washington, DC, USA, 1999, pp. 279-282.
Khanal et al. "Grain-Size Dependence of Piezoelectric Properties in Thermally Annealed BaTiO3 Ceramics," Journal of the Ceramic Society of Japan 126 (7) pp. 536-541 2018. http://doi.org/10.2109/jcersj2.17260.
Kim et al., "Application of Ferroelectric Materials for Improving Output Power of Energy Harvesters," Nano Convergence (2018) 5:30; https://doi.org/10.1186/s40580-018-0163-0; (16 pages).
Kossar et al., "Ferroelectric Polarization Induced Memristive Behavior in Bismugh Ferrite (BiFeO3) Based Memory Devices," Superlattices and Microstructures 148 (2020) 106726. 14 pages.
Lin et al., "Metal-Ferroelectric (BiFeO3)-Insulator(Y2O3)-Semiconductor Capacitors and Field Effect Transistors for nonvolatile Memory Applications," Appl. Phys. Lett. 64, 142908 (2009); https://doi.org/10.1063/1.3114403.
Lou et al., "Local Phase Decomposition as a Cause of Polarization Fatigue in Ferroelectric Thin Films," Physical Review Letters, PRL 97, 177601 (2006); DOI: 10.1103/PhysRevLett.97.177601; (4 pages).
Machado et al., "Band Gap Tuning of Solution-Processed Ferroelectric Perovskite BiFe1-XCoxO3 Thin Films," Chem. Mater. 2019, 31. pp. 947-954.
Mathur et al., "Buried Bitline for sub-5nm SRAM Design," 2020 IEEE International Electron Devices Meeting (IEDM), San Francisco, CA, US. 4 pages. DOI: 10.1109/IEDM13553.2020.9372042.
McGovern et al., "Grain Size Influences Activation Energy and Migration Pathways in MAPbBr3 Perovskite Solar Cells," Journal Phys. Chem. Kett. 2021, 12. pp. 2423-2428.
Noguchi et al., "Ferroelectrics with a Controlled Oxygen-Vacancy Distribution by Design," Scientific Reports 9:4225; Published Mar. 12, 2019; https://doi.org/10.1038/s41598-019-40717-0; www.nature.com/scientificreports. pp. 1-10 (10 pages).
Non-Final Office Action notified Aug. 5, 2020 for U.S. Appl. No. 16/287,953.
Non-Final Office Action notified Aug. 5, 2020 for U.S. Appl. No. 16/288,004.
Non-Final Office Action notified Aug. 5, 2020 for U.S. Appl. No. 16/288,006.
Non-Final Office Action notified Aug. 16, 2022 for U.S. Appl. No. 17/367,217.
Non-Final Office Action notified Dec. 20, 2021 for U.S. Appl. No. 16/288,004.
Non-Final Office Action notified Jan. 18, 2022 for U.S. Appl. No. 16/287,953.
Non-Final Office Action notified Jan. 19, 2022 for U.S. Appl. No. 16/288,006.
Non-Final Office Action notified Jun. 13, 2022 for U.S. Appl. No. 17/346,083.
Non-Final Office Action notified Jun. 15, 2022 for U.S. Appl. No. 17/367,101.
Non-Final Office Action notified Jun. 26, 2020 for U.S. Appl. No. 16/287,876.
Non-Final Office Action notified Jun. 27, 2022 for U.S. Appl. No. 17/315,143.
Non-Final Office Action notified Mar. 7, 2022 for U.S. Appl. No. 17/339,850.
Non-Final Office Action notified Mar. 30, 2022 for U.S. Appl. No. 17/346,083.
Non-Final Office Action notified Mar. 31, 2022 for U.S. Appl. No. 17/346,087.
Non-Final Office Action notified May 8, 2023 for U.S. Appl. No. 18/088,413.
Salahuddin et al., "Buried Power SRAM DTCO and System-Level Benchmarking in N3," 2020 Symposium on VLSI Technology Digest of Technical Papers—JFS3.3 IEEE. 2 pages.
Salahuddin et al., "SRAM with Buried Power Distribution to Improve Write Margin and Performance in Advanced Technology Nodes," IEEE Electron Device Letters, vol. 40, Issue: 8, Aug. 2019. 4 pages. DOI: 10.1109/LED.2019.2921209.
Seager et al., "Charge Trapping and Device Behavior in Ferroelectric Memories," Appl. Phys. Lett. 68(2660); https://doi.org/10.1063/1.116273; published Jun. 4, 1998 (4 pages).
Second Office Action notified Jul. 26, 2022 for Taiwan Patent Application No. 110129115.
Si et al., "Ultrafast Measurements of Polarization Switching Dynamics on Ferroelectric and Anti-Ferroelectric Hafnium Zirconium Oxide," Appl. Phys. Lett. 115, 072107 (2019); https://doi.org/10.1063/1.5098786. Published Aug. 14, 2019, (6 pages).
Tanaka, S. et al., "FRAM cell design with high immunity to fatigue and imprint for 0.5 /spl mu/m 3 V 1T1C 1 Mbit FRAM", in IEEE Transactions on Electron Devices, vol. 47, No. 4, pp. 781-788, Apr. 2000.
Wang et al., "On the Importance of the Work Function and Electron Carrier Density of Oxide Electrodes for the Functional Properties of Ferroelectric Capacitors," Phys. Status Solidi RRL 2020, 14, 1900520; DOI: 10.1002/pssr.201900520; (9 pages).
Wang et al., "The Microstructure, Electric, Optical and Photovoltaic Properties of BiFeO3 Thin Films Prepared by Low Temperature Sol-Gel Method," Materials (Basel). May 3, 2019;12(9):1444. 10 pages. doi: 10.3390/ma12091444.
Wiki_Ferroelectric RAM 2022: https ://web.archive .org/web/20220823113457 /https://en. wikipedia .org/wiki/ Ferroelectric_RAM (Year: 2022).
Wu et al., "Enhancement of Ferroelectricity in 5 nm Metal-Ferroelectric-Insulator Technologies by Using a Strained TIN Electrode," Nanomaterials 2022, 12, 468. https://doi.org/10.3390/nano12030468; (8 pages).
Yamaoka, K. et al., "A 0.9-V 1T1C SBT-based embedded nonvolatile FeRAM with a reference voltage scheme and multilayer shielded bit-line structure", in IEEE Journal of Solid-State Circuits, vol. 40, No. 1, pp. 286-292, Jan. 2005.

(56) References Cited

OTHER PUBLICATIONS

Yeh et al. "Fabrication and Investigation of Three-Dimensional Ferroelectric Capacitors for the Application of FeRAM," AIP Advances 6, 035128 (2016); https://doi.org/10.1063/1.4945405, Published Online: Mar. 30, 2016, 13 pages.
Yu et al., "Atomic layer deposited ultrathin metal nitride barrier layers for ruthenium interconnect applications" Journal of Vacuum Science & Technology A 35, 03E109 (2017); https://doi.org/10.1116/1.4979709.
Zhao et al., "Improved Ferroelectric Properties in Hf_0._5Zr_0.5_O_2_ Thin Films by Microwave Annealing," Thin Films by Microwave Annealing. Nanomaterials 2022, 12, 3001. https://doi.org/10.3390/nano12173001; (8 pages).
Non-Final Office Action notified Nov. 4, 2022 for U.S. Appl. No. 17/530,362.
Non-Final Office Action notified Nov. 21, 2022 for U.S. Appl. No. 7/532,657.
Non-Final Office Action notified Oct. 12, 2022 for U.S. Appl. No. 17/530,365.
Non-Final Office Action notified Oct. 26, 2022 for U.S. Appl. No. 17/531,577.
Non-Final Office Action notified Sep. 1, 2022 for U.S. Appl. No. 17/339,850.
Non-Final Office Action notified Sep. 2, 2022 for U.S. Appl. No. 17/315,139.
Non-Final Office Action notified Sep. 7, 2022 for U.S. Appl. No. 17/530,360.
Non-Final Office Action notified Sep. 15, 2022 for U.S. Appl. No. 17/315,111.
Notice of Allowance notified Apr. 20, 2022 for U.S. Appl. No. 17/359,311.
Notice of Allowance notified Aug. 8, 2022 for U.S. Appl. No. 17/529,258.
Notice of Allowance notified Aug. 17, 2022 for U.S. Appl. No. 17/346,087.
Notice of Allowance notified Aug. 22, 2022 for U.S. Appl. No. 7/390,791.
Notice of Allowance notified Aug. 25, 2022 for U.S. Appl. No. 17/367,101.
Notice of Allowance notified Aug. 31, 2022 for U.S. Appl. No. 17/359,325.
Notice of Allowance notified Jan. 12, 2021 for U.S. Appl. No. 16/287,876.
Notice of Allowance notified Jul. 27, 2020 for U.S. Appl. No. 16/287,927.
Notice of Allowance notified Jun. 9, 2022 for U.S. Appl. No. 16/288,006.
Notice of Allowance notified Jun. 10, 2022 for U.S. Appl. No. 16/288,004.
Notice of Allowance notified Jun. 13, 2022 for U.S. Appl. No. 16/287,953.
Notice of Allowance notified Jun. 14, 2023 for U.S. Appl. No. 18/088,413.
Notice of Allowance notified Jun. 15, 2022 for U.S. Appl. No. 17/367,083.
Notice of Allowance notified Jun. 23, 2022 for U.S. Appl. No. 17/367,172.
Notice of Allowance notified Jun. 23, 2022 for U.S. Appl. No. 17/367,210.
Notice of Allowance notified Nov. 9, 2022 for U.S. Appl. No. 17/390,831.
Notice of Allowance notified Nov. 17, 2022 for U.S. Appl. No. 17/530,363.
Notice of Allowance notified Oct. 20, 2022 for Taiwan Patent Application No. 110129115.
Notice of Allowance notified Sep. 13, 2022 for U.S. Appl. No. 17/530,364.
Notice of Allowance notified Sep. 14, 2022 for U.S. Appl. No. 17/530,360.
Notice of Allowance notified Sep. 21, 2022 for U.S. Appl. No. 17/530,366.
Notice of Allowance notified Sep. 23, 2022 for U.S. Appl. No. 17/339,850.
Notice of Allowance notified Sep. 26, 2022 for U.S. Appl. No. 17/367,217.
Notice of Allowance notified Sep. 27, 2022 for U.S. Appl. No. 17/346,083.
Notice of Preliminary Rejection notified Oct. 28, 2022 for Korean Patent Application No. 10-2021-7027303.
Ogiwara, R. et al., "A 0.5-/spl mu/m, 3-V 1T1C, 1-Mbit FRAM with a variable reference bit-line voltage scheme using a fatigue-free reference capacitor", in IEEE Journal of Solid-State Circuits, vol. 35, No. 4, pp. 545-551, Apr. 2000.
Oh, S. et al. "Noble FeRAM technologies with MTP cell structure and BLT ferroelectric capacitors", IEEE International Electron Devices Meeting 2003, Washington, DC, USA, 2003, pp. 34.5.1-34.5.4.
Pan et al., "Giant Energy Density and High Efficiency Achieved in Bismuth Ferrite-Based Film Capacitors Via Domain Engineering," Nature Communications 2018, 9:1813, 8 pages, DOI: 10.1038/s41467-018-04189-6.
Pandey, "Memory Improvement in Lead-Free BiFeO3 Ferroelectric with High-K Al2)e Buffer Layer for Non-Volatile Memory Applications," Applied Physics A (2018) 124:507, 8 pages. https://doi.org/10.1007/s00339-018-1926-5.
Pesic et al., "Comparative Study of Reliability of Ferroelectric and Anti-Ferroelectric Memories," IEEE Transactions on Device and Materials Reliability, vol. 18, No. 2, Jun. 2018. pp. 154-162 (9 pages).
Pesic et al., "How to Make DRAM Non-Volatile? Anti-Ferroelectrics: A New Paradigm for Universal Memories," 2016 IEEE International Electron Devices Meeting (IEDM). pp. 1161-1164 (4 pages).
Pham "Atomic Layer Deposition Enabled Synthesis of multiferroic Nanostructures," 2015 Thesis/dissertation, University of California, Los Angeles. 238 pages.
Raj et al., "Effect of Annealing Time in the Low-Temperature Growth of BFO Thin Films Spin Coated on Glass Substrates," Journal of Materials Science: materials in Electronics, Oct. 2013, 10 pages, DOI: 10.1007/s10854-013-1374-0.
Restriction Requirement notified Apr. 5, 2023 for U.S. Appl. No. 18/088,413.
Restriction Requirement notified Apr. 15, 2022 for U.S. Appl. No. 17/315,111.
Restriction Requirement notified Apr. 15, 2022 for U.S. Appl. No. 17/315,139.
Restriction Requirement notified Aug. 5, 2022 for U.S. Appl. No. 17/359,325.
Restriction Requirement notified Aug. 26, 2022 for U.S. Appl. No. 17/390,796.
Restriction Requirement notified Mar. 23, 2022 for U.S. Appl. No. 17/315,143.
Robertson et al., "High-K Materials and metal Gates for CMOS Applications," Materials Science and Engineering: R: Reports, vol. 88, Feb. 2015, pp. 1-41.
Run-Lan et al., "Study on Ferroelectric Behaviors and Ferroelectric Nanodomains of YMno3 Thin Film", Acta Phys. Sin. vol. 63, No. 18 (2014). Supported by the National Natural Science Foundation of China. DOI: 10.7498/aps.187701. 6 pages.
Ryckaert et al., "Extending the Roadmap Beyond 3nm Through System Scaling Boosters: A Case Study on Buried Power Rail and Backside Power Delivery," 2019 Electron Devices Technology and Manufacturing Conferences (EDTM), IEEE. pp. 50-52 (3 pages).
International Search Report & Written Opinion notified Nov. 13, 2023 for PCT Patent Application No. PCT/US2023/070932.
Office Action notified Jun. 4, 2024 for Taiwanese Patent Application No. 112128100.

\* cited by examiner

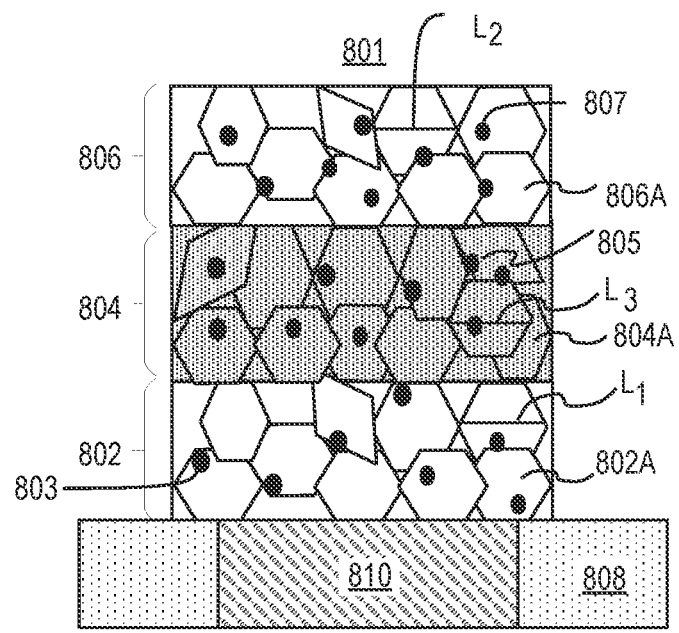
Fig. 8A
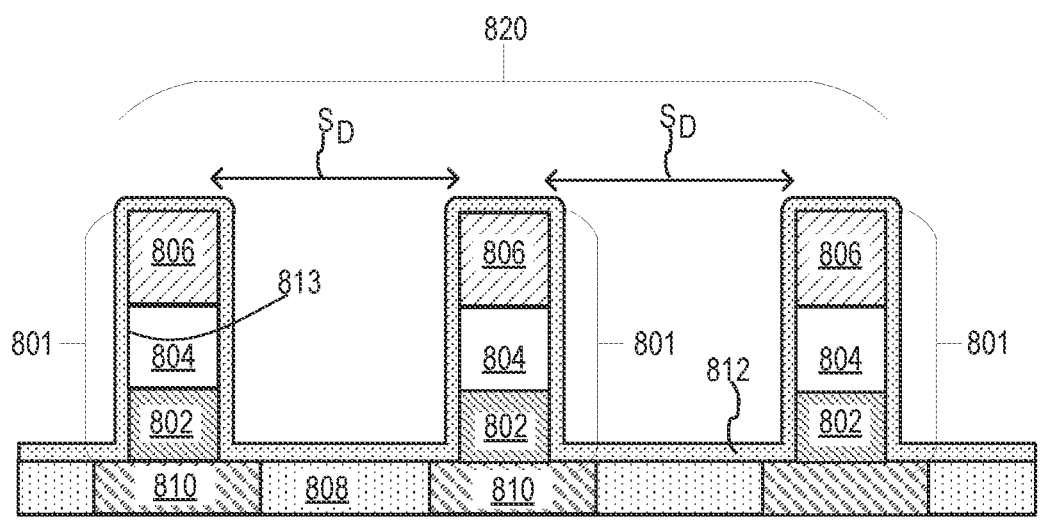
Fig. 8B
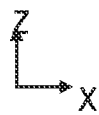

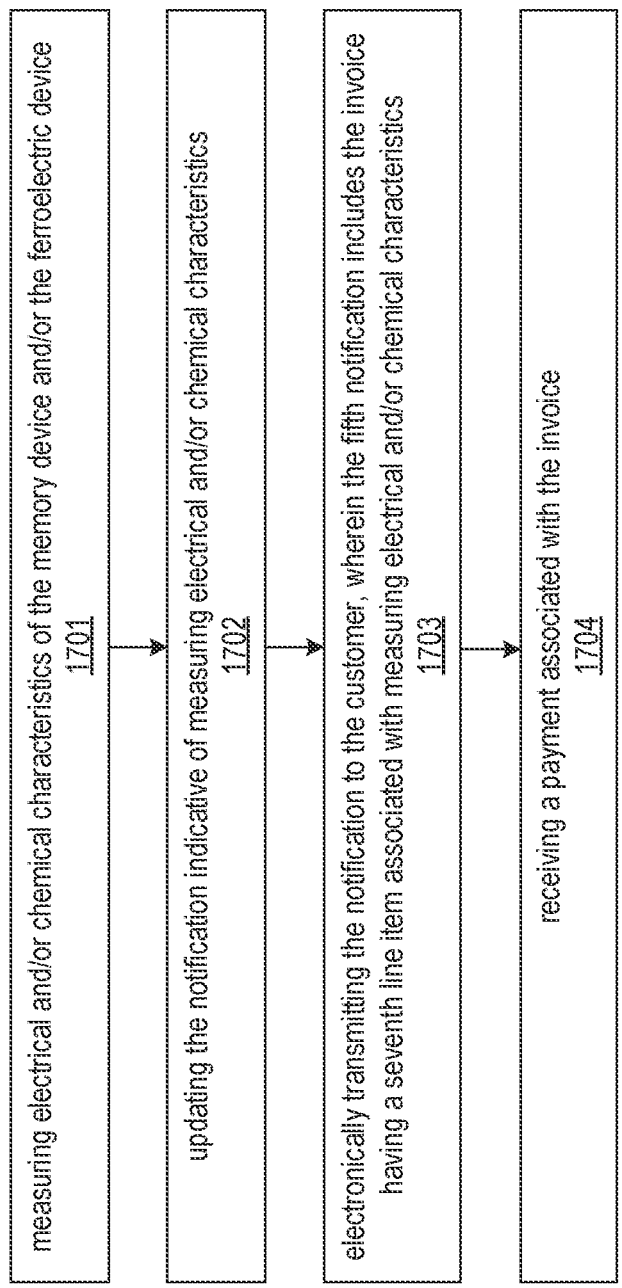

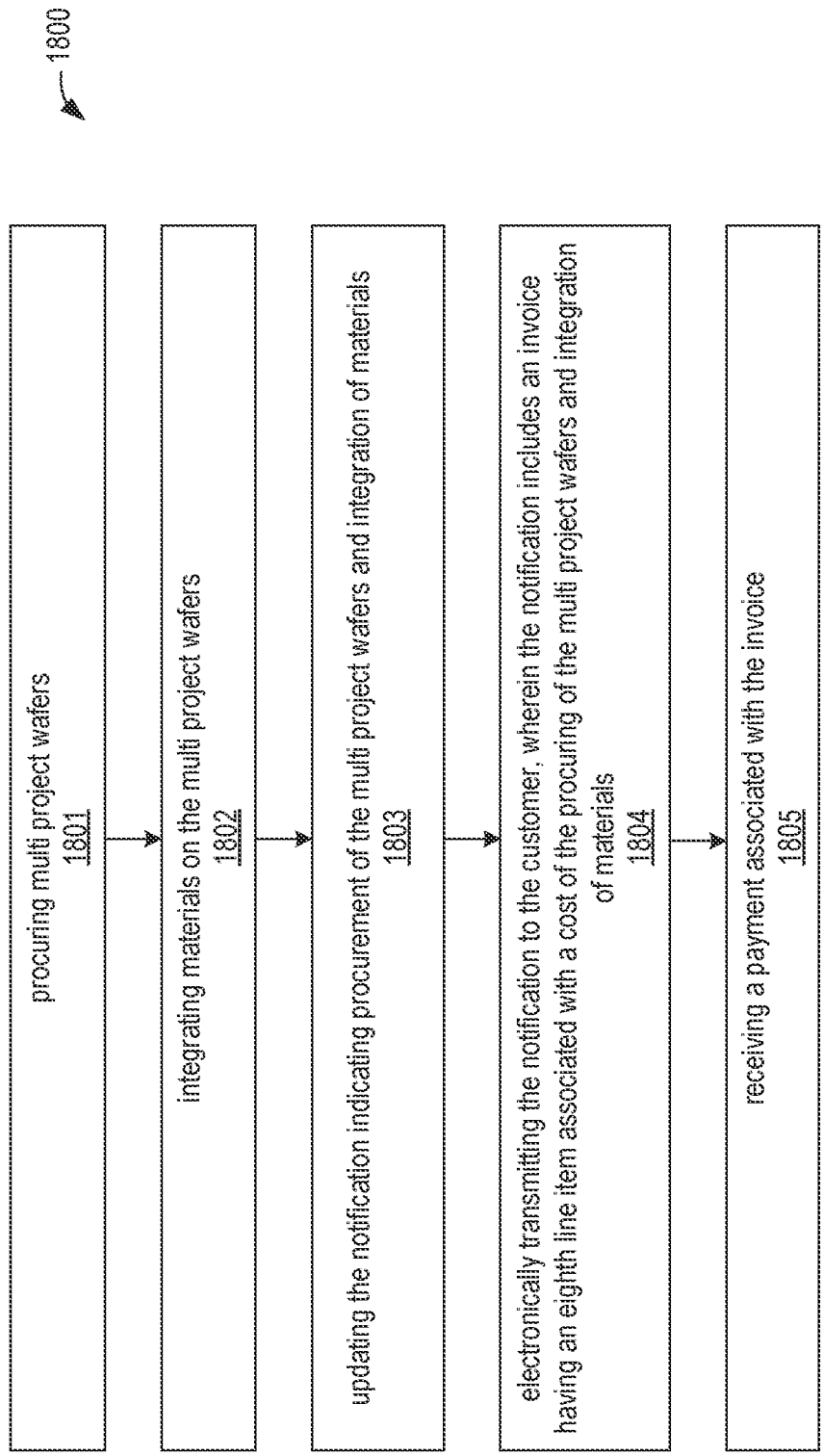

ITERATIVE MONETIZATION OF PRECURSOR IN PROCESS DEVELOPMENT OF NON-LINEAR POLAR MATERIAL AND DEVICES

CLAIM FOR PRIORITY

This application claims priority to U.S. patent application Ser. No. 18/088,413, filed on Dec. 23, 2022, titled "ITERATIVE MONETIZATION OF PROCESS DEVELOPMENT OF NON-LINEAR POLAR MATERIAL AND DEVICES," and now issued as U.S. Pat. No. 11,741,428 on Aug. 29, 2023, and which is incorporated by reference in entirety.

TECHNICAL FIELD

At least one embodiment pertains process development of non-linear polar material and devices. For example, at least one embodiment pertains to a process of procuring a material to apply to fabrication process to build a device with non-linear polar material and monetizing the process according to various novel techniques described herein.

BACKGROUND

Developing a process to fabricate a device is a complex process. Examples of such devices include devices having non-linear polar material (e.g., ferroelectric, paraelectric, non-linear dielectric) devices, transistors coupled to such devices, etc. Extensive research and development are exerted to develop a process, which can later be applied by fabrication foundries.

BRIEF DESCRIPTION OF THE DRAWINGS

Embodiments may be understood more fully from the detailed description given below and from accompanying drawings of various embodiments of the disclosure, which, however, should not be taken to limit the disclosure to the specific embodiments, but are for explanation and understanding only.

FIG. 8A illustrates a cross-sectional illustration of a memory device obtained by patterning multi-layer stack obtained in FIG. 7 in accordance with at least one embodiment.

FIG. 8B illustrates a cross-sectional illustration of a plurality of memory devices, where individual devices are at least laterally surrounded by an encapsulation layer in accordance with at least one embodiment.

FIG. 17 illustrates a flowchart of iterative monetizing of a measuring electrical and/or chemical characteristics of a memory device, in accordance with at least one embodiment.

FIG. 18 illustrates a flowchart of iterative monetizing of multi-project wafers as they are used for development of a device, in accordance with at least one embodiment.

DETAILED DESCRIPTION

Figure 1:
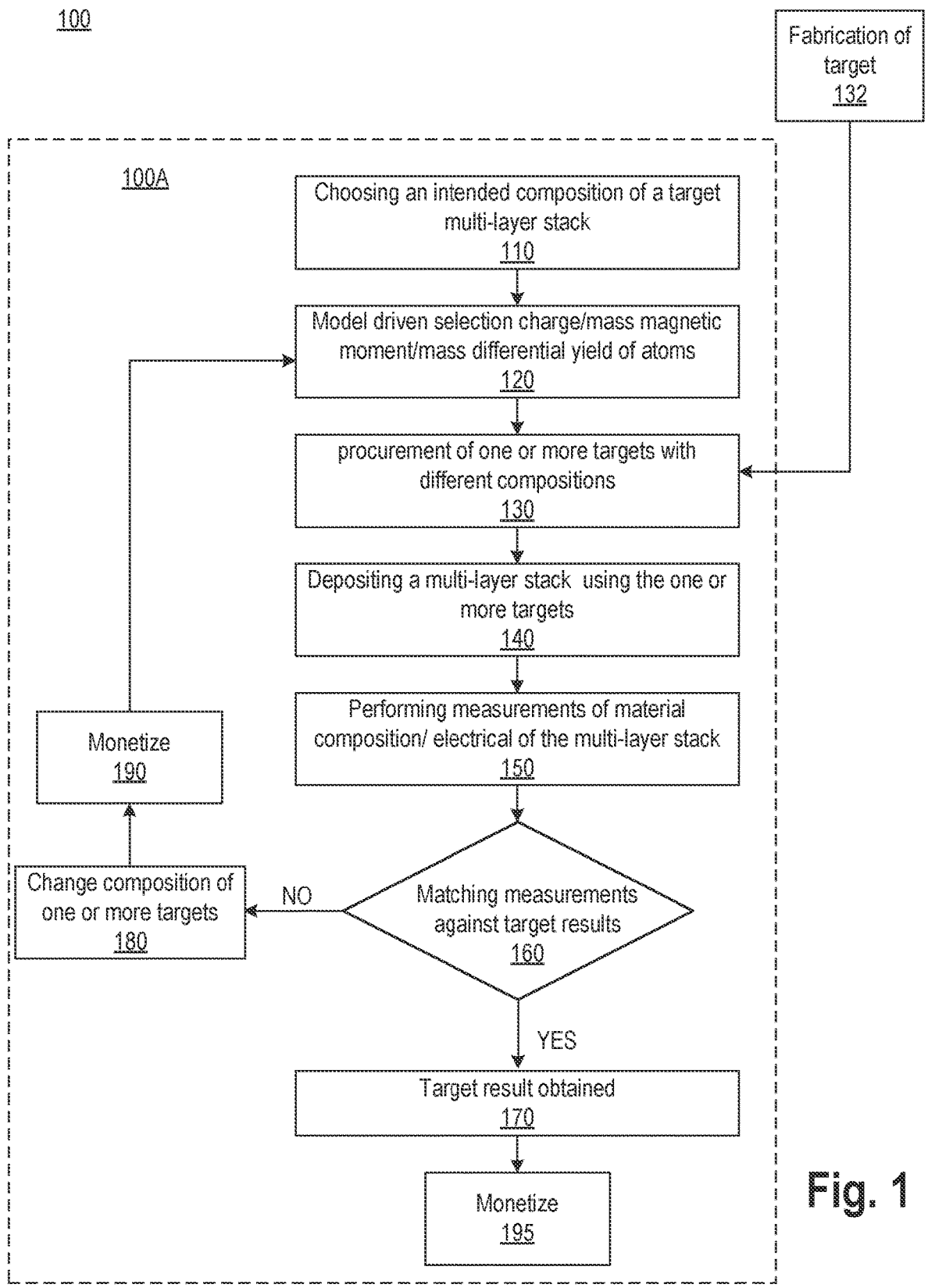
FIG. 1 is a flow diagram of a method of iteratively developing a multilayer stack for application to memory devices, and monetizing iterative method, in accordance with at least one embodiment.

In at least one embodiment, an iterative method of monetizing one or more aspects of development of a semiconductor device is provided. In at least one embodiment, a method or scheme is described that monetizes procuring of a target material and/or applying target material to a fabrication process. In at least one embodiment, a target material is procured. In at least one embodiment, target material can be based on model driven selection which is based on charge, mass and magnetic moment, and/or mass of atomic constituents of target material. In at least one embodiment, target material is based on an expert providing target material. In at least one embodiment, target material is applied to a fabrication process to build a ferroelectric device. In at least one embodiment, a notification is generated which is indicative of procurement of target material and application of target material. In at least one embodiment, notification is electronically transmitted to a customer. In at least one embodiment, notification includes an invoice having a first line item associated with a cost of procuring target material and application of target material.

In at least one embodiment, a method or scheme is provided that monetizes procuring of precursor and/or feeding precursor to build a device. In at least one embodiment, a precursor is precured from a vendor. In at least one embodiment, precursor is fed to fabrication process to build a ferroelectric or paraelectric device (or any device having non-linear polar material). In at least one embodiment, a notification indicative of procurement of a volume of precursor and feeding of precursor is updated. In at least one embodiment, notification is electronically transferred to a customer, wherein notification includes invoice having a line item (e.g., second line item) associated with a cost of volume of precursor and feeding of precursor.

In at least one embodiment, a method or scheme is described that monetizes number of turns associated with a fabrication process. In at least one embodiment, several lot turns associated with fabrication process is determined. In at least one embodiment, for each lot turn, a base cost is determined. In at least one embodiment, a total cost as a sum of base cost for each lot turn is computed. In at least one embodiment, a notification indicative of number of lot turns and total cost is updated. In at least one embodiment, electronically transmitting notification to customer is electronically transmitted. In at least one embodiment, notification includes invoice having a line item (e.g., third line item) associated with number of lot turns and total cost.

In at least one embodiment, a method or scheme is described that monetizes procuring of a material is bulk or separate and/or applying material to build a device. In at least one embodiment, a material in bulk is procured. In at least one embodiment, material is applied to a fabrication process to build a ferroelectric device. In at least one embodiment, a notification indicative of procurement of material and application of material is updated. In at least one embodiment, notification is electronically transferred to customer. In at least one embodiment, notification includes an invoice having a line item (e.g., fourth line item) associated with a cost of procuring of material and application of material.

In at least one embodiment, a method or scheme is described that monetizes fabricating a memory device by coupling one or more transistors to a device. In at least one embodiment, a memory device is fabricated by coupling one or more transistors to ferroelectric device. In at least one embodiment, notification is updated with indication of fabricating memory device. In at least one embodiment, notification is electronically transmitted to customer. In at least one embodiment, notification includes invoice having a line item (e.g., fifth line item) associated with fabricating memory device.

In at least one embodiment, a method or scheme is described that monetizes procuring a transistor wafer and/or fabricating a memory device on transistor wafer. In at least one embodiment, a transistor wafer is provided. In at least one embodiment, a memory device is fabricated on transistor wafer, wherein memory device includes a ferroelectric or paraelectric device. In at least one embodiment, a notification is updated indicating procurement of transistor wafer and fabrication of memory device. In at least one embodiment, notification is electronically transmitted to customer, wherein notification includes an invoice having a line item (e.g., sixth line item) associated with a cost of procuring of transistor wafer and fabrication of memory device.

In at least one embodiment, a method or scheme that monetizes measuring electrical and/or chemical characteristics of memory device is provided. In at least one embodiment, electrical and/or chemical characteristics are measured of memory device and/or ferroelectric device or paraelectric device. In at least one embodiment, notification is updated indicative of measuring electrical and/or chemical characteristics. In at least one embodiment, notification to customer is electronically transmitted. In at least one embodiment, notification includes invoice having a line item (e.g., seventh line item) associated with measuring electrical and/or chemical characteristics. In at least one embodiment, electrical and/or chemical characteristics of target material are modeled to generate a representative model of the target material. In at least one embodiment, a model may be expressed as a series of functions that fit characteristic plots of target material. In at least one embodiment, a notification indicative of representative model is generated. In at least one embodiment, notification is electronically transmitted to a customer, wherein notification includes an invoice having a line item associated with a cost of modeling electrical and/or chemical characteristics.

In at least one embodiment, a method or scheme that monetizes procuring multi project wafers and/or integrating materials on multi-project wafers is provided. In at least one embodiment, multi project wafers are procured. In at least one embodiment, materials are integrated on multi-project wafers. In at least one embodiment, a notification is updated indicating procurement of multi-project wafers and integration of materials. In at least one embodiment, notification is electronically transferred to a customer. In at least one embodiment, notification includes an invoice having a line item (e.g., an eighth line item) associated with a cost of procuring of multi-project wafers and integration of materials. In at least one embodiment, an iterative method of multi-layer stack development for device applications is provided. In at least one embodiment, an iterative method is monetized for at least one iteration and/or after all iterations are complete.

Here, numerous specific details are set forth, such as structural schemes and detailed fabrication methods to provide a thorough understanding of at least one embodiment. It will be apparent to one skilled in art that at least one embodiment may be practiced without these specific details. In other instances, well-known features, such as process equipment and device operations, are described in lesser detail to not unnecessarily obscure at least one embodiment. Furthermore, it is to be understood that at least one embodiment shown in a figure is an illustrative representation and are not necessarily drawn to scale.

FIG. 1 illustrates a flow diagram of method 100 of iteratively developing a multilayer stack for application to memory devices, and monetizing an iterative method, in accordance with at least one embodiment. Capacitors with a wide variety of materials are implemented for memory applications such as RAM applications. In at least one embodiment, nonlinear polar materials offer a wide array of technologically important properties, including ferroelectricity, piezoelectricity, metal-like electrical conductivity, semiconduction, pyroelectricity, etc. Perovskites are an example of non-linear polar material (e.g., materials with chemical formula $ABO_3$). In at least one embodiment, perovskite materials are implemented in capacitors such for high density FeRAM applications owing to their low power consumption and high on/off ratio. In at least one embodiment, perovskite FeRAM devices (herein FeRAM devices) may be desirable over other forms of memory such as magnetic tunnel junction (MTJ)-memory device for fabrication advantages. In at least one embodiment, MTJ can include a stack of 10 or more layers. In at least one embodiment, a perovskite based FeRAM device may include three layers for functionality. In at least one embodiment, ferroelectric dielectric is contained between two electrode layers independent of device geometry. In at least one embodiment, electrode layers may also include perovskite materials to enable lattice matching and reduction in electrical resistance. In at least one embodiment, introduction of lead-free perovskite materials offer additional environmental benefits without sacrificing device performance.

Integration of nonlinear polar materials into silicon semiconductor chip fabrication processes can be challenging. From fabrication of a multi-layer stack to patterning devices, and integrating one or more devices with one or more transistors, iterations in experimentation can be technically challenging and extremely time consuming.

Challenges in iterations in experimentation for thin film development begins with material selection and engineering. In at least one embodiment, film with thickness of less than 100 nm may be sufficiently thin. While individual layers can be deposited in controlled amounts and stoichiometry of films can be tuned with careful experimentation, deposition of multiple layers in a multi-layer stack is even more challenging. In at least one embodiment, depositing an individual layer in a multi-layer stack involves forming with correct stoichiometry, crystallinity, crystal structure templating, thickness, and surface roughness to facilitate device functionality. In at least one embodiment, depositing layers in a multi-layer stack is expected to have same requisite chemical and electrical properties as single layers, but also be compatible with each other to fabricate a functional memory device. In at least one embodiment, lattice matching between layers, preserving surface roughness of layers to not amplify effects of roughness on upper layers, and avoiding interdiffusion of elements while depositing are some challenges. In at least one embodiment, conductive layers to be implemented as electrodes are expected to have correct work function and dielectric layer is expected to have appropriate polarization and polarization charge density (above 0.1 micro coulomb/cm$^2$). In at least one embodiment, multi-layer stack is to provide operational capability at adequately low operational voltage (such as below 2V) and devices formed from multi-layer stack are expected to have an endurance of at least e15 for commercial viability.

In at least one embodiment, obtaining a multi-layer stack with requisite layer properties begins with targeting deposition process for individual layers. In at least one embodiment, deposition process can be physical vapor deposition (PVD), or atomic layer deposition (ALD) based. In at least one embodiment, PVD deposition uses adequate targets for sputter deposition and atomic layer deposition uses appropriate pre-cursors for nucleation. In at least one embodiment, for PVD deposition, targets can be elemental alloys or compounds. In at least one embodiment, modeling of correct charge/mass or magnetic moment to mass for elements in target and other variables and estimating correct deposition conditions (e.g., power, pressure, temperature, etc.) is used to form layers with appropriate stoichiometry. In at least one embodiment, modeling can enable substantially accurate prediction of sputter yield, a useful parameter in PVD deposition. In at least one embodiment, iterative nature of experimentation is sequentially and carefully based on results from one or more previous experiments.

In at least one embodiment, when a multi-layer stack is patterned to form a device, chemical and mechanical properties can be altered during fabrication process. In at least one embodiment, air breaks can introduce additional oxygen and/or hydrogen (among other contaminants) leading to chemical reactions at interfaces and formation of undesirable residual layers. Such residual layers may cause increased circuit resistance. Furthermore, interdiffusion of elements in residual layers can adversely impact parameters such as remnant polarization. In at least one embodiment, thermal anneal can mitigate potential grain size and defect issues as well as device patterning related issues. In at least one embodiment, thermal anneal can provide hydrogen terminations of dangling bonds. In at least one embodiment, implementation of thermal anneal post stack deposition/and or post device fabrication may use careful consideration of thermal budget.

In at least one embodiment, integrating one or more devices with transistors involves experimentations to engineer multi-layer stack to address asymmetry in 1T-1C (one transistor, one capacitor) bit-cell operational voltage characteristics. In at least one embodiment, aspects of experimentation involve addressing integration issues associated with fabricating a memory device on a same substrate as a transistor, but post transistor fabrication. In at least one embodiment, experimentation involves determining appropriate device layout and density requirements to form a useful memory chip. In at least one embodiment, size of memory devices and transistors may be matched for optimal integrated memory performance. In at least one embodiment, a high operational capacitor voltage may necessitate a transistor that can provide a high current or operate at sufficiently high voltages. In at least one embodiment, where sequence of fabrication involves fabricating a transistor prior to multi-layer stack deposition, thermal budget for performing an anneal can be an important factor for material selection. In at least one embodiment, experimentation around a total thermal flux is used for integrated 1T-1C device fabrication.

In at least one embodiment, method 100 begins at operation 110 with determining a target multi-layer stack, where initial material layer stack comprises an initial ferroelectric material of a form AA'BB'O$_3$. In at least one embodiment, initial material layer stack comprises an initial ferroelectric material of a form AA'BB'O$_3$N$_x$F$_Y$. In at least one embodiment, method 100 continues at operation 120 by implementing a model driven target selection based on charge:mass ratio and a magnetic moment:mass ratio, and other variables, that enable accurate prediction of sputter yield. In at least one embodiment, method 100 continues at operation 130 by procuring an initial one or more targets, wherein individual targets in initial one or more targets comprise single elements or a combination of elements with a respective initial stoichiometric composition. In at least one embodiment, method to procure targets uses communication with external parts suppliers to request targets that include alloys with certain stoichiometric properties as referenced by operation 132. In at least one embodiment, targets can use fabrication lead time from third parties if they are not readily available.

In at least one embodiment, method 100 continues at operation 140 by depositing a multi-layer stack using an initial one or more targets to form initial multi-layer stack. In at least one embodiment, method 100 continues at operation 150 by performing measurements of chemical composition and electrical properties of initial multi-layer stack. In at least one embodiment, method 100 continues at operation 160 by matching measurements of chemical composition and electrical properties of initial multi-layer stack against target results and determining whether measurements are within a tolerance level of target results. In at least one embodiment, method 100 may end at operation 170 if measurements are within a tolerance level (e.g., within 5%) of target results. In at least one embodiment, method 100 continues at operation 180 by making modifications in response to determining that measurements are not within tolerance level. In at least one embodiment, modifications include changing composition of one or more layers in initial multi-layer stack to form a successive multi-layer stack by implementing a model driven selection, modifying single elements or combination of elements in a successive one or more targets to comprise a respective second stoichiometric composition, and procuring successive one or more targets.

In at least one embodiment, after composition of one or more targets is modified, a notification is used to a customer of method 100. In at least one embodiment, this notification may indicate that one or more targets were procured, layers were deposited on one or more targets to form a stack, and measurements were then made on stack. In at least one embodiment, notification may be electronically transmitted at operation 190 to monetize tasks listed on notification. In at least one embodiment, notification may include an invoice having a line item associated with a cost of procuring of target material and application of target material. Here, "invoice" may generally refer to one of: a bill of sale, an estimate cost, royalty, equity share, or cost-plus estimate.

In at least one embodiment, method 100 iterates by implementing a model driven selection, modifying stoichiometric composition of one or more targets in successive one or more targets, procuring successive one or more targets, depositing successive multi-layer stacks, performing compositional and electrical measurements, matching measurements with target values, and/or determining whether measurement results are within tolerance level of target values, until target results are obtained.

While FIG. 1 is an iterative methodology to fabricate a multi-layer stack, in at least one embodiment, one or more operations (such as operations 110-180) can be further broken down in to sub operations as will be discussed below.

In at least one embodiment, beginning with operation 110, choosing an intended composition of a target multilayer stack includes material selection for least a pair of electrodes for a capacitor and a dielectric material that includes ferroelectric, paraelectric, or anti-ferroelectric properties.

In at least one embodiment, dashed box 100A defines operations that are conducted by a first entity and fabrication of target (here, operation 132) may be carried out by a second entity such as external suppliers, where second entity is different from first entity. In at least one embodiment, once target result is obtained has described with reference to operation 170, method 100 may perform a monetizing operation 195. In at least one embodiment, monetizing operation 195 is like monetizing operation 190.

Figure 2A:
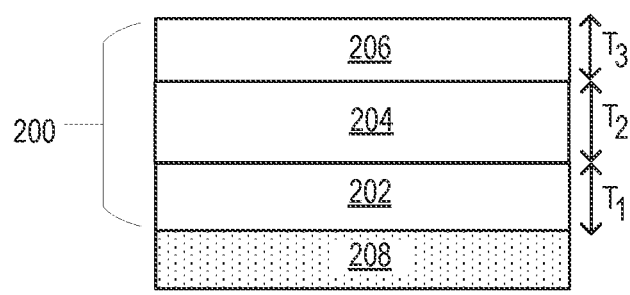
FIG. 2A is a representative tri-layer stack, in accordance with at least one embodiment.

FIG. 2A illustrates representative tri-layer stack 200, in accordance with at least one embodiment. In at least one embodiment, stack 200 includes conductive layer 202, dielectric 204 that includes a polar material and conductive layer 206 on dielectric 204. In at least one embodiment, conductive layer 202 is on substrate 208. In at least one embodiment, substrate 208 includes silicon, silicon-germanium, or germanium.

In at least one embodiment, conductive layer 202 is deposited on substrate 208. In at least one embodiment, conductive layer 202 and conductive layer 206 include a conductive oxide. In at least one embodiment, conductive oxide includes one of non-Pb perovskite metal oxides, such as but not limited to $(La,Sr)FeO_3$, $(La,Sr)CoO_3$, $(La,Ca)MnO_3$, $(La,Sr)MnO_3$, $SrRuO_3$, $Sr_2RuO_4$, $(Ba,Sr)RuO_3$, $SrMoO_3$, $(La,Sr)MnO_3$, $SrCoO_3$, $SrCrO_3$, $SrFcO_3$, $SrVO_3$, $CaMoO_3$, $SrNbO_3$, $LaNiO_3$, $YBa_2Cu_3O_7$, $BizSr_2CaCuOs$, $CaRuO_8$, $Ir_2O_x$, Ru, $RuO_x$, Mo, $MoO_x$ or $WO_x$. In at least one embodiment, conductive layer 202 and conductive layer 206 include a metal such as but not limited to Ir, Ru or W.

In at least one embodiment, dielectric 204 comprises a polar layer comprising a base polar material substitutionally doped with a dopant. In least one embodiment, dielectric 204 comprises a crystalline polar layer. In at least one embodiment, base polar material can include one or more metal elements and one or both of oxygen and nitrogen. In at least one embodiment, dopant can include a metal element of one of 4d series, 5d series, 6d series, 4f series, or 5f series.

In at least one embodiment, dielectric 204 is a ferroelectric dielectric layer that includes non-Pb based perovskite material in a form ABO3, where A and B are two cations of different sizes and O is Oxygen. In at least one embodiment, A is generally larger than B in size. In at least one embodiment, non-Pb perovskites can also be doped, e.g., by La or Lanthanides. In at least one embodiment, non-Pb perovskite material can include one or more of La, Sr, Co, Cr, K, Nb, Na, Sr, Ru, Y, Fe, Ba, Hf, Zr, Cu, Ta, Bi, Ca, Ti, or Ni. In at least one embodiment, dielectric 204 includes bismuth ferrite (BFO) with a doping material, wherein doping material is one of lanthanum, elements from lanthanide series of periodic table, or elements of a 3d 4d, 5d, 6d, 4f, or 5f series of periodic table.

In at least one embodiment, dielectric 204 includes low voltage ferroelectric (FE) material sandwiched between conductive layer 206 and conductive layer 202. In at least one embodiment, these low voltage FE materials can be of a form $AA'BB'O_3$, where A' is a dopant for atomic site A and can be an element from Lanthanides series, where B' is a dopant for atomic site B and can be an element from transition metal elements such as Sc, Ti, V, Cr, Mn, Fc, Co, Ni, Cu, or Zn. In at least one embodiment, A' may have same valency of site A, with a different ferroelectric polarizability. In at least one embodiment, voltage below 2-Volts is sufficiently low to be characterized as low voltage. In at least one embodiment, dielectric 204 of a form $AA'BB'O_3$.

In at least one embodiment, dielectric 204 includes a paraelectric material, paraelectric material comprises $SrTiO_3$, $Ba_{(x)}Sr_{(y)}TiO_3$, $HfZrO_2$, Hf—Si—O, La-substituted $PbTiO_3$, or a PMN-PT based relaxor ferroelectrics. In at least one embodiment, x is −0.05, and y is 0.95 for $Ba_{(x)}Sr_{(y)}TiO_3$.

In at least one embodiment, dielectric 204 includes an anti-ferroelectric material. In at least one embodiment, anti-ferroelectric material may include one of: PZT with >30% Zr doping or Sn doping>25%, La-doped PZT with >30% Zr doping and or Sn doping>20%, $HfSiO_2$ and $HfZrO_x$ with >30% Si and >30% Zr doping, $ZrO_2$, $NaNbO_3$, or >5% K doped $NaNbO_3$. In at least one embodiment, choice of materials depends on a variety of factors. In at least one embodiment, factors include electrical results, fabrication of devices, and integrability with a transistor.

In at least one embodiment, conductive layer 202, may be deposited to a thickness $T_1$ between 3 nm and 30 nm (inclusive). In at least one embodiment, conductive layer 206 may be deposited to a thickness $T_3$ between 3 nm and 30 nm (inclusive). In at least one embodiment, dielectric 204 may be deposited to a thickness $T_2$ between 1 nm and 30 nm (inclusive).

Figure 2B:
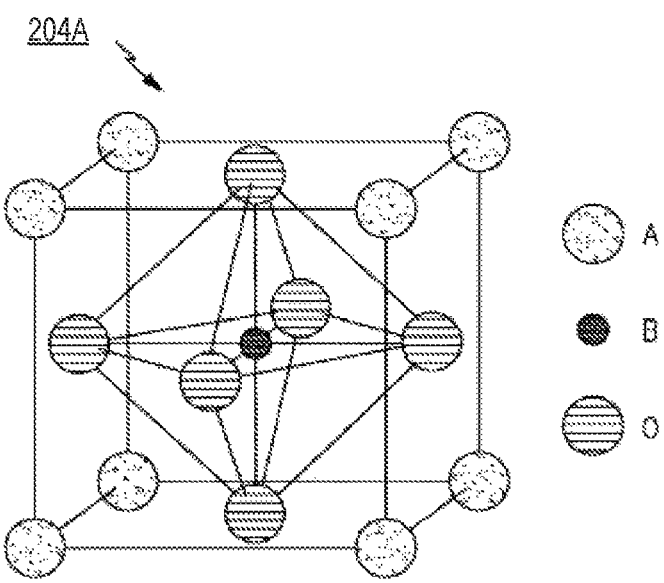
FIG. 2B schematically illustrates a perovskite crystal structure of a polar layer of material layer stack in FIG. 2A, in accordance with at least one embodiment.

FIG. 2B schematically illustrates a perovskite crystal structure of a polar layer of material layer stack in FIG. 2A, in accordance with at least one embodiment. In at least one embodiment, crystalline polar layer has a perovskite structure 204A. In at least one embodiment, perovskite structure 204A represents a crystalline oxide in a paraelectric state, which may have a chemical formula ABO3, where each of A and B represent one or more metal cations and O represents an oxygen anion. In at least one embodiment, crystalline polar layer can have more than one element represented by A (e.g., A1, A2, . . . AN) and/or more than one element represented by B (e.g., B1, B2, . . . BN), and can be doped with one or more dopants represented by A' (e.g., A'1, A'2, . . . A'N) and/or one or more dopants represented by B' (e.g., B'1, B'2, . . . B'N), as described above. In at least one embodiment, A-site cations occupy corners, while B-site cations sit in body center of perovskite structure 204A. In at least one embodiment, three oxygen atoms per unit cell rest on faces of perovskite structure 204A. In at least one embodiment, various perovskite structures have, without limitation, a lattice constant close to approximately 4 Angstroms (A) due to rigidity of oxygen octahedra network and well-defined oxygen ionic radius of 1.35 A. In at least one embodiment, many different cations can be substituted on both A and B sites as dopants to achieve various advantageous properties described herein while maintaining overall crystal structure. In at least one embodiment, a dopant atom can occupy A or B sites to form substitutionally doped solid solutions. In at least one embodiment, a dopant occupying A sites can have a very different effect on base polar material than a dopant occupying B sites.

In at least one embodiment, for a polar layer comprising barium titanate ($BaTiO_3$), which may be a paraelectric material having a cubic perovskite structure, A sites are occupied by Ba atoms while Ti atoms occupy B sites and are surrounded by octahedra of 0 atoms, and O atoms are located at center of each face of unit cell. In at least one embodiment, for $BaTiO_3$, in paraelectric phase, perovskite structure 204A may be cubic or tetragonal above Curie temperature (e.g., above 130 degrees Celsius). In at least one embodiment, in paraelectric phase, O atoms may occupy a mid-position with respect to each pair of O atoms on opposing faces of unit cell. In at least one embodiment, below Curie temperature, in ferroelectric phase, perovskite structure 204A may have a tetragonal structure in which B sub lattice (e.g., Ti sub lattice in $BaTiO_3$) and O atoms may shift in opposite direction with respect to Ba atoms, taken as reference. In at least one embodiment, these atomic shifts may be accompanied by a small relaxation of unit cell that becomes tetragonal (when paraelectric phase is cubic) or further elongated tetragonal (when paraelectric phase is tetragonal) and produce a stable polarization (e.g., about 26 $\mu C/cm^2$). In at least one embodiment, in tetragonal phase, cubic symmetry is broken, resulting in six symmetry equivalent variants with polarization along [100], [010] and [001] directions.

Figure 3A:
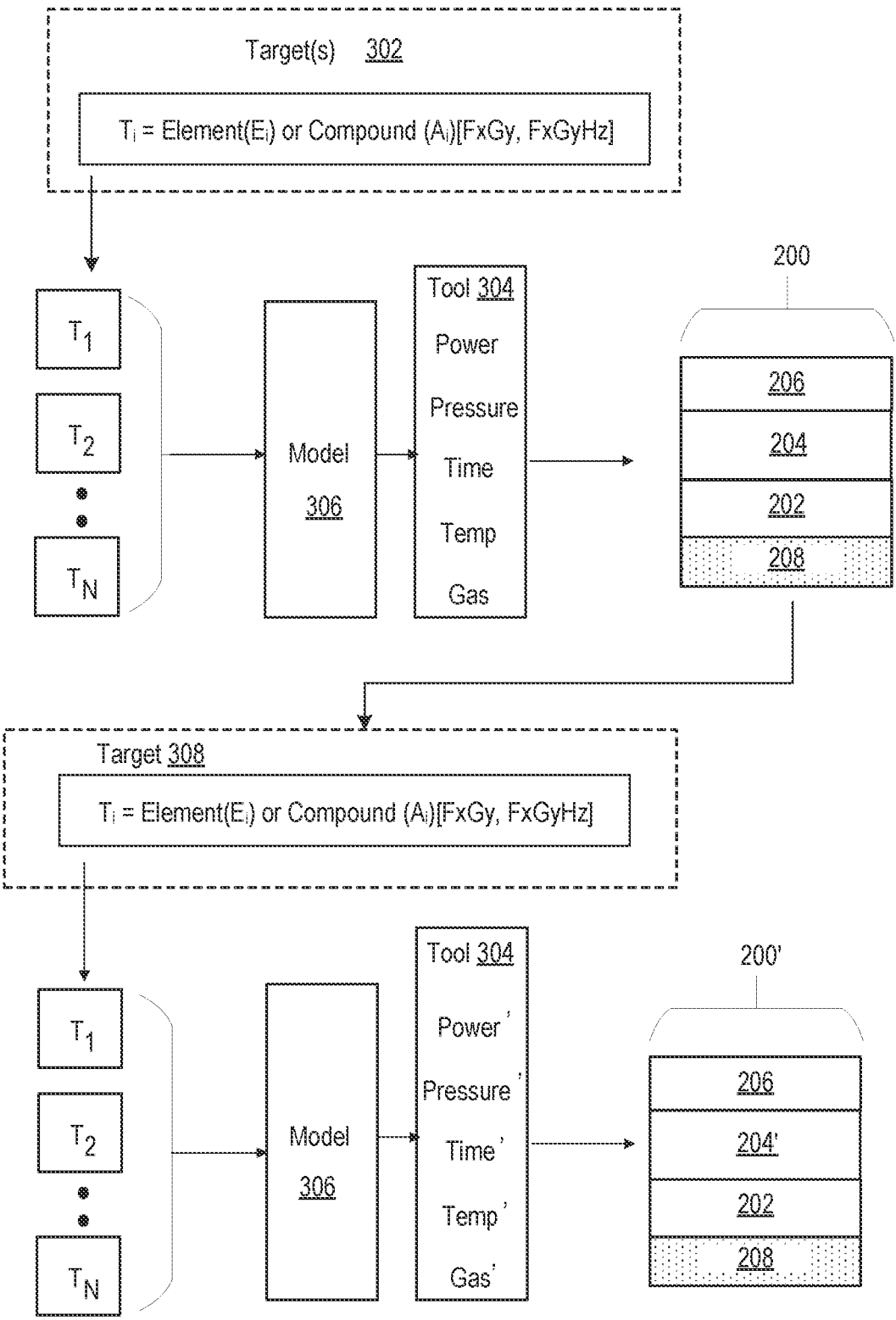
FIG. 3A illustrates a flow diagram of method illustrating iterations in a multilayer stack deposition as performed utilizing one or more targets in a tool, in accordance with at least one embodiment.

FIG. 3A illustrates a flow diagram of method 300A illustrating iterations in a multilayer stack deposition as performed utilizing one or more targets 302 in tool 304, in at least one embodiment. In at least one embodiment, tool 304 is a deposition tool. In at least one embodiment, tool 304 is a physical vapor deposition tool. In at least one embodiment, one or more targets 302 includes individual targets $T_i$. In at least one embodiment, $T_i$ includes an element $E_i$ or an alloy$_i$, where subscript "i" corresponds to number of targets 302, such as for example 1, 2, 3, 4, etc. In at least one embodiment, number of individual targets $T_i$ depends on a material that is to be deposited, e.g., N refers to a last target. In at least one embodiment, number of individual targets $T_i$ can depend on number of elements present in material deposited. In at least one embodiment, where individual targets $T_i$ are alloys or compounds ($A_i$), $A_i$ can be binary alloys or compounds of a form $F_xG_y$, or ternary alloys or compounds of a form $F_xG_yH_z$, where F and G can be metals and H can be a non-metal like O.

In at least one embodiment, for a polar material such as $BiFeO_3$, number of elements is 3. In at least one embodiment, Bi and Fe can be available as >99% pure elemental sputtering targets. In at least one embodiment, Bi and Fe can be available as >4599% pure elemental sputtering targets. In at least one embodiment, oxygen may be inserted into sputtering environment as a gas or be part of a compound with iron in a binary compound. In at least one embodiment, for sputtering $BiFeO_3$, total number of targets can be 1 or 2 (e.g., N can range from 1 to 2).

In at least one embodiment, sputtering targets including multi-elemental compounds can be fabricated by arc-melting or radio-frequency melting of a mixture of metals in a vacuum or gas atmosphere. In at least one embodiment, gas can be inert or include O, N, H, or F. In at least one embodiment, sputtering targets including multi-elemental compounds can be fabricated by mixing constituent binary oxides in stoichiometric ratio, followed by Hot Isostatic Pressing (HIP). In at least one embodiment, sputtering targets including multi-elemental compounds can be fabricated by mixing constituent binary oxides in stoichiometric ratio, followed by cold pressing powder mixture into a ceramic compact using a pneumatic press, followed by sintering of ceramic compact at high temperatures to obtain desired chemistry and density of target.

In at least one embodiment, density of target is between 85 and 95% of theoretical material density. In at least one embodiment, model 306 that utilizes information about charge:mass ratio and magnetic moment:mass ratio of ions (e.g., elemental or ionized alloys) can be implemented to estimate sputtering coefficients and rates within a PVD tool. In at least one embodiment, charge:mass ratio and magnetic moment:mass ratio are used in enabling an accurate prediction of sputter yield, deposition rates and composition of a deposited layer in deposition systems that utilize magnetic fields. In at least one embodiment, computational model further utilizes operational parameters of tool 304 to calculate deposition rates on a substrate. In at least one embodiment, operational parameters may include radio frequency (RF) magnetron deposition power, chamber operational pressure, sputtering time, temperature of chamber, and/or substrate, and types and concentration of gases flowing during deposition. In at least one embodiment, gas utilized for deposition can be inert such as Ar and/or include other gases such as such as $O_2$, $N_2$, $H_2$, Kr, and Ne.

In at least one embodiment, deposition process to form stack 200 may include deposition of layers without an air break. In at least one embodiment, air break may be avoided to prevent interfacial layers from forming between electrode layers and dielectric layer. In at least one embodiment, interfacial layers can provide additional source of oxygen during cycling of devices fabricated from stack 200. In at least one embodiment, additional sources of oxygen may not be controllable and may lead to instability or loss of endurance during device cycling. In at least one embodiment, for a certain combination of targets $A_i$, deposition process may yield dielectric 204 in stack 200. In at least one embodiment, stack 200 has properties of stack 200 described in association with FIG. 2A. In at least one embodiment, properties of stack 200 may be determined by a series of measurement methods outlined in Table 1. In at least one embodiment, dielectric 204 may not have desired properties of a target dielectric layer, such as correct stoichiometry, thickness, uniformity, etc.

In at least one embodiment, same targets 302 may be utilized to deposit a new stack 200'. In at least one embodiment, a customer may be billed, and an invoice sent, upon using same targets 302 to deposit new stack 200'. In at least one embodiment, tool deposition conditions can be changed based on inputs to model 306. In at least one embodiment, a customer may be billed, and an invoice sent, upon changing deposition conditions based on inputs to model 306. In at least one embodiment, a new set of operational parameters power', chamber operational pressure', sputtering time', temperature', and gases' may be implemented to achieve stack 200'. In at least one such embodiment, stack 200' comprising dielectric 204', may have desired properties of a target dielectric layer, such as correct stoichiometry, thickness, uniformity, etc.

In at least one embodiment, process to alter PVD tool parameters can be iteratively changed based on inputs from measurements and model 306 until stack 200' achieves target values that are within tolerance of results that are desired. In at least one embodiment, for an iterative change, an invoice may be generated, and billed to a customer, for service of iterative change. In at least one embodiment, power' can range between 5 Watts per square inch and 75 Watts per square inch, chamber operational pressure' can range between 0.5 milli Torr and 30 milli Torr, and temperature' of chamber and or substrate can range between room temperature to 650 degrees Celsius.

Figure 3B:
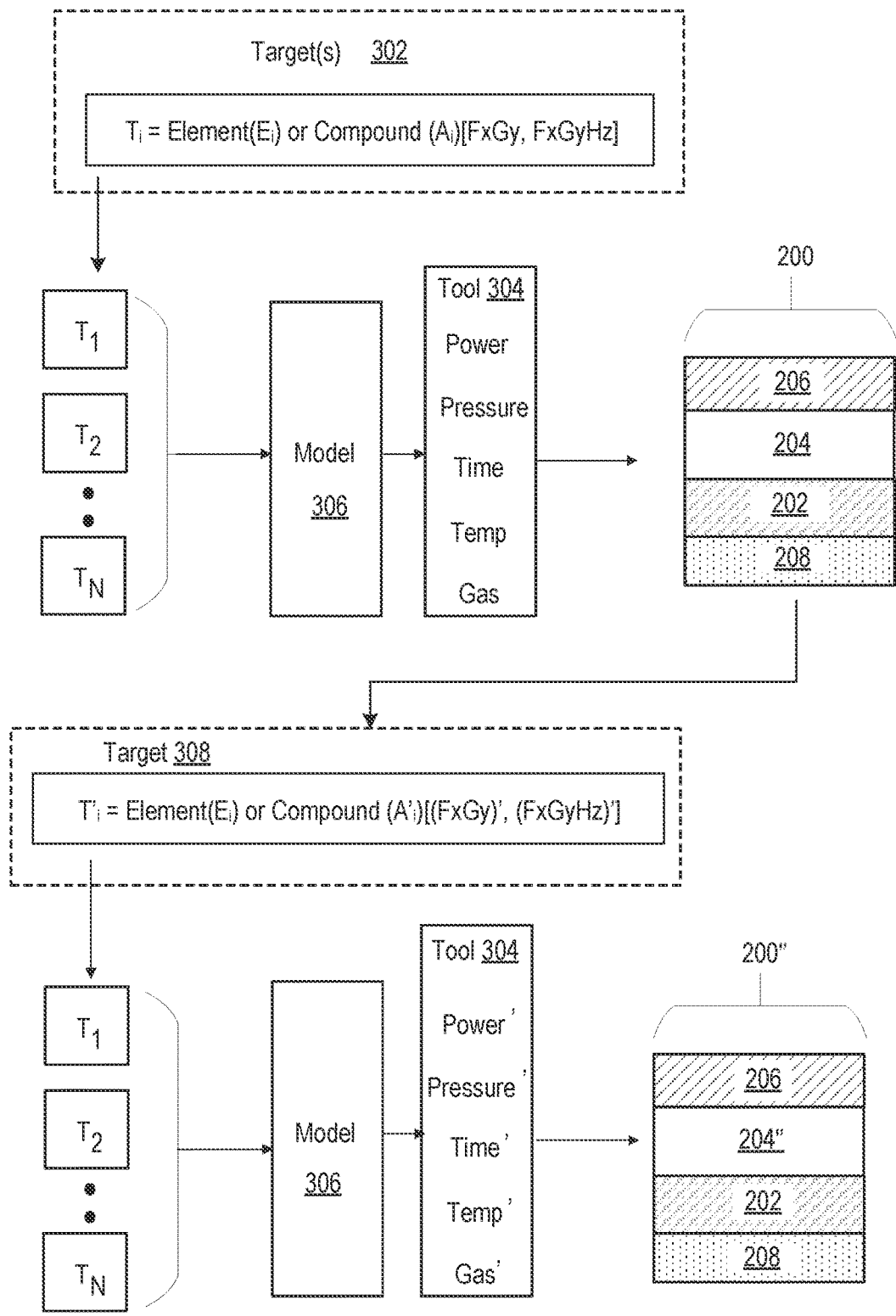
FIG. 3B illustrates a flow diagram of method illustrating iterations in a multilayer stack deposition as performed utilizing one or more targets in a tool, in accordance with at least one embodiment.

In at least one embodiment, it may be deduced that, because of methodology in FIG. 3A, target results can be substantially within reach if one or more individual targets $T_i$ are changed. In at least one embodiment, this method is illustrated in FIG. 3B. In at least one embodiment, after initial experimentation and obtaining stack 200, a new one or more targets 308 may be implemented, in accordance with method 300B.

In at least one embodiment, targets 308 includes one or more individual targets $T_i'$, that include one or more new compounds $A_i'$ $\{(F_xG_y)_i', (F_xG_yH_z)_i'\}$. In at least one embodiment, individual stoichiometry within compounds including Bi, Fe, and O can be different by 5% from compounds including Bi, Fe, and O in first one or more targets. In at least one embodiment, individual stoichiometry within compounds including Bi, Fe, and O can be different by 10% from compounds including Bi, Fe, and O in first one or more targets. In at least one embodiment, elemental targets $E_i$ may have same purity as before, or purity can be changed. In at least one embodiment, a new purity can range from 99% to 99.5% in some examples.

In at least one embodiment, model 306 may be implemented on new targets $T_i'$ to compute tool parameters. In at least one embodiment, a customer may be billed, and an invoice sent, for implementing model 306. In at least one embodiment, tool parameters may be non-different than those utilized to fabricate stack 200. In at least one embodiment, one or more properties of dielectric 204 is altered with an iteration in modification in one or more targets. In at least one embodiment, a customer may be billed, and an invoice sent, upon altering properties of dielectric 204. In at least one embodiment, due to differences in targets $T_i'$, dielectric layer 204" in stack 200" may have useful properties, such as stoichiometry, thickness, uniformity, etc. In at least one embodiment, stack 200' comprising dielectric 204' and 204", respectively, may have desired properties of a target dielectric layer that are substantially matched and within tolerance of target results.

In at least one embodiment, while experimentation with emphasis on a $BiFeO_3$ dielectric 204 has been described, methods 300A and 300B may be generalized to apply to a variety of material choices described above for dielectric 204. In at least one embodiment, $BiFeO_3$ may also be doped with other materials such as a metal element of one of 3d, 4d, 5d, 6d, 4f, or 5f series of periodic table.

While experimentation with emphasis on dielectric 204 has been described, method 300A or method 300B may be utilized to iteratively fine tune chemical and electrical properties, such as resistivity, work function, crystallinity, etc. of conductive layers 202 and 206, in accordance with at least one embodiment. In at least one embodiment, a customer may be billed, and an invoice sent, for interactive fine tuning of chemical and electrical properties of conductive layers 202 and 206. In at least one embodiment, properties of conductive layers 202 and 206 may be tuned individually or collectively as part of stack 200.

Referring to FIGS. 3A and 3B, in at least one embodiment, when an in-situ deposition process is carried out when depositing to form stack 200, 200', or 200", targets $T_i$ or $T_i'$ can include materials utilized in depositing all layers in stack 200, 200', or 200". In at least one embodiment, minimizing iterations is useful to accelerate development and lower costs. In at least one embodiment, a customer may be billed, and an invoice sent, upon completing deposition process to form stack 200, 200', or 200".

In at least one embodiment, evaluation of chemical, mechanical, and electrical properties of stack 200, 200', and 200" can be made by a plethora of measurement techniques. In at least one embodiment, a customer may be billed, and an invoice sent, upon application of a measurement technique. In at least one embodiment, it is useful to perform a ferroelectric hysteresis measurement (P-E loop) to analyze how effective a particular ferroelectric dielectric layer is. In at least one embodiment, a simple measurement technique involves applying an electric field applied across a sample. In at least one embodiment, a field is attenuated by a resistor divider. In at least one embodiment, a measured current through circuit is integrated into charge by a capacitor that is positioned in series with a sample. In at least one embodiment, an applied voltage and measured voltage drop (current measurement) signals are utilized to generate a Polarization vs Electric field loop by an oscilloscope.

In at least one embodiment, after evaluation of chemical, mechanical and electrical properties of stack, a notification is used to a customer. In at least one embodiment, this notification may indicate that one or more targets 302 or 308 were procured and evaluation of chemical, mechanical, and electrical properties of stack were performed. In at least one embodiment, notification may be electronically transmitted to customer to monetize tasks listed on notification. In at least one embodiment, notification may include an invoice having a line item associated with a cost of procuring of one or more targets 302 or 308 and evaluation of chemical, mechanical, and electrical properties of stack.

Figure 4:
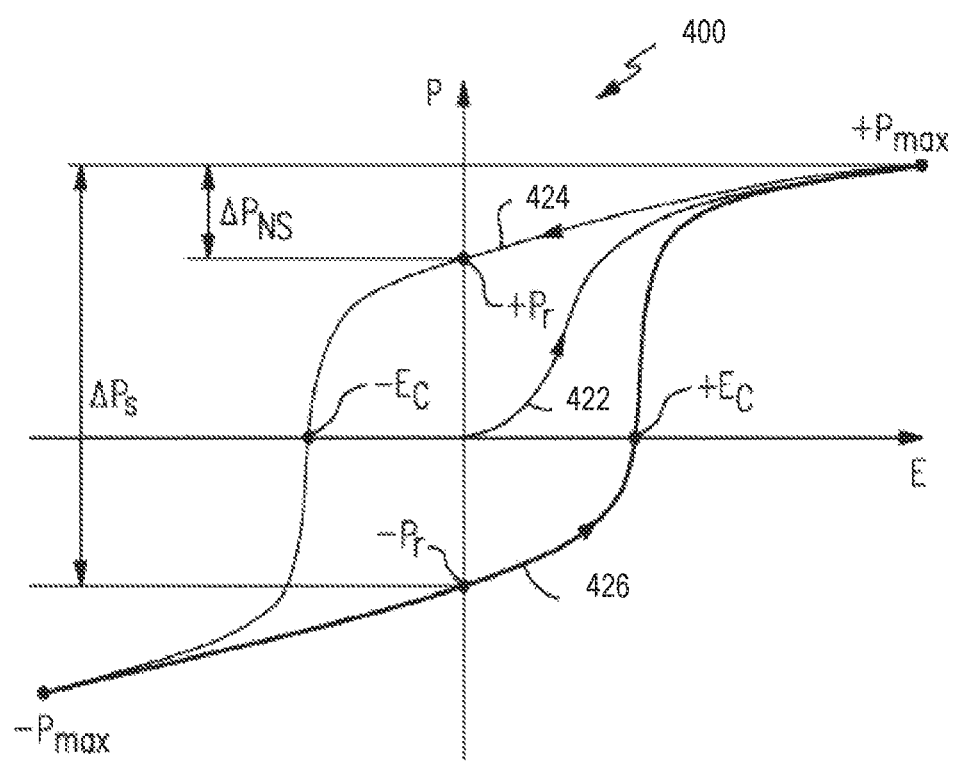
FIG. 4 illustrates a polarization vs electric field plot for a representative multi-layer stack including a non-linear polar material (e.g., ferroelectric material), in accordance with at least one embodiment.

FIG. 4 illustrates a polarization vs electric field plot (P-E loop) 400 for a representative multi-layer stack (e.g., stack 200) including a ferroelectric material in accordance with at least one embodiment. In at least one embodiment, dielectric 204 comprises a storage layer, e.g., a ferroelectric layer, paraelectric. Referring again to FIG. 4, in at least one embodiment, P-E loop 400 may represent a ferroelectric layer comprising a polydomain ferroelectric material. In at least one embodiment, prior to polarization for first time, there may initially be a statistical distribution of ferroelectric domains such that net polarization at zero field is about zero. In at least one embodiment, initial polarization (P) may be represented by P-E curve portion 422. In at least one embodiment, when ferroelectric layer is polarized for a first time by applying a positive electric field, starting with a polarization P=0, polarization increases with increasing electric field until it reaches saturation at $+P_{max}$. In at least one embodiment, after saturation is reached at $+P_{max}$, when electric field is subsequently reduced according to P-E curve portion 424, at E=0, a polarization may remain. In at least one embodiment, remaining polarization is referred to herein as a remnant polarization $(+P_r)$. In at least one embodiment, to bring polarization back to zero, a negative electric field may be applied. In at least one embodiment, a sufficient electric field for reducing polarization back to zero is referred to herein as a coercive field $(E_c)$. In at least one embodiment, according to P-E curve portion 424, a negative coercive field $(-E_c)$ may be applied to reduce polarization to zero from $+P_r$. In at least one embodiment, if negative voltage or field is further increased in magnitude, then hysteresis loop may behave similarly to that under a positive but in a reverse sense.

In at least one embodiment, negative P increases in magnitude with increasing negative electric field until it reaches saturation at $-P_{max}$. In at least one embodiment, when an electric field is subsequently reduced in magnitude along a P-E curve portion 426, at E=0, a remnant polarization $-P_r$ may remain. In at least one embodiment, ferroelectric layer exhibits a characteristic of a remnant polarization $+P_r$ or $-P_r$, which can be reversed by an applied electric field in a reverse direction. In at least one embodiment, this gives rise to a hysteretic P-E loop in ferroelectric memory devices. In at least one embodiment, by using thin film technologies, operation fields or voltages may be reduced to a level below standard chip data in a non-volatile state and allows data to be rewritten fast and frequently. In at least one embodiment, a ferroelectric memory device has advantageous features of both volatile and nonvolatile memory technologies. In at least one embodiment, voltage pulses are used to write and read digital information. In at least one embodiment, if an electric field pulse is applied in a same direction as remnant polarization, no switching may occur. In at least one embodiment, a change in polarization delta $P_{NS}$ or $\Delta P_{NS}$ between $P_{max}$ and $P_r$ may be present due to dielectric response of ferroelectric material. In at least one embodiment, if an electric field pulse is applied in an opposite direction as remnant polarization, switching may occur. In at least one embodiment, if initial polarization is in an opposite direction as applied electric field, polarization of ferroelectric layer reverses giving rise to an increased switching polarization change delta $P_s$ or $\Delta P_s$.

In at least one embodiment, P-E loop 400 can be measured in blanket stacks. In at least one embodiment, other measurements described in Table 1, below, can also be performed during an iterative development method described in association with FIGS. 1 and 3A-3B. In at least one embodiment, measurements described provide mechanical and/or chemical composition and electrical characteristics of one or more layers of a multi-layer stack such as stacks 200, 200', and 200" (See, FIGS. 1, 3A-3B). Measurement technique and associated measurement are listed in Table 1, in accordance with at least one embodiment. In at least one embodiment, for each measurement, an invoice may be generated, and billed to a customer, for service of making measurement(s).

TABLE 1

| Measurement Technique | Parameter |
|---|---|
| Transmission Electron Microscopy | Crystallinity, structure, morphology (e.g., grain size) |
| X-ray diffraction (Bragg diffraction) | Crystallinity, lattice constants, grain size, concentration gradient, strain |
| Positive Up Negative Down method | Measurement of switchable polarization vs. electric field |
| Atomic Force Microscopy (AFM), and Conductive-AFM (c-AFM) | surface roughness (AFM); current-voltage characteristics (c-AFM) |
| Picoammeter | Current-Voltage, cycling, endurance |
| Piezoelectric force microscopy | Ferroelectricity of switching layer |
| Kelvin probe force microscopy | Electrode work function |

In at least one embodiment, measurement techniques such as transmission electron microscopy may be utilized to obtain high resolution images of layers, interfaces between layers, arrangements of atoms, atomic planes, and dislocations among other things. In at least one embodiment, Xray diffraction may be utilized to measure phase identification of crystalline material in electrodes as well as in a ferroelectric dielectric layer. In at least one embodiment, positive-up and negative-down method may be utilized to measure switchable polarization versus electric field in a multi-layer stack. In at least one embodiment, Atomic Force Microscopy (AFM) may be utilized to measure surface roughness and microstructure of an uppermost layer in a stack. In at least one embodiment, conductive AFM may be utilized to measure current-voltage characteristics of multi-layer stack. In at least one embodiment, piezoelectric force microscopy may be utilized to measure ferroelectricity of ferroelectric dielectric layer. In at least one embodiment, Kelvin probe force microscopy may be utilized to measure electrode work function of electrodes in multi-layer stack. In at least one embodiment, an invoice may be generated, and billed to a customer, for service of making a measurement.

In at least one embodiment, at least some of measurements described above may be made after device fabrication. In at least one embodiment, surface roughness, especially of a lower conductive layer, may be measured after depositing a single layer at a time. In at least one embodiment, amount billed for measurement defends on complexity of measurement. In at least one embodiment, a more complex measurement is billed higher than a less complex measurement.

Figure 5:
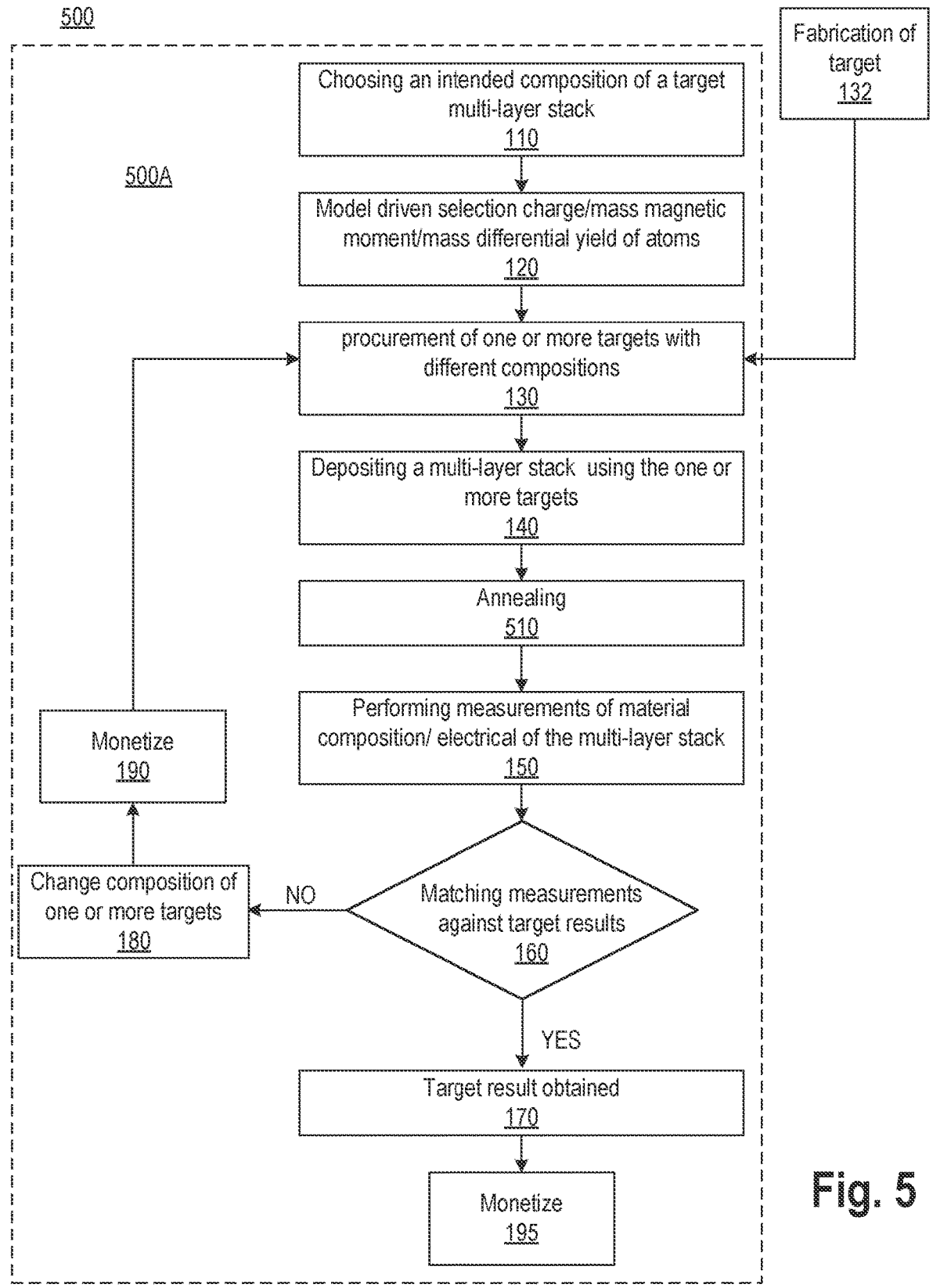
FIG. 5 illustrates a flow diagram of a method of iteratively developing a multilayer stack for application to memory devices and monetizing iterative method, where method further includes annealing multilayer stack, in accordance with at least one embodiment.

FIG. 5 illustrates a flow diagram of method 500 of iteratively developing a multilayer stack for application to memory devices and monetizing an iterative method, where method 500 further includes annealing a multilayer stack, in accordance with at least one embodiment. In at least one embodiment, method 500 includes features of method 100 (FIG. 1) with an addition of an anneal operation 510 between formation of a multi-layer stack at operation 140 and measuring material composition and performing measurements of material composition and electrical test characterization at operation 150.

In at least one embodiment, achieving a grain size that is conducive for increasing effective polarization in dielectric layer is useful for high performance memory devices. In at least one embodiment, modulation of grain size may be accomplished by performing an anneal process at high temperatures. In at least one embodiment, anneal process includes rapid thermal treatment processes (herein PD-RTA). In at least one embodiment, PD-RTA may utilize temperatures greater than or equal to 400 degrees Celsius. In at least one embodiment, blanket unpatterned stacks may be heated to high temperatures, such as temperatures above 800 degrees Celsius to determine optimal properties of a particular multi-layer stack. In at least one embodiment, anneal durations may be 10-30 minutes to test limits of multi-layer stack.

In at least one embodiment, anneal temperatures can be higher than 800 degrees Celsius, duration of most processes may be limited to approximately 1 minute or less for patterned memory devices, for example, when such memory devices are integrated with a transistor. In at least one embodiment, a process at high temperature but with a short time duration may be compatible with transistors that are embedded within substrate on which perovskite material is formed. In at least one embodiment, such a method is particularly advantageous when transistors are fabricated using a gate last process to prevent threshold voltage shifts arising from high temperature operations lasting substantially greater than 1 minute.

In at least one embodiment, a post deposition anneal (PDA) may be characterized by a thermal anneal of a layer or a stack after deposition process has been performed. In at least one embodiment, this contrasts with an in-situ anneal which takes place during deposition. In at least one embodiment, PDA may be performed after all layers in a multi-layer stack, for example, are deposited. In at least one embodiment, anneal process can be performed following a patterning process utilized to fabricate memory devices. In at least one embodiment, following deposition of a first conductive layer and a dielectric layer, anneal process can be performed prior to deposition of a second conductive layer on dielectric layer. In at least one embodiment, PDA is performed after deposition of multi-layer stack. In at least one embodiment, where anneal operation 510 is inserted prior to performing measurements of multi-layer stack, such measurements may be compared to measurements obtained from an identical unannealed multi-layer stack. In at least one embodiment, a customer may be billed, and an invoice sent, for PDA process.

In at least one embodiment, anneal temperatures can be as high as 1300 degrees Celsius, where anneal time durations are limited to less than or equal to 60 seconds. In at least one embodiment, specific temperature and time duration is dependent on annealing technique utilized and a maximum thermal budget that is compatible with, for example, a transistor for integrated device applications. In at least one embodiment, for temperatures less than 700 degrees Celsius, a time duration of 60 seconds or less, for example, may be relatively short.

In at least one embodiment, post deposition rapid thermal annealing may be used to describe all thermal annealing treatments where a wafer is heated and cooled at rates faster than is typical in furnace annealing tools. In at least one embodiment, heating and/or cooling rates can be more than 10 degrees Celsius/second. In at least one embodiment, such rapid heating and cooling can be achieved using a variety of technologies. Here, terms "RTP" or "RTA" may generally describe a rapid thermal annealing technique, in which infra-red lamps may be implemented to heat a wafer. In at least one embodiment, Xenon-lamp based heating (also called "Flash" annealing), laser heating (Laser annealing), and microwave energy (microwave annealing) may be used to heat a wafer. In at least one embodiment, surface temperatures of substrate may be monitored by pyrometer and thermocouples. In at least one embodiment, such techniques can offer extremely fast heating and cooling rates, such as for example 1 million degrees per second. In at least one embodiment, it is useful for a cooling process to be controlled to prevent dislocations in various layers.

In at least one embodiment, post deposition anneal can include one or more of above techniques. In at least one embodiment, RTP/RTA can be performed at temperatures above 1000 degrees Celsius. In at least one embodiment, since duration is on order of a minimum of a few seconds, RTP/RTA may be used for annealing to temperatures less than 800 degrees Celsius. In at least one embodiment, a customer may be billed, and an invoice sent, for RTP and/or RTA process.

In at least one embodiment, PDA includes an RTP process which is carried out in $O_2$, $N_2$, or Argon environment or in air. In at least one embodiment, processing pressures range from 1 Torr to 760 Torr while flowing in $O_2$, $N_2$, or Argon gases. In at least one embodiment, RTP process is carried out in vacuum at pressures less than 1 Torr. In at least one embodiment, processing times range from 1 s to 60 s. In at least one embodiment, processing temperatures range from 400 to 700 degrees Celsius, where heating and cooling rate is approximately 40 to 200 degrees Celsius/second.

In at least one embodiment, PDA includes a flash anneal process. In at least one embodiment, flash, and laser annealing offer extremely short durations, and thus can allow high temperatures greater than 1000 degrees Celsius without damaging underlying structures e.g., transistors on wafer. In at least one embodiment, flash and laser anneal can include spot heating or beam rastering for increased throughput. In at least one embodiment, processing pressures range from 1 Torr to 760 Torr while flowing in $O_2$, $N_2$, Argon gases, or in air. In at least one embodiment, flash anneal process is carried out in vacuum at pressures less than 1 Torr. In at least one embodiment, processing temperatures range from 500 to 1300 degrees Celsius, where heating and cooling rate is approximately 106 degrees Celsius/second. In at least one embodiment, processing times are 1 ms or less. In at least one embodiment, total anneal time can be 10 ms/flash. In at least one embodiment, total number of flashes can be up to 100 flashes per sample (wafer, substrate etc.). In at least one embodiment, a customer may be billed, and an invoice sent, for flash anneal process.

In at least one embodiment, PDA includes a laser anneal process. In at least one embodiment, processing temperatures range from 600 to 1300 degrees Celsius, where heating and cooling rate is approximately 106 degrees Celsius/second. In at least one embodiment, processing times is 100 microseconds or less. In at least one embodiment, anneal time can be 100 ms/laser anneal process. In at least one embodiment, total number of laser anneals can be up to 100 per sample (wafer, substrate etc.). In at least one embodiment, a customer may be billed, and an invoice sent, for laser anneal process.

In at least one embodiment, multi-layer stack may be deposited by a PVD process at 350 degrees Celsius, annealed by PD-RTA process in an RTP tool with a 50 degree Celsius/second heating and/or cooling rates, in $O_2$ atmosphere at 760 Torr pressure and at 600 degrees Celsius for 60 seconds. In at least one embodiment, multi-layer stack may be deposited by a PVD process at 350 degrees Celsius, annealed by PD-RTA process in a laser annealing tool with a 106 degrees Celsius/second heating and/or cooling rates, in vacuum and at 1200 degrees Celsius for 10 microseconds. In at least one embodiment, other forms of annealing include microwave annealing or hybrid microwave annealing. In at least one embodiment, a customer may be billed, and an invoice sent, for microwave annealing or hybrid microwave annealing.

In at least one embodiment, microwave anneal process comprises heating for a fourth time duration of less than 3600 s at a microwave power of less than 1000 W. Point defects such as oxygen vacancies may lead to increased electrical leakage in capacitor layers which may be detrimental to ferroelectric polarization and switching voltage. Oxygen vacancies and other point defects can also lead to ferroelectric domain-wall pinning. Pining can manifest in detrimental effects such as increased switching voltage and lead to early endurance failure of ferroelectric capacitor devices.

In at least one embodiment, dashed box 500A defines operations that are conducted by a first entity and fabrication of target at operation 132 may be carried out by a second entity such as external suppliers, where second entity is different from first entity.

In at least one embodiment, method 500 iterates by implementing a model driven selection, modifying stoichiometric composition of one or more targets in successive one or more targets, procuring successive one or more targets, and depositing a successive multi-layer stack, performing anneal, performing compositional and electrical measurements, matching measurements with target values, determining whether measurement results are within tolerance level of target values, until target results are obtained.

In at least one embodiment, after composition of one or more targets is modified (operation 180), a notification is used to a customer of method 500. In at least one embodiment, this notification may indicate that one or more targets were procured, layers were deposited on one or more targets to form a stack, and measurements were then made on stack. In at least one embodiment, notification may be electronically transmitted at operation 190 to monetize tasks listed on notification. In at least one embodiment, notification may include an invoice having a line item associated with a cost of procuring of target material and application of target material.

In at least one embodiment, in addition to making changes to composition of one or more layers in multi-layered stack, additional layers may be added to multi-layer stack at operation 140. In at least one embodiment, such layers may be formed in accordance with multi-layer stack 600 in FIG. 6. In at least one embodiment, once target result is obtained as described with reference to operation 170, method 500 may perform a monetizing operation 195. In at least one embodiment, monetizing operation 195 is like monetizing operation 190.

Figure 6:
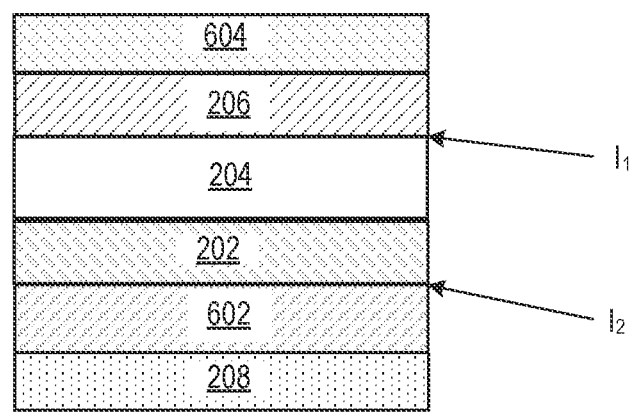
FIG. 6 illustrates a cross-sectional illustration of a multi-layer stack including a non-linear polar material (e.g., ferroelectric material), deposited in accordance with flow diagram in FIG. 1, in accordance with at least one embodiment.

FIG. 6 is a cross-sectional illustration of a multi-layer stack 600 including a ferroelectric material, deposited in accordance with flow diagram in FIG. 5, in accordance with at least one embodiment. In at least one embodiment, layers in multi-layer stack 600 are deposited by a co-sputtering or a reactive sputtering method. In at least one embodiment, a customer may be billed, and an invoice sent, for applying co-sputtering or reactive sputtering method.

In at least one embodiment, additional conductive layers 602 and 604 may implemented for different purposes. In at least one embodiment, while conductive layer 202 was previously illustrated to be deposited on substrate 208 for test purposes. In at least one embodiment, for device fabrication, conductive layer 202 may be coupled with interconnect structures. In at least one embodiment, a customer may be billed, and an invoice sent, for coupling conductive layer 202 with interconnect structures. In at least one embodiment, conductive layer 202 may also be in contact with one or more insulator layers. In at least one embodiment, a customer may be billed, and an invoice sent, for coupling conductive layer 202 with one or more insulating layers. In at least one embodiment, it may be useful for conductive layer 202 to have a crystallographic structure for templating of dielectric 204. In at least one embodiment, for this reason, among others, conductive layer 202 may be deposited on a secondary electrode layer, such as conductive layer 602. In at least one embodiment, a customer may be billed, and an invoice sent, for coupling conductive layer 202 with conductive layer 602. In at least one embodiment, conductive layer 602 includes Pt. In at least one embodiment, conductive layer 604 includes TaN. In at least one embodiment, conductive layers 602 and 604 can be deposited in-situ with non-linear polar material (e.g., ferroelectric or paraelectric material) to prevent interfacial layers $I_1$ and $I_2$ from forming between conductive layer 602 and conductive layer 202, and between conductive layer 206 and conductive layer 604, respectively. In at least one embodiment, a customer may be billed, and an invoice sent, for coupling conductive layers 602 and 604 with non-linear polar material.

In at least one embodiment, additional layers can aid some structural properties that can be overall detrimental to electrical resistance of stack. In at least one embodiment, an increase in electrical resistance can impose a need for higher operating voltages. In at least one embodiment, higher operating voltages may demand more powerful transistors. In at least one embodiment, choice of materials may add little electrical resistance while providing crystallographic templating advantages. In at least one embodiment, determining a requisite minimum thickness that can provide compositional benefits may be balanced with other parameters such as total stack thickness, case of patterning, and development of interfacial layers during device fabrication process. Iterative device development may be carefully balanced with end goals of electrical requirements. In at least one embodiment, a customer may be billed, and an invoice sent, for one or more processes of iterative device development.

In at least one embodiment, patterning of multi-layer stack to fabricate devices further introduces other complexities and iterative methods described above are used for rapid development.

Figure 7:
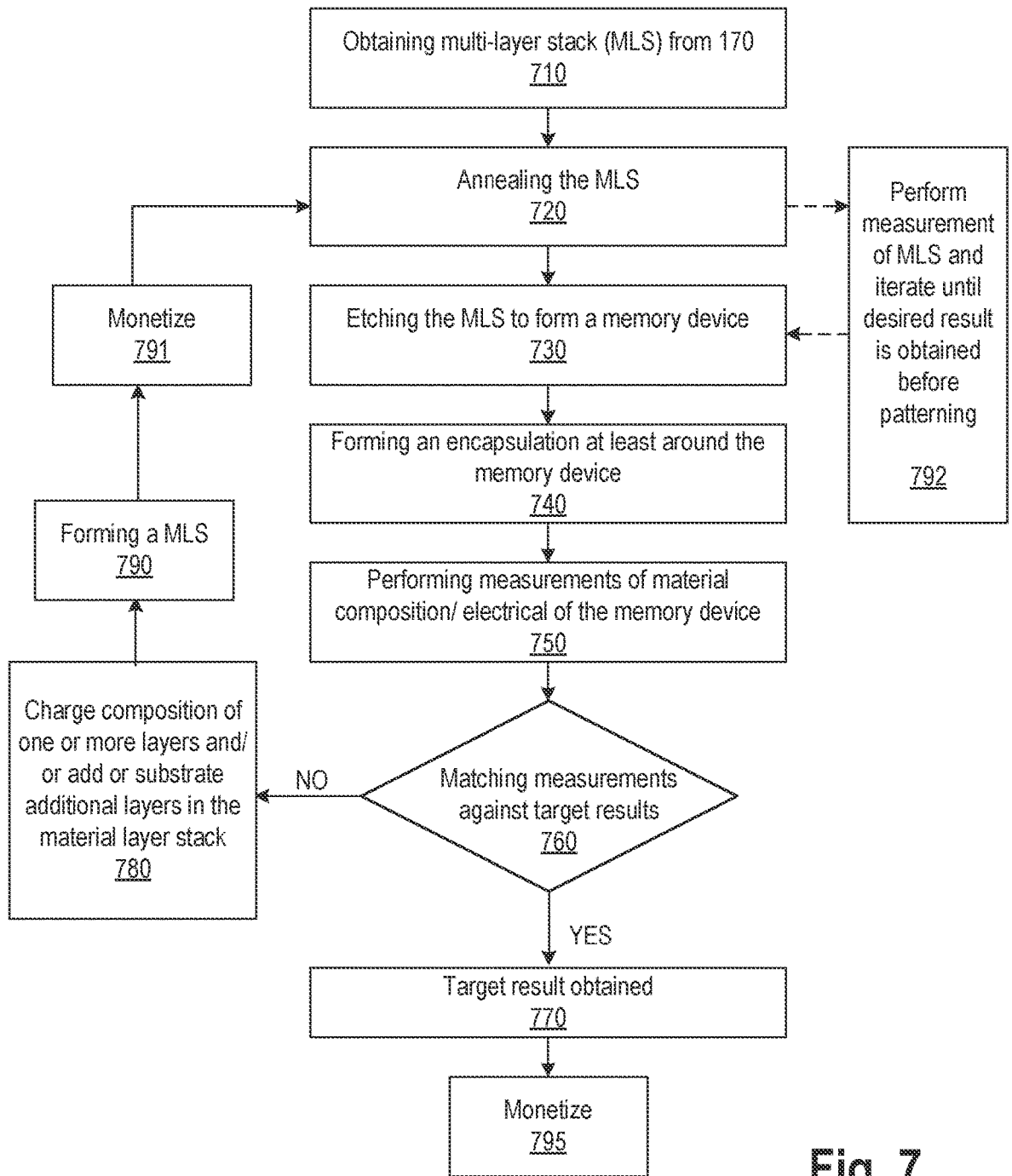
FIG. 7 illustrates a flow diagram of a method of iteratively developing a memory device and monetizing iterative method, in accordance with at least one embodiment.

FIG. 7 illustrates a flow diagram of a method 700 of iteratively developing a memory device and monetizing iterative method, in accordance with at least one embodiment. In at least one embodiment, method 700 begins at operation 710 by receiving a multi-layer stack from operation 170 (FIG. 5). In at least one embodiment, method 700 continues at operation 720 with annealing multi-layer stack. In at least one embodiment, a customer may be billed, and an invoice sent, for annealing multi-layer stack. In at least one embodiment, method 700 continues at operation 730 by etching multi-layer stack to form a memory device. In at least one embodiment, method 700 continues at operation 740 forming an encapsulation layer at least around memory device. In at least one embodiment, a customer may be billed, and an invoice sent, for forming an encapsulation layer at least around memory device. In at least one embodiment, method 700 continues at operation 750 by performing measurements of chemical composition and electrical properties of memory device. In at least one embodiment, a customer may be billed, and an invoice sent, for performing measurements of chemical composition and electrical properties of memory device.

In at least one embodiment, method 700 continues at operation 760 by matching measurements of chemical composition and electrical properties of memory device against target results and determining whether measurements are within a tolerance level of target results. In at least one embodiment, if measurements are within a tolerance level of target results (as inculcated by operation 770), a customer may be billed, and an invoice sent, for achieving target results as indicated by operation 795.

In at least one embodiment, method 700 can continue at operation 780 by making modifications in response to determining that measurements are not within tolerance level. In at least one embodiment, modifications include changing composition of one or more layers in initial multi-layer stack to form a successive multi-layer stack by implementing a model driven selection. In at least one embodiment, method 700 comprises modifying single elements or combination of elements in a successive one or more targets to comprise a respective second stoichiometric composition and procuring successive one or more targets.

In at least one embodiment, after composition of one or more targets is modified (operation 780), a notification is used to a customer of method 700. In at least one embodiment, this notification may indicate that multi-layer stack is annealed, multi-layer stack is etched, encapsulation is formed, and/or measurements made on stack.

In at least one embodiment, method 700 continues at operation 790 with forming a multi-layer stack. In at least one embodiment, method 700 iterates at operation 720 with annealing multi-layer stack, etching multi-layer stack, etching and forming a memory device, encapsulating memory device, performing measurements, matching measurements, and determining whether measurement results are within a tolerance level, until target results are obtained.

In at least one embodiment, notification may be electronically transmitted at operation 791 to monetize tasks listed on notification. In at least one embodiment, notification may include an invoice having a line item associated with a cost of changing composition of one or more layers.

In at least one embodiment, after annealing multi-layer stack, that has been deposited after a first round of iterations, measurements can be made at operation 792 after operation 720 to assess if material composition and electrical characteristics are within tolerance of a desired target. In at least one embodiment, a customer may be billed, and an invoice sent, for performing measurements. In at least one embodiment, measurements made immediately after annealing at operation 720 can save time that would otherwise be spent in continuing with fabrication of device and discovering results at end of line. In at least one embodiment, operation 792 is eliminated and measurements are made, at end of line in a fabrication sequence, after devices are fabricated.

In at least one embodiment, in addition to making changes to composition of one or more layers in multi-layered stack, additional layers may be added to multi-layer stack. In at least one embodiment, such layers may be formed in accordance with multi-layer stack 600 in FIG. 6. In at least one embodiment, a customer may be billed, and an invoice sent, for adding additional layers to multi-layer stack.

FIG. 8A illustrates a cross-sectional illustration of memory device 801 obtained by patterning multi-layer stack obtained in FIG. 7 in accordance with at least one embodiment. In at least one embodiment, memory device 801 may be a planar capacitor. In at least one embodiment, multilayer stack may have properties of stack 200' or 200" in FIGS. 3A-3B, for example, conductive layer 202, dielectric 204, and conductive layer 206. Referring again to FIG. 8A, in at least one embodiment, memory device 801 includes electrode 802, dielectric layer 804 on electrode 802, and electrode 806 on dielectric layer 804.

In at least one embodiment, electrode 802 comprises a first conductive nonlinear polar material where first conductive nonlinear polar material has a first grain size. In at least one embodiment, dielectric layer 804 comprises a perovskite material comprising a second grain size. In at least one embodiment, electrode 806 comprises a second conductive nonlinear polar material, where second conductive nonlinear polar material has a third grain size that is substantially same as first grain size or second grain size. In at least one embodiment, grain sizes are defined by an average grain length.

In at least one embodiment, perovskite film properties for high performance devices may include a grain size that is conducive for increasing effective polarization in dielectric layer. In at least one embodiment, modulation of grain size may be accomplished by performing an anneal process at high temperatures. In at least one embodiment, a customer may be billed, and an invoice sent, for modulating a grain size.

In at least one embodiment, electrode 802 includes a perovskite material. In at least one embodiment, perovskite material includes one of a non-Pb perovskite metal oxide, such as but not limited to, La—Sr—CoO$_3$, SrRuO$_3$, La—Sr—MnO$_3$, YBa$_2$Cu$_3$O$_7$, BiSr$_2$CaCu$_2$O$_8$, LaNiO$_3$, or DyScO$_3$. In at least one embodiment, electrode 802 has a nanocrystalline to polycrystalline grain structure. In at least one embodiment, grains 802A may be irregular as illustrated. In at least one embodiment, grains 802A may have a size defined by an average length $L_1$. In at least one embodiment, average length $L_1$ ranges between 15 nm and 50 nm.

In at least one embodiment, grains 806A have a size defined by an average length $L_2$. In at least one embodiment, average lengths $L_1$ and $L_2$ are substantially equal. In at least one embodiment, electrode 806 includes grains 806A that are of comparable magnitude to grains 802A of electrode 802. In at least one embodiment, average length $L_2$ ranges between 15 nm and 50 nm. In at least one embodiment, ratio $L_1:L_2$ between grain size of electrodes 802 and 806 is substantially 1:1 but can vary by less than 10% percent.

In at least one embodiment, electrode 806 can further include a same material as material of electrode 802. In at least one embodiment, substantially identical materials can provide symmetry and can offer additional advantages such as reliability as devices are cycled billions of times over a lifetime of operation. In at least one embodiment, different electrode materials having substantially same grain size can be implemented in memory device 801. In at least one embodiment, this can be advantageous in some operational regimes where at least one of electrodes 802 or 806 is coupled with an external circuit element such as a transistor.

In at least one embodiment, dielectric layer 804 has a polycrystalline grain structure. In at least one embodiment, grains 804A may be irregular as illustrated. In at least one embodiment, grains 804A have a size defined by an average length, $L_3$. In at least one embodiment, average length $L_3$ ranges between 15 nm and 50 nm. In at least one embodiment, multiple polarization domains may exist within grains 804A. In at least one embodiment, ratio between $L_1$ and $L_3$ can range between 1:3 and 3:1. In at least one embodiment, ratio between $L_1$ and $L_3$ is substantially equal to 1:1, when dielectric layer 804 includes one or more elements of electrode 802.

In at least one embodiment, while grain size is one attribute of layers within memory device 801, there are others such as point defects. In at least one embodiment, point defects are sites with missing atoms such as oxygen, or missing cations such as Ba, Bi, Fe, and/or $T_i$, etc. In at least one embodiment, point defects 803, 805, and 807 are illustrated by points within electrode 802, dielectric layer 804 and electrode 806, respectively. In at least one embodiment, point defects 803, 805, and 807 can correlate with grain size, where a layer comprising a large grain size may have lower point defect.

In at least one embodiment, electrode 802 has point defects 803 that number less than 1e20 atoms/cm$^3$. In at least one embodiment, electrode 802 has a grain size between 15 nm and 50 nm and point defects that number less than 1e20 atoms/cm$^3$. In at least one embodiment, dielectric layer 804 has point defects 805 that number less than 1e20 atoms/cm$^3$. In at least one embodiment, dielectric layer 804 has a grain size between 15 nm and 50 nm and point defects 805 that number less than 1e20 atoms/cm$^3$. In at least one embodiment, electrode 806 has a grain size between 15 nm and 50 nm and point defects 807 that number less than 1e20 atoms/cm$^3$.

In at least one embodiment, memory device 801 may be coupled with external circuit elements such as transistors through interconnect structures. In at least one embodiment, transition electrode 810 is below electrode 802. In at least one embodiment, transition electrode 810 may include a material such as TIN, W, Ru, TaN, or Ta. In at least one embodiment, transition electrode 810 can provide a surface for crystal templating of material of electrode 802.

In at least one embodiment, controlling grain sizes of electrodes and dielectric layers can modulate intrinsic behavior, which is equally useful for long term device performance to mitigate damage from extrinsic processes. In at least one embodiment, ferroelectric random-access memory (FeRAM) devices including lead-free perovskite materials may be prone to damage from reaction with hydrogen during processing. Damage may be a result of hydrogen traveling along grain boundaries between or along electrodes coupled with two terminals of a FeRAM device. Hydrogen can cause reduction when it reacts with one or more materials of FeRAM device, such as electrodes or ferroelectric or paraelectric material itself. During fabrication anneal operations carried to tie up dangling bonds can be sources of hydrogen. FeRAM devices can lose their polarization hysteresis characteristics because of hydrogen reduction.

In at least one embodiment, where memory device 801 has a planar structure where individual layers are sequentially layered, one on top of another, it is useful to protect capacitor sidewalls, top and bottom surfaces from reacting with hydrogen. In at least one embodiment, solutions against hydrogen diffusion include forming an insulating barrier layer, for example, silicon nitride, to protect sidewalls and top surfaces. In at least one embodiment, a customer may be billed, and an invoice sent, for forming an insulating barrier layer to protect against hydrogen diffusion. In at least one embodiment, a contact electrode may be formed on top of memory device 801 by etching through insulating barrier layer and exposing electrode 806. In at least one embodiment, a customer may be billed, and an invoice sent, for forming a contact on top of memory device 801.

FIG. 8B illustrates a cross-sectional illustration of a plurality of memory devices 820, where individual devices 801 are at least laterally surrounded by encapsulation layer 812, in accordance with at least one embodiment. In at least one embodiment, to prevent hydrogen from reaching dielectric layer 804, memory device 801 may be, at least laterally covered by encapsulation layer 812. In at least one embodiment, sidewall 813 of memory device 801 is laterally surrounded by encapsulation layer 812. In at least one embodiment, encapsulation layer 812 also extends partially on an uppermost surface of memory device 801 (x and y being respectively x-axis and z-axis of plurality of memory devices 820).

In at least one embodiment, process utilized to deposit encapsulation layer 812 can depend on materials utilized, and on a height of memory device 801. In at least one embodiment, which includes a plurality of memory devices, deposition process can be dependent on relative spacing Sp, between adjacent memory devices. In at least one embodiment, deposition process utilized to deposit encapsulation layer 812 may not include hydrogen or an ammonia containing chemicals to prevent hydrogen exposure to layers within memory device 801. In at least one embodiment, encapsulation layer 812 is blanket deposited. In at least one embodiment, a customer may be billed, and an invoice sent, for depositing encapsulation layer 812.

In at least one embodiment, encapsulation layer 812 includes an insulator material. In at least one embodiment, insulator material can include a metal and oxygen, such as, but not limited to $Al_xO_y$, $HfO_x$, $AlSiO_x$, $ZrO_x$, or $TiO_x$. In at least one embodiment, materials such as $Al_xO_y$, $HfO_x$, $AlSiO_x$, $ZrO_x$, or $TiO_x$ can be deposited without a hydrogen or ammonia containing chemical precursor in an Atomic Layer Deposition (ALD) process. In at least one embodiment, encapsulation layer 812 may be deposited to a thickness in a range of 0.5 nm to 10 nm. In at least one embodiment, encapsulation layer 812 may be deposited to a thickness of less than 5 nm. In at least one embodiment, an ALD process can provide a substantially conformal thickness on sidewalls of memory device 801. In at least one embodiment, a PVD deposition process may not conformally deposit encapsulation layer 812 with a uniform thickness.

In at least one embodiment, a PVD process may be utilized. In at least one embodiment, encapsulation layer 812 can include materials such as compounds of nitrogen and a transition metal such as, but not limited to AlN, ZrN, HfN, or compounds of Si and O and one or more of Al, Hf, or Ta, such as, but not limited to, $AlSiO_x$, $HfSiO_x$, and $TaSiO_x$. In at least one embodiment, a PVD process may not provide a substantially conformal deposition on sidewalls of memory device 801. In at least one embodiment, a thickness of approximately 2 nm may be sufficient to prevent hydrogen transport through encapsulation layer 812 that is deposited with a material density of at least 90%.

In at least one embodiment, material of encapsulation layer 812 can be chosen based on material of dielectric layer 804. In at least one embodiment, pairing encapsulation layer 812 with dielectric layer 804 can minimize lattice dislocations that can cause voids and potential pathways for hydrogen diffusion.

In at least one embodiment, hydrogen may diffuse to electrodes 806 and 802 through one or more materials of a contact electrode and transition electrode 810 respectively. In at least one embodiment, to protect against hydrogen diffusion through a top surface of electrode 806, noble metals can be implemented on electrode 806.

In at least one embodiment, hydrogen can also diffuse from layers below electrode 802. In at least one embodiment, electrode 802 may be physically isolated from a conductive interconnect by transition electrode 810. In at least one embodiment, transition electrode 810 may be laterally surrounded by insulator layer 808 that can act as a barrier against hydrogen diffusion as well as provide etch stop capability while patterning to form memory device 801.

In at least one embodiment, to prevent hydrogen from diffusing directly into sidewalls of transition electrode 810, an insulator including an amorphous material, may be directly in contact with sidewalls of transition electrode. In at least one embodiment, an amorphous material may have a high film density (for example, a film density above 90% of theoretical material density or film density).

In at least one embodiment, an iterative method described above may be useful for choosing a type of material for encapsulation layer 812 as well as for understanding which deposition technique to adopt. In at least one embodiment, a customer may be billed, and an invoice sent, applying an iterative method for selecting a type of material for encapsulation layer 812.

In at least one embodiment, dielectric 204 can dictate choice of encapsulation layer 812. In at least one embodiment, encapsulation layer 812 may be chosen to have a Young's modulus similar to a Young's modulus of dielectric 204. In at least one embodiment, encapsulation layer 812 may be chosen to have a low probability of presence of defects at interface between encapsulation layer 812 and dielectric 204. In at least one embodiment, encapsulation layer 812 can have a lower dielectric constant than dielectric constant of dielectric 204 to enable field lines to be concentrated between conductive layer 202 and conductive layer 206.

In at least one embodiment, where dielectric 204 includes a $Pb_xZr_{1-x}Ti_yO_3$ group of families, encapsulation layer 812 can include $Al_xO_y$, $HfO_x$, $ZrO_x$, $TaO_x$, or $TiO_x$. In at least one embodiment, where dielectric 204 includes a $La_xBi_{1-x}Fe_yO_3$ group of families, encapsulation layer 812 can include $Al_xO_y$, $HfO_x$, $ZrO_x$, $TaO_x$, or $TiO_x$. In at least one embodiment, where dielectric 204 includes a $BaTiO_3$ group of families, encapsulation layer 812 can include $Al_xO_y$, $HfO_x$, $ZrO_x$, $TaO_x$, or $TiO_x$. In at least one embodiment, where dielectric 204 includes a $BiFeO_3$ group of families, encapsulation layer 812 can include $Al_xO_y$, $HfO_x$, $ZrO_x$, $TaO_x$, or $TiO_x$.

Figure 9:
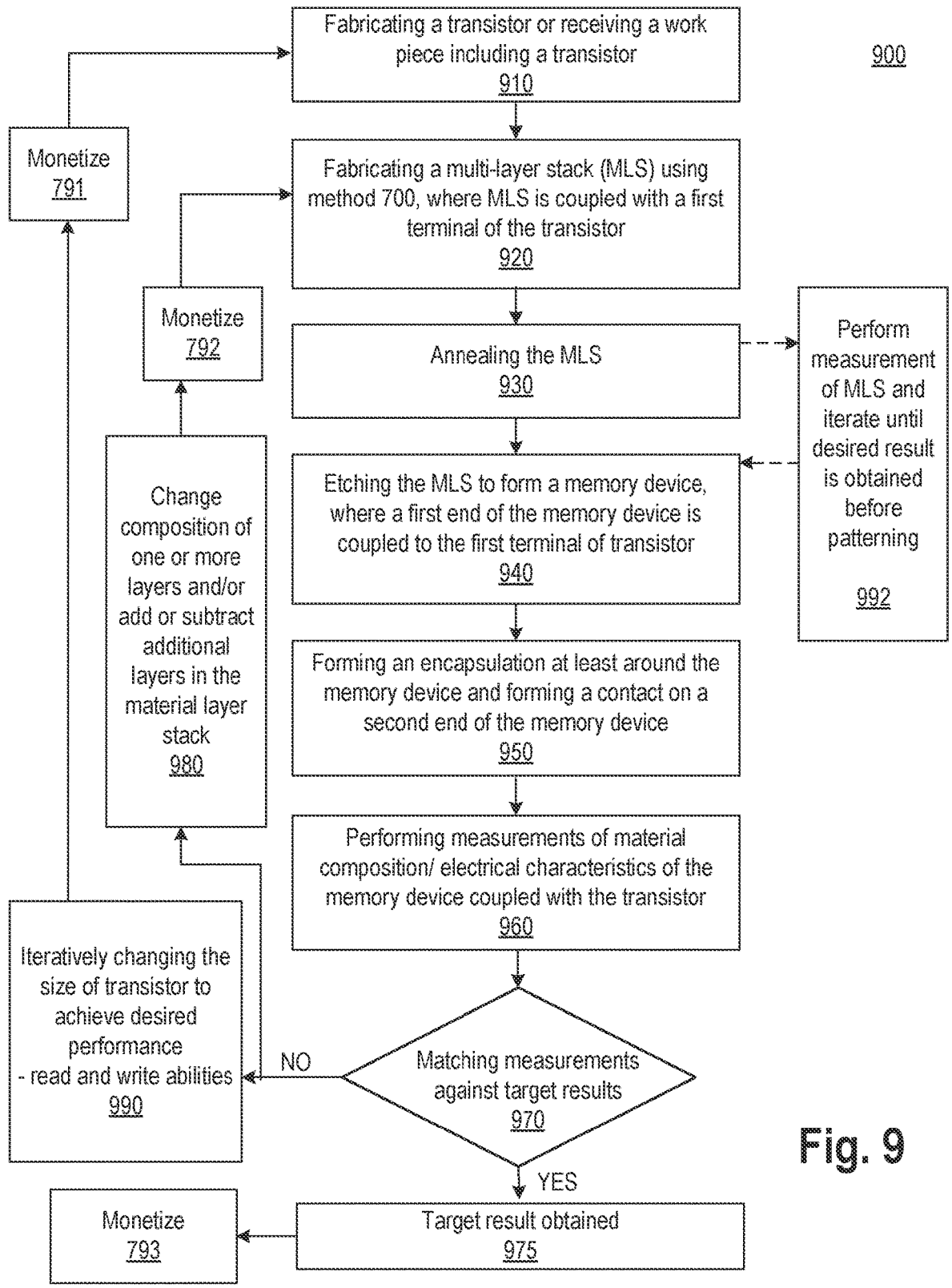
FIG. 9 illustrates a flow diagram of a method to iteratively developing a memory device coupled with a transistor and monetizing an iterative method, in accordance with at least one embodiment.

FIG. 9 illustrates a flow diagram of a method 900 to iteratively developing a memory device coupled with a transistor and monetizing iterative method, in accordance with at least one embodiment. In at least one embodiment, method 900 begins at operation 910 by fabricating a transistor or receiving a workpiece that includes a transistor (for example purchased from a third party). In at least one embodiment, a customer may be billed, and an invoice sent, for acquiring a transistor wafer from a vendor, where transistor wafer may include one or more transistors. In at least one embodiment, a customer may be billed, and an invoice sent, for fabricating transistor or receiving workpiece that includes transistor.

In at least one embodiment, method 900 continues at operation 920 by fabricating a multi-layer stack using method 900 described in association with FIG. 7. Referring again to FIG. 9, multi-layer stack is coupled with a first terminal of transistor. In at least one embodiment, a customer may be billed, and an invoice sent, for coupling transistor to multi-layer stack. In at least one embodiment, method 900 continues at operation 930 by annealing multi-layer stack. In at least one embodiment, a customer may be billed, and an invoice sent, for annealing multi-layer stack. In at least one embodiment, method 900 continues at operation 940 by etching multi-layer stack to form a memory device, where a first terminal of memory device is coupled with first terminal of transistor. In at least one embodiment, method 900 continues at operation 950 by forming an encapsulation at least around memory device and forming a contact on a second end of memory device. In at least one embodiment, a customer may be billed, and an invoice sent, for etching multi-layer stack to form memory device. In at least one embodiment, second terminal is above first terminal. In at least one embodiment, method 900 continues at operation 960 by performing measurements of chemical composition and electrical properties of memory device coupled with transistor. In at least one embodiment, a customer may be billed, and an invoice sent, for performing measurements. In at least one embodiment, method 900 continues at operation 970 by matching measurements of compositional and electrical characterization of memory device coupled with transistor against target results for a reference memory device coupled with a reference transistor.

In at least one embodiment, at operation 975 target results are provided which are within tolerance level. In at least one embodiment, a customer may be billed, and an invoice sent, for providing target result as indicated by monetization operation 793. In at least one embodiment, if, after matching measurements against target results, measurements are not within a tolerance level of target results, method 900 continues at operation 980 by making modifications in response to determining that measurements are not within tolerance level. In at least one embodiment, modifications include changing composition of one or more layers in initial multi-layer stack to form a successive multi-layer stack by implementing a model driven selection, modifying single elements or combination of elements in a successive one or more targets to comprise a respective second stoichiometric composition, and procuring successive one or more targets. In at least one embodiment, one or more additional layers can be added or removed from successive multi-layer stack. In at least one embodiment, a customer may be billed, and an invoice sent, for modifying composition of one or more layers in initial multi-layer stack to form a successive multi-layer stack.

In at least one embodiment, method 900 iterates at operation 920 with fabricating a successive multi-layer stack, annealing successive multi-layer stack, etching successive multi-layer stack, etching and forming a memory device, encapsulating memory device, performing measurements, matching measurements, determining whether measurement results are within tolerance level, and repeating until target results are obtained. In at least one embodiment, a customer may be billed, and an invoice sent, for preforming any of repeated operations of 920, 930, 940, 950, 960, 970, and 980.

In at least one embodiment, method 900 continues at operation 990 by changing size of transistor to achieve a desired performance. In at least one embodiment, transistor characteristics to be changed include saturation current, operational voltage, gate voltage and physical dimensions. In at least one embodiment, a customer may be billed, and an invoice sent, for changing size of transistor as indicated by monetizing operation 791. In at least one embodiment, transistor may be fabricated or purchased from a third party.

In at least one embodiment, after annealing multi-layer stack that has been deposited after a first round of iterations, measurements can be made at operation 992 to assess if material composition and electrical characteristics are within tolerance of a desired target. In at least one embodiment, a customer may be billed, and an invoice sent, for performing measurements of multi-layer stack. In at least one embodiment, measurements made after annealing can save time that would be spent in continuing with fabrication of device. In at least one embodiment, operation 992 can be eliminated and measurements are made after devices are fabricated.

Figure 10:
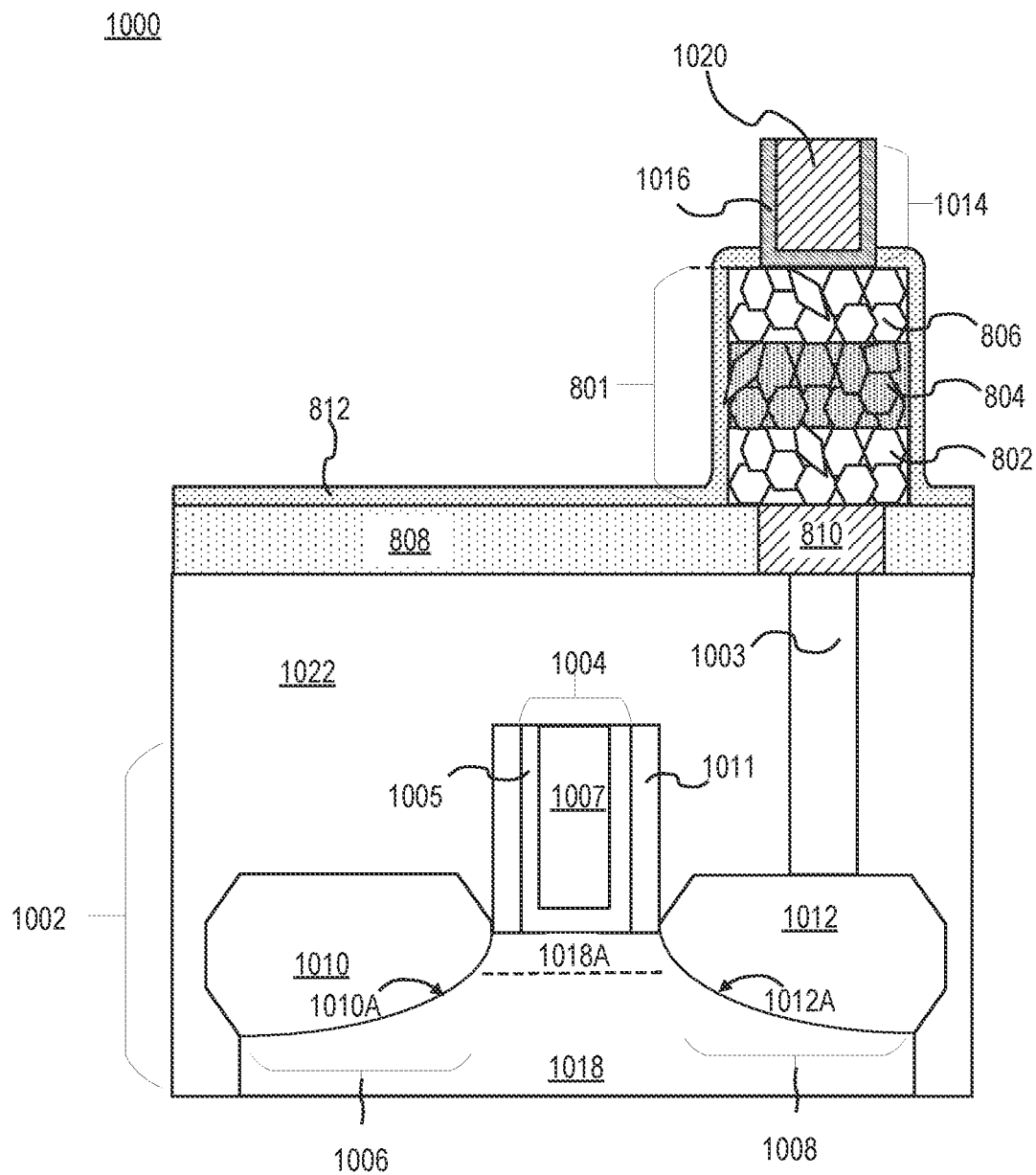
FIG. 10 illustrates a cross-sectional illustration of a 1T-1C transistor device, in accordance with at least one embodiment.

FIG. 10 illustrates a cross-sectional illustration of a 1T-1C transistor device 1000, in accordance with at least one embodiment. In at least one embodiment, 1T-1C (one transistor, one capacitor) transistor device 1000 includes memory device 801 and transistor 1002. In at least one embodiment, memory device 801 is coupled to transistor 1002 through drain contact 1003. In at least one embodiment, memory device 801 includes one or more features of memory device 801 (FIG. 8A). In at least one embodiment, memory device 801 is on a transition electrode 810. In at least one embodiment, transition electrode 810 is coupled with a drain contact 1003 of transistor 1002.

In at least one embodiment, memory device 801 can be a planar capacitor (FIG. 8A) or a trench capacitor In at least one embodiment, memory device 801 have a cylindrical profile. In at least one embodiment, memory device 801 can have a rectangular profile. In at least one embodiment, while memory device 801 is electrically coupled with drain contact 1003, there may be intervening layers of via electrodes between drain contact 1003 and transition electrode 810.

In at least one embodiment, transistor 1002 is an example of a transistor that is non-planar. In at least one embodiment, transistor 1002 may be, for example, an n-type transistor (e.g., NMOS transistor) or a p-type transistor (e.g., PMOS transistor). In at least one embodiment, transistor 1002 includes gate structure 1004, between source region 1006 and drain region 1008. In at least one embodiment, source region 1006 includes epitaxial source structure 1010 (herein source structure 1010) and drain region 1008 includes epitaxial drain structure 1012 (herein drain structure 1012). In at least one embodiment, source structure 1010 and drain structure 1012 are separated from gate structure 1004 by spacer 1011 and have faceted sidewall surfaces 1010A and 1012A. Not all faceted surfaces of source structure 1010 and drain structure 1012 are shown. In at least one embodiment, a portion of gate structure 1004 is on dielectric 1022 that separates gate structure 1004 from substrate 1018. In at least one embodiment, drain contact 1003 is coupled to drain structure 1012.

In at least one embodiment, gate structure 1004 further includes gate dielectric layer 1005 and gate electrode 1007. In at least one embodiment, gate dielectric layer 1005 has a base portion on channel 1018A and sidewall portions that are adjacent to spacer 1011. In at least one embodiment, gate electrode 1007 is confined within gate dielectric layer 1005.

In at least one embodiment, gate dielectric layer 1005 includes a suitable gate dielectric material such as but not limited to an oxide of one or more of Si, Hf, Zr, La, Ti, Ta, or Ga; or Al, such as $SiO_2$, $HfO_2$, $ZrO_2$, $HfSiO_x$, $HfZrO_2$, $Ta_2O_5$, $Al_2O_3$, $La_2O_3$, $TaSiO_x$; or $Ga_2O_5$. In at least one embodiment, gate electrode 1007 may include one or more of Ti, Al, W, Pt, Co, Ni, or Pd; nitrogen; one or more of Ti, Ta, Al, Hf, or Zr; or carbon and one or more of Ti, Al, Ta, Hf, or Zr. In at least one embodiment, source structure 1010 and drain structure 1012 may include amorphous Si, SiC, SiGe, or Ge and may be doped with As, P, or B, depending on mobile charge carrier implemented. In at least one embodiment, spacer 1011 includes silicon nitride or silicon nitride doped with carbon. In at least one embodiment, drain contact 1003 includes a conductive material such as Ru, Ti, Co, Mo, Co, Ni, W, or Ta; or nitrides of $T_i$, W, or Ta. In at least one embodiment, drain contact 1003 includes a liner layer including TiN, TaN, or WN; and a fill metal including one or more of Ru, Ti, Co, Mo, Co, Ni, W, or Ta.

In at least one embodiment, memory device 801 may be further coupled with a contact structure 1014. In at least one embodiment, contact structure 1014 is coupled with electrode 806. In at least one embodiment, contact structure 1014 may include a conductive hydrogen barrier 1016 that surrounds a fill material 1020. In at least one embodiment, conductive hydrogen barrier 1016 is in contact with encapsulation layer 812. In at least one embodiment, encapsulation layer 812 and conductive hydrogen barrier 1016 together provide a barrier to memory device 801.

In at least one embodiment, conductive hydrogen barrier 1016 includes a material that is amorphous. In at least one embodiment, amorphous materials lack defined grain boundaries that can facilitate hydrogen diffusion and are thus desirable. In at least one embodiment, conductive hydrogen barrier 1016 includes materials such as, but not limited to: TiAlN, with >30 atomic percent AlN; TaN, with >30 atomic percent $N_2$; TiSiN, with >20 atomic percent SiN; Ta carbide, TaC, or $T_i$ carbide; TiC; tungsten carbide; WC; tungsten nitride; WN; carbonitrides of Ta, $T_i$, or W, e.g., TaCN, TiCN, or WCN; titanium monoxide; TiO; $Ti_2O$; Tungsten oxide; $WO_3$ or Tin oxide; $SnO_2$; indium tin oxide; ITO; Iridium Oxide; Indium Gallium Zinc Oxide; IGZO; Zinc Oxide, or METGLAS series of alloys, e.g., $Fe_{40}Ni_{40}P_{14}B_6$. In at least one embodiment, conductive hydrogen barrier 1016 has a thickness that is less than 5 nm.

In at least one embodiment, transition electrode 810 includes a material that provides a barrier against hydrogen and oxygen diffusion. In at least one embodiment, transition electrode 810 may not include a material that provides a barrier against hydrogen and oxygen diffusion. In at least one embodiment, transition electrode can be laterally surrounded by a conductive hydrogen barrier layer such as conductive hydrogen barrier 1016.

In at least one embodiment, encapsulation layer 812 can include materials that are oxygen diffusion barriers. Examples of oxygen diffusion barrier material includes silicon nitride and silicon carbide.

In at least one embodiment, iterative method described in FIG. 9, may be utilized to determine choice of materials for encapsulation layer 812, conductive hydrogen barrier 1016, optimization of drive current, threshold voltage, and/or on-off characteristics (among other parameters) of transistor 1002. In at least one embodiment, any of process discussed in FIG. 10 can be billed to a customer.

Figure 11:
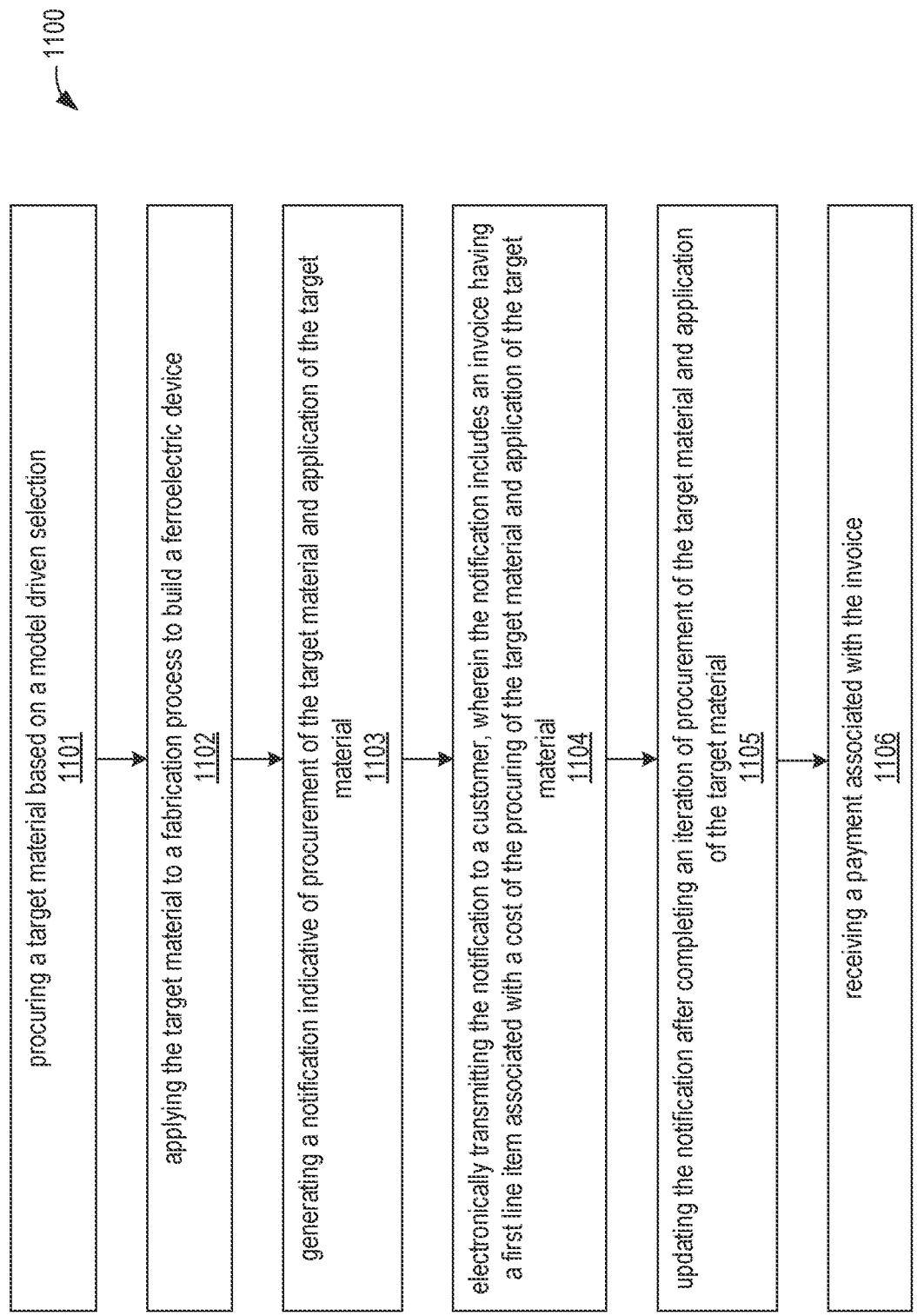
FIG. 11 illustrates a flowchart of iterative monetizing of target material as it is used for development of a device, in accordance with at least one embodiment.

FIG. 11 illustrates flowchart 1100 of iterative monetizing of target material as it is used for development of a device, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1101, a target material may be procured. In at least one embodiment, target material may be procured based on a model driven selection which is based on charge, mass and magnetic moment, and/or mass of atomic constituents of target material. In at least one embodiment, target material may be procured based on any preference. In at least one embodiment, target material may be procured based on intuition of an expert in this art. In at least one embodiment, target material comprises PVD target material. In at least one embodiment, target material comprises ALD material. In at least one embodiment, target material includes chemical vapor deposition (CVD) material. In at least one embodiment, target material may include any combination of PVD material, ALD material, or CVD material. In at least one embodiment, target material comprises lead zirconium titanate (PZT), or PZT with a doping material, wherein doping material is one of La, Nb, Sc, Ti, V, Cr, Mn, Fe, Co, Ni, Cu, or Zn. In at least one embodiment, doping material includes materials from 3d series of periodic table.

In at least one embodiment, target material comprises a relaxor ferroelectric material which includes one of lead magnesium niobate (PMN), lead magnesium niobate-lead titanate (PMN-PT), lead lanthanum zirconate titanate (PLZT), lead scandium niobate (PSN), barium titanium-bismuth zinc niobium tantalum (BT-BZNT), or Barium titanium-barium strontium titanium (BT-BST).

In at least one embodiment, target material comprises a perovskite material which includes one of: $BaTiO_3$, $PbTiO_3$, $KNbO_3$, or $NaTaO_3$. In at least one embodiment, target material comprises Bismuth ferrite (BFO). In at least one embodiment, target material comprises Barium titanate (BTO). In at least one embodiment, target material comprises BFO doped with one of: Sc. Ti, V, Cr, Mn, Fe, Co, Ni, Cu, or Zn. In at least one embodiment, target material comprises BTO doped with one of: Sc. Ti, V, Cr, Mn, Fe, Co, Ni, Cu, or Zn. In at least one embodiment, target material comprises bismuth ferrite (BFO) with a doping material, wherein doping material is one of lanthanum, elements from lanthanide series of a periodic table, or elements of a 3d, 4d, 5d, 6d, 4f, or 5f series of periodic table. In at least one embodiment, target material includes $La_xBi_yFeO_z$ (LBFO) film that can be epitaxially grown on a 0.7 weight % Nb-doped $SrTiO_3$ (001) single-crystal substrate. In at least one embodiment, x is substantially equal to 0.1, y is substantially equal to 0.9, and z is substantially equal to 3 for $La_xBi_yFeO_z$ (LBFO). In at least one embodiment, LBFO is doped with a doping material. In at least one embodiment, doping material for LBFO includes Mn.

In at least one embodiment, target material comprises hexagonal ferroelectric which includes one of: $YMnO_3$ or $LuFcO_3$. In at least one embodiment, target material comprises hexagonal ferroelectrics of a type $h-RMnO_3$, wherein R is a rare earth element which includes one of: cerium (Ce), dysprosium (Dy), erbium (Er), europium (Eu), gadolinium (Gd), holmium (Ho), lanthanum (La), lutetium (Lu), neodymium (Nd), prascodymium ($P_r$), promethium (Pm), samarium (Sm), scandium (Sc), terbium (Tb), thulium (Tm), ytterbium (Yb), or yttrium (Y); hafnium (Hf), zirconium (Zr), aluminum (Al), silicon (Si), their oxides or their alloyed oxides. In at least one embodiment, target material comprises Hafnium oxides as $Hf1-x Ex O_y$, where E can be Al, Ca, Ce, Dy, Er, Gd, Ge, La, Sc. Si, Sr, Sn, Zr, or Y; $Al(1-x)Sc(x)N$, $Ga_{(1-x)}Sc_{(x)}N$, $Al_{(1-x)}Y_{(x)}N$ or $Al_{(1-x-y)}Mg_{(x)}Nb_{(y)}N$, $E_y$ doped $HfO_2$, where x includes one of: Al, Ca, Ce, Dy, Er, Gd, Ge, La, Sc, Si, Sr, Sn, or Y, wherein 'x' or 'y' is a fraction; or niobate type compounds $LiNbO_3$, $LiTaO_3$, lithium iron tantalum oxyfluoride, barium strontium niobate, sodium barium niobate, or potassium strontium niobate. In at least one embodiment, target material comprises an improper ferroelectric material which includes one of: [PTO/STO]n or [LAO/STO]n, wherein 'n' is between 1 and 100, or a paraelectric material that comprises $SrTiO_3$, $Ba_{(x)}Sr_{(y)}TiO_3$, $HfZrO_2$, Hf—Si—O, La-substituted $PbTiO_3$, or a PMN-PT based relaxor ferroelectrics.

In at least one embodiment, at operation 1102, target material may be applied to a fabrication process to build a device having non-linear polar material (e.g., ferroelectric material, paraelectric material, or non-linear dielectric). In at least one embodiment, fabrication process can be any processes described herein.

In at least one embodiment, at operation 1103, a notification may be generated indicative of procurement of target material and application of target material. In at least one embodiment, at operation 1104, notification is electronically transmitted to a customer. In at least one embodiment, electronic transmission may be in a form of an email, facsimile, or a digital image. In at least one embodiment, notification may include an invoice having a first line item associated with a cost of procuring of target material and application of target material. In at least one embodiment, invoice is one of: a bill of sale, an estimate cost, royalty, equity share, or cost-plus estimate.

In at least one embodiment, at operation 1105, notification is updated after completing an iteration of procurement of target material and application of target material. In at least one embodiment, payment associated with invoice is received. In at least one embodiment, payment may be received in any form. In at least one embodiment, at operation 1106, payment may be received electronically, as cash, as a credit, as a credit card, as a bitcoin or any other cryptocurrency.

Figure 12:
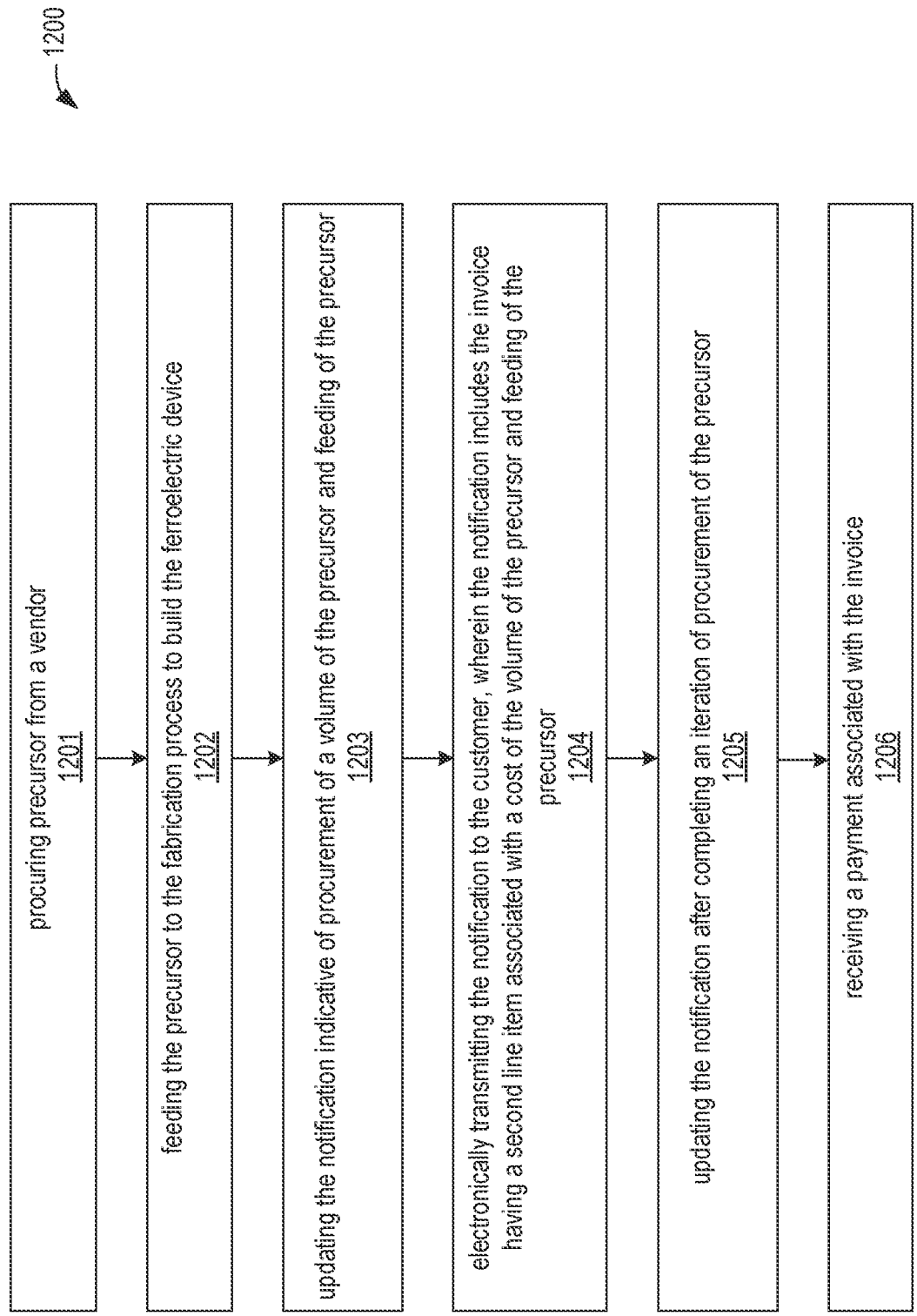
FIG. 12 illustrates a flowchart of iterative monetizing of precursor as it is used for development of a device, in accordance with at least one embodiment.

FIG. 12 illustrates flowchart 1200 of iterative monetizing of precursor as it is used for development of a device, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1201, a precursor is procured from a vendor. In at least one embodiment, precursor includes trimethysilane (3MS) gas for low-K dielectric and low-K diffusion barriers with copper interconnects, as well as for etch hard masks. In at least one embodiment, precursor includes tetramethylsilane (4MS) precursors for low-K barrier films; etch hard masks; and carbon-doped silicon films and silicon carbide-like films. In at least one embodiment, precursors include Hexachlorodisilane (HCDS) precursors for conformal silicon oxide and silicon nitride applications throughout ALD process. In at least one embodiment, HCDS precursors available in both chemical and electronic grade products. In at least one embodiment, precursor includes silicon precursor such as Tetraethylorthosilicate. In at least one embodiment, precursor includes Titaniumtetrachloride. In at least one embodiment, precursor includes Tris(dimethylamino)silane. In at least one embodiment, precursor includes Tris(trimethylgermyl)arsine. In at least one embodiment, precursor includes Tetrakisdimethylamidotitanium. In at least one embodiment, precursor includes chemicals from group III/V and II/VI. In at least one embodiment, precursor includes Trimethylgallium, Triethylgallium, Trimethylindium, Trimethylaluminum, Tertiarybutylarsine, Tertiarybutylphosphine, Dimethylhydrazine, Tetrabromomethane, and/or Diethyltelluride. In at least one embodiment, precursor includes two-dimensional (2D) materials. In at least one embodiment, precursor includes molybdenumhexacarbonyl (Mo(CO)6), tungstenhexacarbonyl (W(CO)6), Diisopropylselenide (DiPSe), bis-tert-butyliminobisdimethylaminowolframvi (BTMW), Bis(tert-butylimido)bis(dimethylamido)molybdenum (BTMMo), Diethyltelluride (DETe), and/or Methylallyltelluride (MATe). In at least one embodiment, precursors include Tris(cyclopentadienyl)scandium (Cp3Sc) and/or trimethylmethylcyclopentadienylplatinumiv (MeCpPtMe3).

In at least one embodiment, at operation 1202, precursor is fed to fabrication process to build a device (e.g., ferroelectric device, paraelectric device, non-linear dielectric device, and/or magnetic tunneling junction, etc.). In at least one embodiment, at operation 1203, notification is updated or a new notification is generated indicative of procurement of a volume of precursor and/or feeding of precursor. In at least one embodiment, at operation 1204, notification is electronically transmitted to a customer. In at least one embodiment, notification includes an invoice having a line item associated with a cost of volume of precursor and/or feeding of precursor. In at least one embodiment, at operation 1205, notification is updated after completing an iteration of procurement of precursor and/or feeding of precursor. In at least one embodiment, payment associated with invoice is received. In at least one embodiment, at operation 1206, payment may be received in any form. In at least one embodiment, payment may be received electronically, as cash, as a credit, as a credit card, as a bitcoin or any other cryptocurrency.

Figure 13:
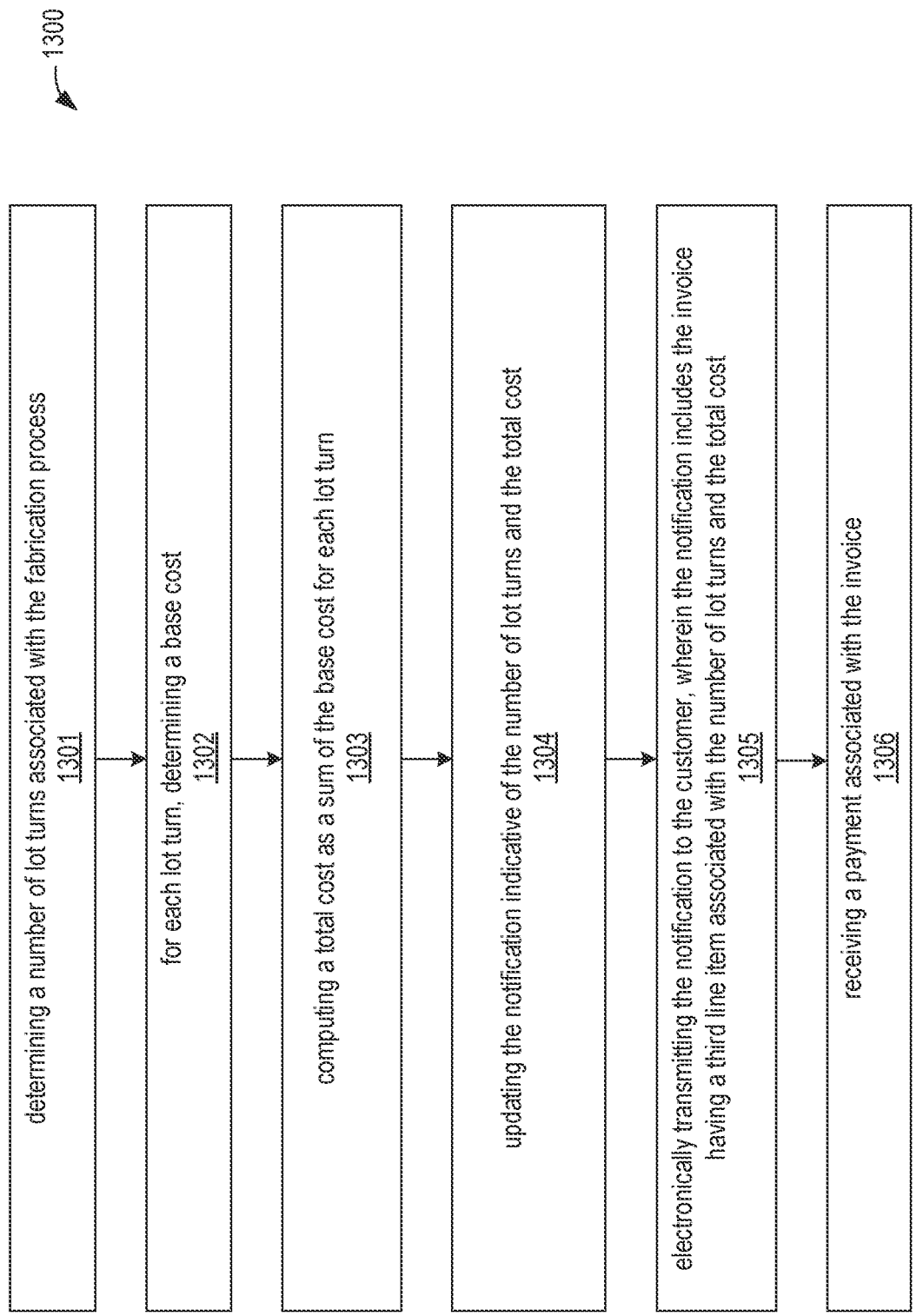
FIG. 13 illustrates a flowchart of iterative monetizing of number of turns as it is used for development of a device, in accordance with at least one embodiment.

FIG. 13 illustrates flowchart 1300 of iterative monetizing of a number of turns as it is used for development of a device, in accordance with at least one embodiment. While various operations are shown in a particular order, order or operations can be modified. For example, some operations can be performed before others in a different iteration. Some operations blocks described herein can be performed by hardware, software, manually, or a combination of them.

In at least one embodiment, at operation 1301, number of lot turns are determined associated with a fabrication process. In at least one embodiment, lot turn indicates a wafer being processed by one or more machines, wherein number of lot turns indicates number of operations performed on wafer by one or more machines. In at least one embodiment, number of operations includes an operation that results in a change in structure of a device (e.g., ferroelectric device, paraelectric device, and/or non-linear dielectric. In at least one embodiment, number of operations includes an operation that results in a change in composition of a material of device. In at least one embodiment, number of operations includes an operation that results in a change in granularity of a material of device. In at least one embodiment, number of operations includes an operation that results in a change crystalline orientation of a material of device. In at least one embodiment, number of operations includes an operation that results in a change in thermodynamics of a material of device.

In at least one embodiment, at operation 1302, for each lot turn, a base cost is determined. In at least one embodiment, at operation 1303, a total cost as a sum of base cost for each lot turn may be computed. In at least one embodiment, at operation 1304, notification indicative of number of lot turns and total cost may be updated or a new notification initiative may be generated. In at least one embodiment, at operation 1305, notification is electronically transmitted to a customer. In at least one embodiment, notification includes an invoice having a line item associated with number of lot turns and total cost. In at least one embodiment, payment associated with invoice is received. In at least one embodiment, at operation 1306, payment may be received in any form. In at least one embodiment, payment may be received electronically, as cash, as a credit, as a credit card, as a bitcoin or any other cryptocurrency.

Figure 14:
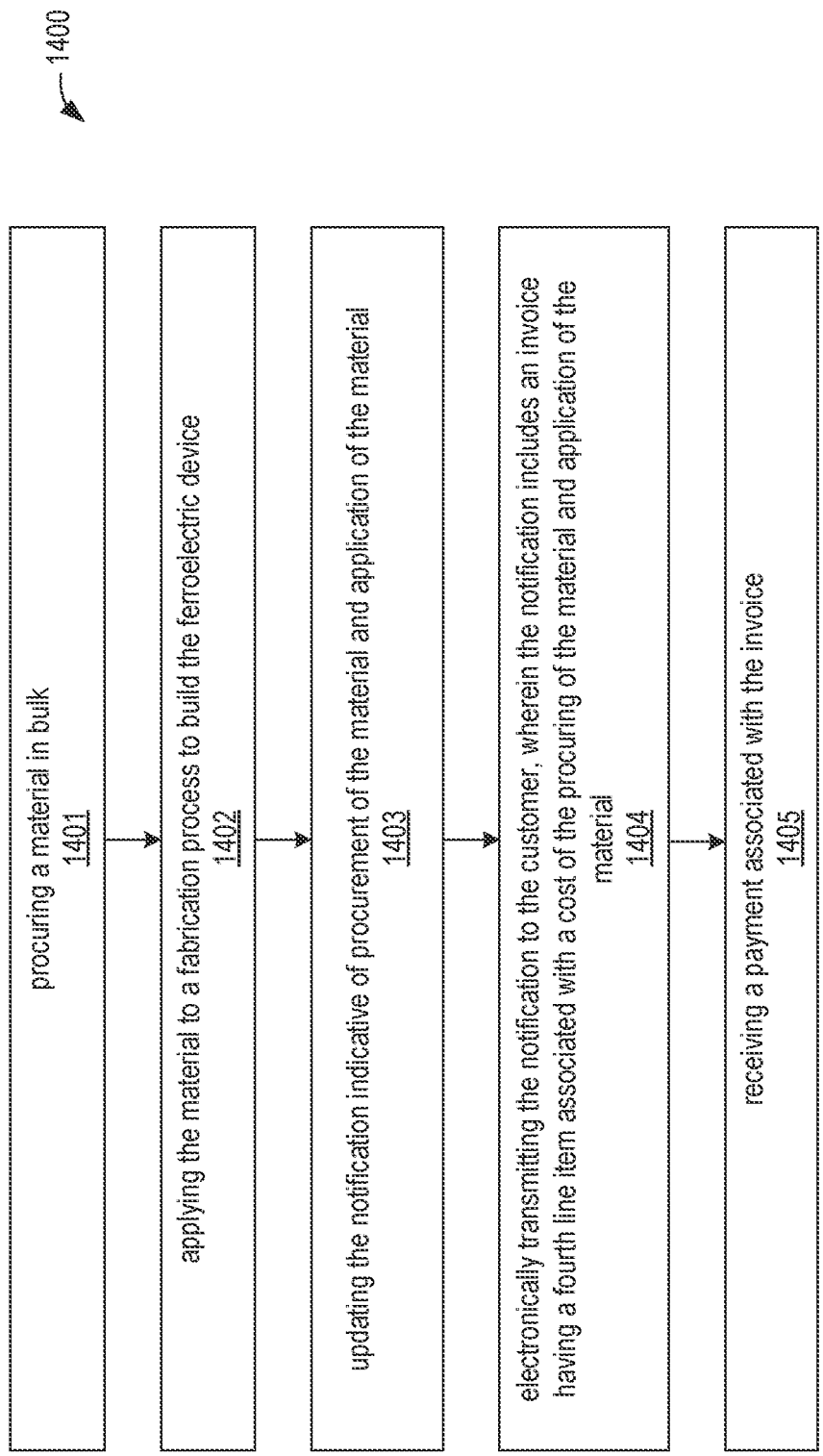
FIG. 14 illustrates a flowchart of iterative monetizing of a material as it is used for development of a device, in accordance with at least one embodiment.

FIG. 14 illustrates flowchart 1400 of iterative monetizing of a material as it is used for development of a device, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1401, a material may be procured. In at least one embodiment, material may be procured based on a model driven selection which is based on charge, mass and magnetic moment, and/or mass of atomic constituents of material. In at least one embodiment, material may be procured by an expert (e.g., by intuition gained from training in a field). In at least one embodiment, material is bulk material. In at least one embodiment, material is selective material. In at least one embodiment, material comprises material discussed with reference to target material herein.

In at least one embodiment, at operation 1402, procured material is applied to a fabrication process to build a device (e.g., ferroelectric device, paraelectric device, non-linear dielectric device, and/or magnetic tunnelling junction, etc.). In at least one embodiment, at operation 1403, a notification may be generated or updated indicative of procurement of material and application of target material. In at least one embodiment, at operation 1404, notification is electronically transmitted to a customer. In at least one embodiment, electronic transmission may be in a form of an email, facsimile, or a digital image. In at least one embodiment, notification may include an invoice having a line item (e.g., a first line item) associated with a cost of procuring of material and application of material. In at least one embodiment, invoice is one of: a bill of sale, an estimate cost, royalty, equity share, or cost-plus estimate. In at least one embodiment, at operation 1405, notification is updated after completing an iteration of procurement of material and application of material. In at least one embodiment, payment associated with invoice is received. In at least one embodiment, payment may be received in any form. In at least one embodiment, payment may be received electronically, as cash, as a credit, as a credit card, as a bitcoin or any other cryptocurrency.

Figure 15:
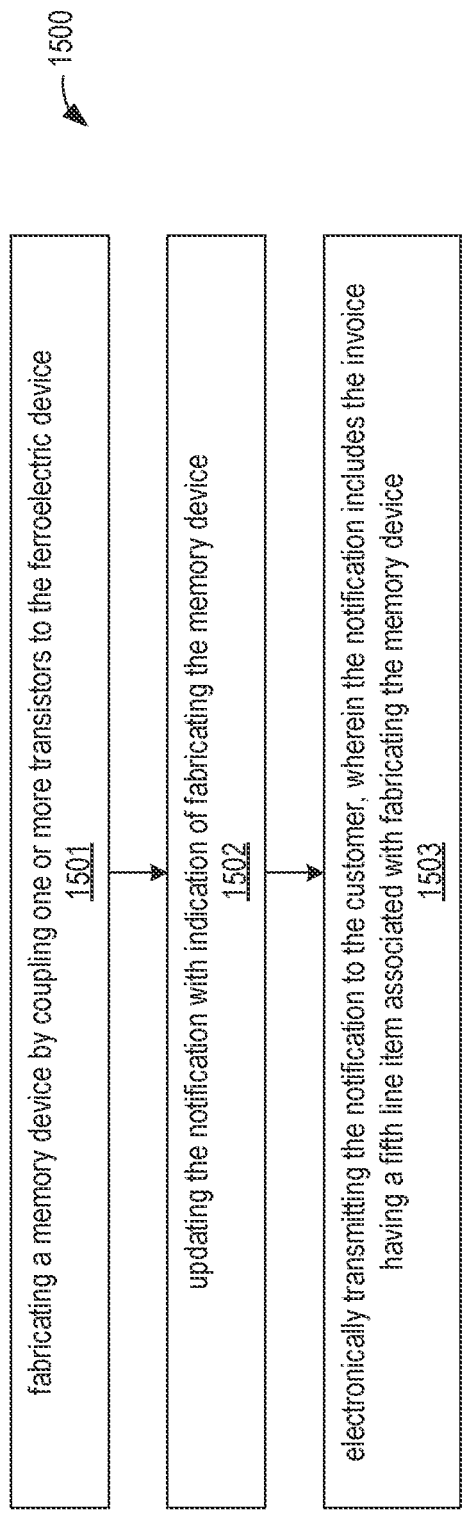
FIG. 15 illustrates a flowchart of iterative monetizing of a fabricating a memory device as it is integrated with one or more active devices, in accordance with at least one embodiment.

FIG. 15 illustrates flowchart 1500 of iterative monetizing of a fabricating a memory device as it is integrated with one or more active devices, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1501, a memory device is fabricated by coupling one or more transistors to a device (e.g., ferroelectric device, paraelectric device, non-linear dielectric device, magnetic tunneling junction, etc.). In at least one embodiment, at operation 1502, a notification is generated or updated with indication of fabricating memory device. In at least one embodiment, at operation 1503, notification is electronically transmitted to a customer. In at least one embodiment, notification includes invoice having a line item (e.g., fifth line item) associated with fabricating memory device.

Figure 16:
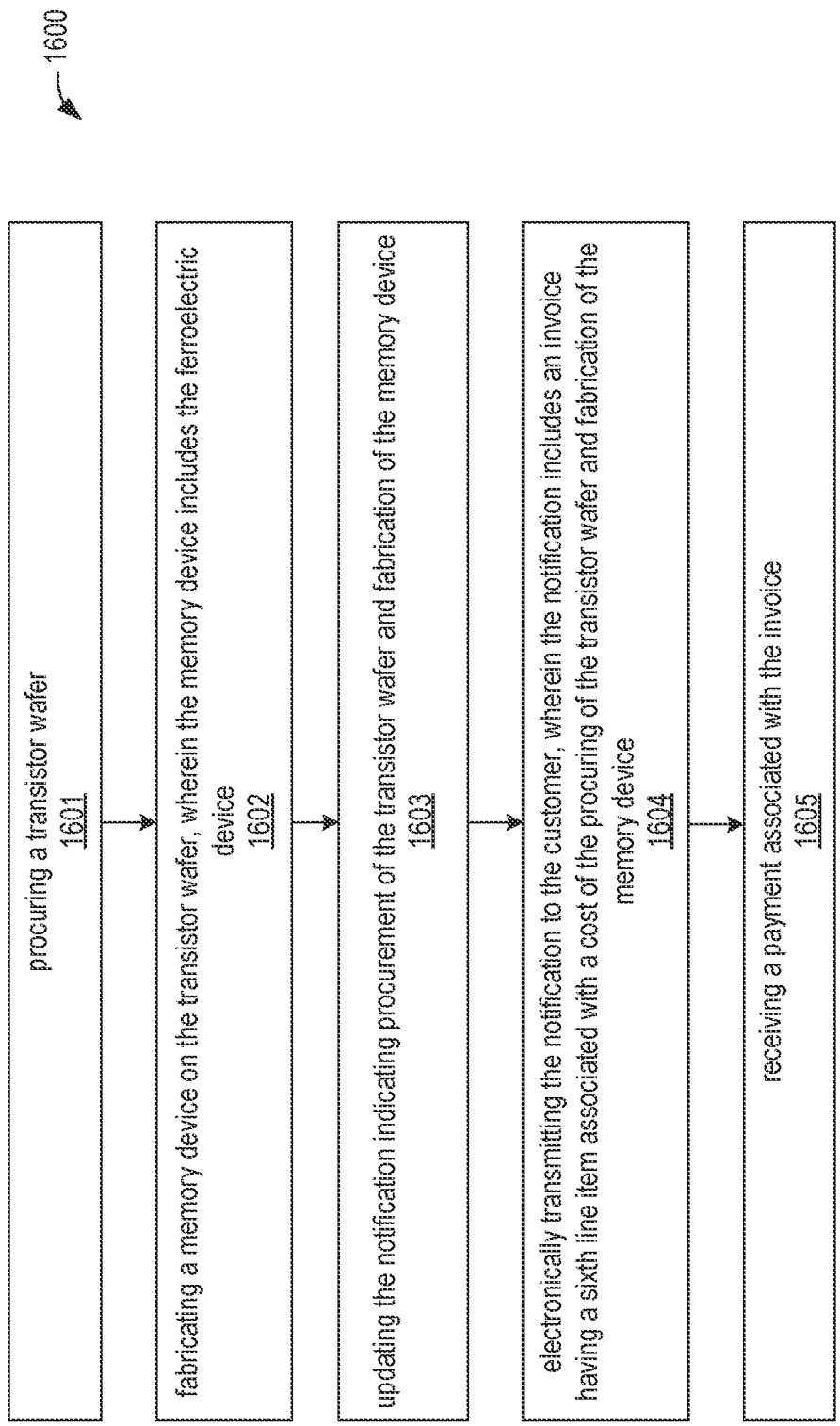
FIG. 16 illustrates a flowchart of iterative monetizing of a transistor wafer as it is used for development of a memory device, in accordance with at least one embodiment.

FIG. 16 illustrates flowchart 1600 of iterative monetizing of a transistor wafer as it is used for development of a memory device, in accordance with at least one embodiment. While various operations are shown in a particular order, order of operation can be modified. For example, some operations can be performed before others in a different iteration. Some operations blocks described herein can be performed by hardware, software, manually, or a combination of them.

In at least one embodiment, at operation 1601, a transistor wafer is procured. In at least one embodiment, transistor wafer includes front-end-of-line (FEOL) transistors. In at least one embodiment, transistor wafer includes back-end-of-line (BEOL) transistors. In at least one embodiment, at operation 1602, a memory device is fabricated on transistor wafer, wherein memory device includes a device (e.g., ferroelectric device, paraelectric device, non-linear dielectric). In at least one embodiment, at operation 1603, a notification is generated or updated indicating procurement of transistor wafer and fabrication of memory device. In at least one embodiment, at operation 1604, notification is electronically transmitted to customer, wherein notification includes an invoice having a line item associated with a cost of procuring of transistor wafer and fabrication of memory device. In at least one embodiment, at operation 1605, a payment associated with invoice is received. In at least one embodiment, payment can be received according to any suitable means as discussed herein.

FIG. 17 illustrates flowchart 1700 of iterative monetizing of a measuring electrical and/or chemical characteristics of a memory device, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1701, electrical and/or chemical characteristics of memory device and/or device (e.g., ferroelectric device, paraelectric device, non-linear dielectric device, magnetic tunneling junction, etc.) are measured. In at least one embodiment, at operation 1702, a notification is generated or updated, where notification is indicative of measuring electrical and/or chemical characteristics. In at least one embodiment, at operation 1703, notification is electronically transferred to customer. In at least one embodiment, notification includes an invoice having a line item (e.g., seventh line item) associated with measuring electrical and/or chemical characteristics. In at least one embodiment, at operation 1704, a payment associated with invoice is received.

FIG. 18 illustrates flowchart 1800 of iterative monetizing of multi-project wafers as they are used for development of a device, in accordance with at least one embodiment. While various operations are shown in a particular order, order of operations can be modified. For example, some operations can be performed before others in a different iteration. Some operations blocks described herein can be performed by hardware, software, manually, or a combination of them.

In at least one embodiment, at operation 1801, multi-project wafers are procured. In at least one embodiment, at operation 1802, materials on multi-project wafers are integrated. In at least one embodiment, these materials can be target materials discussed herein or bulk or selective materials discussed herein. In at least one embodiment, at operation 1803, a notification is generated or updated, where notification indicates procurement of multi-project wafers and integration of materials. In at least one embodiment, at operation 1804, notification is electronically transmitted to a customer. In at least one embodiment, notification includes an invoice having a line item associated with a cost of procuring of multi-project wafers and integration of materials. In at least one embodiment, at operation 1805, notification is electronically transmitted to a customer. In at least one embodiment, notification includes an invoice having a line item associated with a cost of procuring of production wafer and integration of materials. In at least one embodiment, at operation 1805, a payment associated with invoice is received.

In at least one embodiment, a method is provided which comprises procuring a production wafer. In at least one embodiment, method further comprises integrating materials on production wafer. In at least one embodiment, method further comprises generating a notification indicative of procurement of production wafer and integration of materials. In at least one embodiment, method further comprises electronically transmitting notification to a customer. In at least one embodiment, notification includes an invoice having a line item associated with a cost of procuring of production wafer and integration of materials. In at least one embodiment, method further comprises receiving a payment associated with invoice.

Here, term "device" may generally refer to an apparatus according to context of usage of that term. For example, a device may refer to a stack of layers or structures, a single structure or layer, a connection of various structures having active and/or passive elements, etc. Generally, a device is a three-dimensional structure with a plane along an x-y direction and a height along a z direction of an x-y-z Cartesian coordinate system. A plane of a device may also be plane of an apparatus, which comprises device.

Throughout specification, and in claims, term "connected" may generally refer to a direct connection, such as electrical, mechanical, or magnetic connection between things that are connected, without any intermediary devices.

Here, term "coupled" may generally refer to a direct or indirect connection, such as a direct electrical, mechanical, or magnetic connection between things that are connected or an indirect connection, through one or more passive or active intermediary devices.

Here, term "adjacent" here may generally refer to a position of a thing being next to (e.g., immediately next to or close to with one or more things between them) or adjoining another thing (e.g., abutting it).

Here, terms "circuit" or "module" may refer to one or more passive and/or active components that are arranged to cooperate with one another to provide a desired function.

Here, term "signal" may generally refer to at least one current signal, voltage signal, magnetic signal, or data/clock signal. Meaning of "a," "an," and "the" include plural references. Meaning of "in" includes "in" and "on."

Here, term "analog signal" may generally refer to any continuous signal for which time varying feature (variable) of signal is a representation of some other time varying quantity, e.g., analogous to another time varying signal.

Here, "digital signal" may generally refer to a physical signal that is a representation of a sequence of discrete values (a quantified discrete-time signal), for example of an arbitrary bit stream, or of a digitized (sampled and analog-to-digital converted) analog signal.

"Scaling" generally refers to converting a design (schematic and layout) from one process technology to another process technology and subsequently being reduced in layout area. Here, term "scaling" generally also refers to downsizing layout and devices within a same technology node. Here, term "scaling" may also refer to adjusting (e.g., slowing down or speeding up—i.e., scaling down, or scaling up respectively) of a signal frequency relative to another parameter, for example, power supply level.

Here, terms "substantially," "close," "approximately," "near," and "about," generally refer to being within +/−10% of a target value. For example, unless otherwise specified in an explicit context of their use, terms "substantially equal," "about equal" and "approximately equal" mean that there is no more than incidental variation between among things so described. Here, such variation is typically no more than +/−10% of a predetermined target value.

Unless otherwise specified use of ordinal adjectives "first," "second," and "third," etc., to describe a common object, merely indicate that different instances of like objects are being referred to and are not intended to imply that objects so described must be in a given sequence, either temporally, spatially, in ranking or in any other manner.

Here, phrases "A and/or B" and "A or B" mean (A), (B), or (A and B). Here, phrase "A, B, and/or C" means (A), (B), (C), (A and B), (A and C), (B and C), or (A, B and C).

Here, terms "left," "right," "front," "back," "top," "bottom," "over," "under," etc., if any, are used for descriptive purposes and not necessarily for describing permanent relative positions. For example, terms "over," "under," "front side," "back side," "top," "bottom," "over," "under," and "on" as used herein refer to a relative position of one component, structure, or material with respect to other referenced components, structures or materials within a device, where such physical relationships are noteworthy. These terms are employed herein for descriptive purposes only and predominantly within context of a device z-axis and therefore may be relative to an orientation of a device. Hence, a first material "over" a second material in context of a figure provided herein may also be "under" second material if device is oriented upside-down relative to context of figure provided. In context of materials, one material disposed over or under another may be directly in contact or may have one or more intervening materials. Moreover, one material disposed between two materials may be directly in contact with two layers or may have one or more intervening layers. In contrast, a first material "on" a second material is in direct contact with that second material. Similar distinctions are to be made in context of component assemblies.

Here, term "between" may be employed in context of a z-axis, x-axis or y-axis of a device. A material that is between two other materials may be in contact with one or both of those materials, or it may be separated from both of other two materials by one or more intervening materials. A material "between" two other materials may therefore be in contact with either of other two materials, or it may be coupled to other two materials through an intervening material. A device that is between two other devices may be directly connected to one or both of those devices, or it may be separated from both of other two devices by one or more intervening devices.

Here, multiple non-silicon semiconductor material layers may be stacked within a fin structure. In at least one embodiment, multiple non-silicon semiconductor material layers may include one or more "P-type" layers that are suitable (e.g., offer higher hole mobility than silicon) for P-type transistors. In at least one embodiment, multiple non-silicon semiconductor material layers may further include one or more "N-type" layers that are suitable (e.g., offer higher electron mobility than silicon) for N-type transistors. In at least one embodiment, multiple non-silicon semiconductor material layers may further include one or more intervening layers separating N-type from P-type layers. In at least one embodiment, intervening layers may be at least partially sacrificial, for example to allow one or more of a gate, source, or drain to wrap completely around a channel region of one or more of N-type and P-type transistors. In at least one embodiment, multiple non-silicon semiconductor material layers may be fabricated, at least in part, with self-aligned techniques such that a stacked CMOS device may include both a high-mobility N-type and P-type transistor with a footprint of a single FET (field effect transistor).

Here, "backend" generally refers to a section of a die which is opposite of a "frontend" and where an IC (integrated circuit) package couples to IC die bumps. In at least one embodiment, high-level metal layers (e.g., metal layer 6 and above in a ten-metal stack die) and corresponding vias that are closer to a die package are considered part of backend of die. In at least one embodiment, "frontend" generally refers to a section of die that includes active region (e.g., where transistors are fabricated) and low-level metal layers and corresponding vias that are closer to an active region (e.g., metal layer 5 and below in ten-metal stack die example).

In at least one embodiment, material described herein is illustrated by way of example and not by way of limitation in accompanying figures. In at least one embodiment, for simplicity and clarity of illustration, elements illustrated in figures are not necessarily drawn to scale. In at least one embodiment, dimensions of some elements may be exaggerated relative to other elements for clarity. In at least one embodiment, various physical features may be represented in their simplified "ideal" forms and geometries for clarity of discussion, but it is nevertheless to be understood that practical implementations may approximate illustrated ideals. In at least one embodiment, smooth surfaces and square intersections may be drawn in disregard of finite roughness, corner-rounding, and imperfect angular intersections characteristic of structures formed by nanofabrication techniques. In at least one embodiment, where considered appropriate, reference labels have been repeated among figures to indicate corresponding or analogous elements.

Reference in specification to "an embodiment," "one embodiment," "some embodiments," or "other embodiments," "at least one embodiment," generally means that a particular feature, structure, or characteristic described in connection with an embodiment may include in at least one embodiment, but not necessarily all embodiments. Various appearances of "an embodiment," "one embodiment," "at least one embodiment," or "some embodiments" are not necessarily all referring to same embodiments. A component, feature, structure, or characteristic "may," "might," or "could" be included, that component, feature, structure, or characteristic is not required to be included. If specification or claim refers to "a" or "an" element, that does not mean there is only one element. If specification or claims refer to "an additional" element, that does not preclude there being more than one of additional elements.

Furthermore, features, structures, functions, or characteristics may be combined in any suitable manner in at least one embodiment. For example, a first embodiment may be combined with a second embodiment anywhere particular features, structures, functions, or characteristics associated with two embodiments are not mutually exclusive.

While disclosure has been described in conjunction with at least one embodiment, many alternatives, modifications and variations of such at least one embodiment will be apparent to those of ordinary skill in art considering foregoing description. At least one embodiment is intended to embrace all such alternatives, modifications, and variations as to fall within broad scope of appended claims.

In addition, well-known power/ground connections to integrated circuit (IC) chips and other components may or may not be shown within presented figures, for simplicity of illustration and discussion, and so as not to obscure disclosure. Further, arrangements may be shown in block diagram form to avoid obscuring at least one embodiment, and also considering that specifics with respect to implementation of such block diagram arrangements are highly dependent upon platform within which at least one embodiment is to be implemented (e.g., such specifics should be well within purview of one skilled in art). Where specific details (e.g., circuits) are set forth to describe at least one embodiment, it should be apparent to one skilled in art that such disclosure can be practiced without, or with variation of, these specific details. At least one embodiment is thus to be regarded as illustrative instead of limiting.

Structures of at least of embodiment described herein can also be described as method(s) of forming those structures or apparatuses, and method(s) of operation of these structures or apparatuses. In at least one embodiment, methods can be performed by hardware, software, or a combination of them. In at least one embodiment, one or more machine-readable storage media (e.g., memory) is provided which stores one or more machine-executable instructions. In at least one embodiment, when one or more machine-executable instructions are executed by a machine (e.g., one or more processors), one or more methods described herein are performed. In at least one embodiment, machine-readable storage media is a tangible non-transitory machine-readable media. In at least one embodiment, machine-readable storage media comprises one of volatile or non-volatile memory, or a combination of them.

Following examples are provided that illustrate at least one embodiment. Examples can be combined with other examples. As such, at least one embodiment can be combined with at least one other embodiment without changing scope of at least one embodiment.

Example 1: A method for monetizing non-linear polar material process development, the method comprising: procuring a target material; applying the target material to a fabrication process to build a device with non-linear polar material; generating a notification indicative of procurement of the target material and application of the target material; and electronically transmitting the notification to a customer, wherein the notification includes an invoice having a first line item associated with a cost of procuring of the target material and the application of the target material.

Example 2: Method of example 1, wherein procuring the target material is based on a model driven selection which is based on charge, a mass and magnetic moment, and/or mass of atomic constituents of the target material.

Example 3: Method of example 1, wherein procuring the target material is based on an expertise of a person.

Example 4: Method of example 1 further comprising updating the notification after completing an iteration of procurement of the target material and application of the target material.

Example 5: Method of example 1, wherein the invoice is one of: a bill of sale, an estimate cost, royalty, equity share, or cost-plus estimate.

Example 6: Method of example 1, wherein the target material comprises one or combination of Physical Vapor Deposition (PVD) target material, ALD target material, or CVD target material.

Example 7: Method of example 1, wherein the target material is one of: a perovskite material which includes one of: $BaTiO_3$, $PbTiO_3$, $KNbO_3$, or $NaTaO_3$; Bismuth ferrite (BFO); Barium titanate (BTO); BFO doped with one of: Sc, Ti, V, Cr, Mn, Fe, Co, Ni, Cu, or Zn; BTO doped with one of: Sc, Ti, V, Cr, Mn, Fe, Co, Ni, Cu, or Zn; LBFO doped with Mn; lead zirconium titanate (PZT), or PZT with a doping material, wherein the doping material is one of La, Nb, Mc, Sc, or a 5d series element; bismuth ferrite (BFO) with a doping material, wherein the doping material is one of lanthanum, elements from lanthanide series of a periodic table, or elements of a 3d, 4d, 5d, 6d, 4f and 5f series of the periodic table; a relaxor ferroelectric material which includes one of lead magnesium niobate (PMN), lead magnesium niobate-lead titanate (PMN-PT), lead lanthanum zirconate titanate (PLZT), lead scandium niobate (PSN), barium titanium-bismuth zinc niobium tantalum (BT-BZNT), or Barium titanium-barium strontium titanium (BT-BST); hexagonal ferroelectric which includes one of: $YMnO_3$ or $LuFeO_3$; hexagonal ferroelectrics of a type h-$RMnO_3$, wherein R is a rare earth element which includes one of: cerium (Ce), dysprosium (Dy), erbium (Er), europium (Eu), gadolinium (Gd), holmium (Ho), lanthanum (La), lutetium (Lu), neodymium (Nd), prascodymium ($P_r$), promethium (Pm), samarium (Sm), scandium (Sc), terbium (Tb), thulium (Tm), ytterbium (Yb), or yttrium (Y); hafnium (Hf), zirconium (Zr), aluminum (Al), silicon (Si), their oxides or their alloyed oxides; Hafnium oxides as $Hf1-x \, Ex \, O_y$, where E can be Al, Ca, Ce, Dy, Er, Gd, Ge, La, Sc, Si, Sr, Sn, Zr, or Y; Al(1-x)Sc(x)N, Ga(1-x)Sc(x)N, Al(1-x)Y(x)N or Al(1-x-y)Mg(x)Nb(y)N, Ey doped $HfO_2$, where x includes one of: Al, Ca, Ce, Dy, Er, Gd, Ge, La, Sc, Si, Sr, Sn, or Y, wherein 'x' or 'y' is a fraction; or niobate type compounds $LiNbO_3$, $LiTaO_3$, lithium iron tantalum oxyfluoride, barium strontium niobate, sodium barium niobate, or potassium strontium niobate; or an improper ferroelectric material which includes one of: [PTO/STO]n or [LAO/STO]n, wherein 'n' is between 1 and 100, or a paraelectric material that comprises $SrTiO_3$, $Ba_{(x)}Sr_{(y)}TiO_3$, $HfZrO_2$, Hf—Si—O, La-substituted $PbTiO_3$, or a PMN-PT based relaxor ferroelectrics.

Example 8: Method of example 1 further comprising: procuring precursor from a vendor; feeding the precursor to the fabrication process to build the device with the non-linear polar material; updating the notification indicative of procurement of a volume of the precursor and feeding of the precursor; and electronically transmitting the notification to the customer, wherein the notification includes the invoice having a second line item associated with a cost of the volume of the precursor and feeding of the precursor.

Example 9: Method of example 1, wherein the method further comprising: determining a number of lot turns associated with the fabrication process; for an individual lot turn, determining a base cost; computing a total cost as a sum of the base cost for the individual lot turn; updating the notification indicative of the number of lot turns and the total cost; and electronically transmitting the notification to the customer, wherein the notification includes the invoice having a third line item associated with the number of lot turns and the total cost.

Example 10: Method of example 9, wherein the individual lot turn indicates a wafer being processed by one or more machines, wherein the number of lot turns indicates a number of operations performed on the wafer by the one or more machines.

Example 11: Method of example 10, wherein the number of operations include: a first operation that results in a first change in structure of the device with the non-linear polar material; a second operation that results in a second change in composition of a second material of the device with the non-linear polar material; a third operation that results in a third change in granularity of a third material of the device with the non-linear polar material; a fourth operation that results in a fourth change crystalline orientation of a fourth material of the device with the non-linear polar material; and/or a fifth operation that results in a fifth change in thermodynamics of a fifth material of the device with the non-linear polar material.

Example 12: Method of example 1, further comprising: procuring a material in bulk; applying the material to a fabrication process to build the device with the non-linear polar material; updating the notification indicative of procurement of the material and application of the material; and electronically transmitting the notification to the customer, wherein the notification includes an invoice having a fourth line item associated with a cost of the procuring of the material and application of the material.

Example 13: Method of example 1, wherein procuring the target material comprises procuring the target material in bulk.

Example 14: Method of example 1 further comprising: fabricating a memory device by coupling one or more transistors to the device with the non-linear polar material; updating the notification with indication of fabricating the memory device; and electronically transmitting the notification to the customer, wherein the notification includes the invoice having a fifth line item associated with fabricating the memory device.

Example 15: Method of example 1 further comprising: procuring a transistor wafer; fabricating a memory device on the transistor wafer, wherein the memory device includes the device with the non-linear polar material; updating the notification indicating procurement of the transistor wafer and fabrication of the memory device; and electronically transmitting the notification to the customer, wherein the notification includes an invoice having a sixth line item associated with a cost of the procuring of the transistor wafer and fabrication of the memory device.

Example 16: Method of example 15, further comprising: measuring electrical and/or chemical characteristics of the memory device and/or the device with the non-linear polar material; updating the notification indicative of measuring electrical and/or chemical characteristics; and electronically transmitting the notification to the customer, wherein the notification includes the invoice having a seventh line item associated with measuring electrical and/or chemical characteristics.

Example 17: Method of example 1 further comprising: procuring multi-project wafers; integrating materials on the multi-project wafers; updating the notification indicating procurement of the multi-project wafers and integration of materials; and electronically transmitting the notification to the customer, wherein the notification includes an invoice having an eighth line item associated with a cost of the procuring of the multi-project wafers and integration of materials.

Example 18: Method of example 1 further comprising receiving a payment associated with the invoice.

Example 19: Method of example 1 further comprising: modeling electrical and/or chemical characteristics of the target material to generate a representative model of the target material; generating a notification indicative of the representative model; and electronically transmitting the notification to a customer, wherein the notification includes an invoice having a line item associated with a cost of modeling the electrical and/or chemical characteristics.

Example 20: A method for monetizing a process development, the method comprising: procuring a production wafer; integrating materials on the production wafer; generating a notification indicative of procurement of the production wafer and integration of materials; and electronically transmitting the notification to a customer, wherein the notification includes an invoice having a line item associated with a cost of procuring of the production wafer and the integration of materials.

Example 21: Method of example 20 further comprising receiving a payment associated with the invoice.

Example 22: A method for monetizing a process development, the method comprising: determining a number of lot turns associated with a fabrication process; for an individual lot turn, determining a base cost; computing a total cost as a sum of the base cost for the individual lot turn; updating a notification indicative of the number of lot turns and the total cost; and electronically transmitting the notification to a customer, wherein the notification includes an invoice having a line item associated with the number of lot turns and the total cost.

Example 23: Method of example 22, wherein the individual lot turn indicates a wafer being processed by one or more machines, wherein the number of lot turns indicates a number of operations performed on the wafer by the one or more machines.

An abstract is provided that will allow a reader to ascertain nature and gist of at least one embodiment. An abstract is submitted with an understanding that it will not be used to limit scope or meaning of claims. Following claims are hereby incorporated into detailed description, with each claim standing on its own as a separate embodiment.

We claim:

1. A method for monetizing non-linear polar material process development, the method comprising:
   procuring a precursor from a vendor;
   feeding the precursor to a fabrication process to build a device with non-linear polar material;
   updating a notification indicative of procurement of a volume of the precursor and feeding of the precursor; and
   electronically transmitting the notification to a customer, wherein the notification includes an invoice having a first line item associated with a cost of the volume of the precursor and feeding of the precursor.

2. The method of claim 1, wherein the precursor includes one or more of: trimethysilane (3MS) gas, tetramethylsilane (4MS), hexachlorodisilane (HCDS), tetraethylorthosilicate, tris(dimethylamino)silane, tris(trimethylgermyl)arsine, tetrakisdimethylamidotitanium, chemicals from group III/V and II/VI, trimethylgallium, triethylgallium, trimethylindium, trimethylaluminum, tertiarybutylarsine, tertiarybutylphosphine, dimethylhydrazine, tetrabromomethane, diethyltelluride, two-dimensional (2D), molybdenumhexacarbonyl ($Mo(CO)_6$), tungstenhexacarbonyl ($W(CO)_6$), diisopropylselenide (DiPSe), bistert-butyliminobisdimethylaminowolframvi (BTMW), bis(tert-butylimido)bis(dimethylamido)molybdenum (BTMMo), diethyltelluride (DETe), methylallyltelluride (MATe), tris(cyclopentadienyl)scandium ($Cp_3Sc$) and/or trimethylmethylcyclopentadienylplatinumiv ($MeCpPtMe_3$).

3. The method of claim 1 further comprising:
   updating the notification and generating an updated notification after completing an iteration of procurement of the precursor and feeding of the precursor; and
   electronically transmitting the updated notification to the customer to provide in-process invoicing of the fabrication process to build the device with the non-linear polar material, wherein the in-process invoicing comprising the invoice provides cost-aware visibility to the fabrication process.

4. The method of claim 1, wherein the invoice is one of: a bill of sale, an estimate cost, royalty, equity share, or cost-plus estimate.

5. The method of claim 1, wherein the non-linear polar material is one of:

a perovskite material which includes one of: $BaTiO_3$, $PbTiO_3$, $KNbO_3$, or $NaTaO_3$;

bismuth ferrite (BFO);

barium titanate (BTO);

BFO doped with one of: Sc, Ti, V, Cr, Mn, Fe, Co, Ni, Cu, or Zn;

BTO doped with one of: Sc, Ti, V, Cr, Mn, Fe, Co, Ni, Cu, or Zn;

LBFO doped with Mn;

lead zirconium titanate (PZT) or PZT with a first doping material, wherein the first doping material is one of La, Nb, Mn, or 5d series elements;

bismuth ferrite (BFO) with a second doping material, wherein the second doping material is one of lanthanum, elements from lanthanide series of a periodic table, or elements of a 3d, 4d, 5d, 6d, 4f, and 5f series of the periodic table;

a relaxor ferroelectric material which includes one of: lead magnesium niobate (PMN), lead magnesium niobate-lead titanate (PMN-PT), lead lanthanum zirconate titanate (PLZT), lead scandium niobate (PSN), barium titanium-bismuth zinc niobium tantalum (BT-BZNT), or barium titanium-barium strontium titanium (BT-BST);

a first hexagonal ferroelectric which includes one of: $YMnO_3$ or $LuFeO_3$;

a second hexagonal ferroelectric of a type h-$RMnO_3$, wherein R is a rare earth element which includes one of: cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), or yttrium (Y); hafnium (Hf), zirconium (Zr), aluminum (Al), silicon (Si), their oxides or their alloyed oxides;

hafnium oxides as $Hf_{(1-x)}E_xO_y$, where E is one of Al, Ca, Ce, Dy, Er, Gd, Ge, La, Sc, Si, Sr, Sn, Zr, or Y, where x and y first and second fractions, respectively;

$Al_{(1-x)}Sc_{(x)}N$, $Ga_{(1-x)}Sc_{(x)}N$, $A_{(1-x)}Y_{(x)}N$ or $Al_{(1-x-y)}Mg_{(x)}Nb_{(y)}N$, where x and y are third and fourth fractions, respectively;

y doped $HfO_2$, where y includes one of: Al, Ca, Ce, Dy, Er, Gd, Ge, La, Sc, Si, Sr, Sn, or Y; or niobate type compounds $LiNbO_3$, $LiTaO_3$, lithium iron tantalum oxyfluoride, barium strontium niobate, sodium barium niobate, or potassium strontium niobate; or an improper ferroelectric material which includes one of: [PTO/STO]n or [LAO/STO]n, wherein 'n' is between 1 and 100, or a paraelectric material that comprises $SrTiO_3$, $Ba(x)Sr(y)TiO_3$, $HfZrO_2$, Hf—Si—O, La-substituted $PbTiO_3$, or a PMN-PT based relaxor ferroelectrics; or a paraelectric material that comprises $SrTiO_3$, $Ba(x)Sr(y)TiO_3$, $HfZrO_2$, Hf—Si—O, or a PMN-PT based relaxor ferroelectrics.

6. The method of claim 1, wherein the method further comprises:
determining a number of lot turns associated with the fabrication process;
for an individual lot turn, determining a base cost;
computing a total cost as a sum of the base cost for the individual lot turn;
updating the notification indicative of the number of lot turns and the total cost; and
electronically transmitting the notification to the customer, wherein the notification includes the invoice having a second line item associated with the number of lot turns and the total cost.

7. The method of claim 6, wherein the individual lot turn indicates a wafer being processed by one or more machines, and wherein the number of lot turns indicates a number of operations performed on the wafer by the one or more machines.

8. The method of claim 7, wherein the number of operations include:
a first operation that results in a first change in structure of the device with the non-linear polar material;
a second operation that results in a second change in composition of a second material of the device with the non-linear polar material;
a third operation that results in a third change in granularity of a third material of the device with the non-linear polar material;
a fourth operation that results in a fourth change crystalline orientation of a fourth material of the device with the non-linear polar material; and/or
a fifth operation that results in a fifth change in thermodynamics of a fifth material of the device with the non-linear polar material.

9. An apparatus for monetizing non-linear polar material process development, the apparatus comprising:
means for procuring a precursor from a vendor;
means for feeding the precursor to a fabrication process to build a device with non-linear polar material;
means for updating a notification indicative of procurement of a volume of the precursor and feeding of the precursor; and
means for electronically transmitting the notification to a customer, wherein the notification includes an invoice having a first line item associated with a cost of the volume of the precursor and feeding of the precursor.

10. The apparatus of claim 9, wherein the precursor includes one or more of: trimethysilane (3MS) gas, tetramethylsilane (4MS), hexachlorodisilane (HCDS), tetraethylorthosilicate, tris(dimethylamino)silane, tris(trimethylgermyl)arsine, tetrakisdimethylamidotitanium, chemicals from group III/V and II/VI, trimethylgallium, triethylgallium, trimethylindium, trimethylaluminum, tertiarybutylarsine, tertiarybutylphosphine, dimethylhydrazine, tetrabromomethane, diethyltelluride, two-dimensional (2D), molybdenumhexacarbonyl ($Mo(CO)_6$), tungstenhexacarbonyl ($W(CO)_6$), diisopropylselenide (DiPSe), bistert-butyliminobisdimethylaminowolframvi (BTMW), Bis(tert-butylimido)bis(dimethylamido)molybdenum (BTMMo), diethyltelluride (DETe), methylallyltelluride (MATe), tris(cyclopentadienyl)scandium ($Cp_3Sc$) and/or trimethylmethylcyclopentadienylplatinumiv ($MeCpPtMe_3$).

11. The apparatus of claim 9 further comprising:
means for updating the notification and generating an updated notification after completing an iteration of procurement of the precursor and feeding of the precursor; and
means for electronically transmitting the updated notification to the customer to provide in-process invoicing of the fabrication process to build the device with the non-linear polar material, wherein the in-process invoicing comprising the invoice provides cost-aware visibility to the fabrication process.

12. The apparatus of claim 9, wherein the invoice is one of: a bill of sale, an estimate cost, royalty, equity share, or cost-plus estimate.

13. The apparatus of claim 9, wherein the non-linear polar material is one of:

a perovskite material which includes one of: BaTiO$_3$, PbTiO$_3$, KNbO$_3$, or NaTaO$_3$;

bismuth ferrite (BFO);

barium titanate (BTO);

BFO doped with one of: Sc, Ti, V, Cr, Mn, Fe, Co, Ni, Cu, or Zn;

BTO doped with one of: Sc, Ti, V, Cr, Mn, Fe, Co, Ni, Cu, or Zn;

LBFO doped with Mn;

lead zirconium titanate (PZT) or PZT with a first doping material, wherein the first doping material is one of La, Nb, Mn, or 5d series elements;

bismuth ferrite (BFO) with a second doping material, wherein the second doping material is one of lanthanum, elements from lanthanide series of a periodic table, or elements of a 3d, 4d, 5d, 6d, 4f, and 5f series of the periodic table;

a relaxor ferroelectric material which includes one of: lead magnesium niobate (PMN), lead magnesium niobate-lead titanate (PMN-PT), lead lanthanum zirconate titanate (PLZT), lead scandium niobate (PSN), barium titanium-bismuth zinc niobium tantalum (BT-BZNT), or barium titanium-barium strontium titanium (BT-BST);

a first hexagonal ferroelectric which includes one of: YMnO$_3$ or LuFeO$_3$;

a second hexagonal ferroelectric of a type h-RMnO$_3$, wherein R is a rare earth element which includes one of: cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), or yttrium (Y); hafnium (Hf), zirconium (Zr), aluminum (Al), silicon (Si), their oxides or their alloyed oxides;

Hafnium oxides as Hf$_{(1-x)}$E$_x$O$_y$, where E is one of Al, Ca, Ce, Dy, Er, Gd, Ge, La, Sc, Si, Sr, Sn, Zr, or Y, wherein x and y are first and second fractions, respectively;

Al$_{(1-x)}$Sc$_{(x)}$N, Ga$_{(1-x)}$Sc$_{(x)}$N, Al$_{(1-x)}$Y$_{(x)}$N or Al$_{(1-x-y)}$Mg$_{(x)}$Nb$_{(y)}$N, wherein x and y are third and fourth fractions, respectively;

y doped HfO$_2$, where y includes one of: Al, Ca, Ce, Dy, Er, Gd, Ge, La, Sc, Si, Sr, Sn, or Y; or niobate type compounds LiNbO$_3$, LiTaO$_3$, lithium iron tantalum oxyfluoride, barium strontium niobate, sodium barium niobate, or potassium strontium niobate; or an improper ferroelectric material which includes one of: [PTO/STO]n or [LAO/STO]n, wherein 'n' is between 1 and 100, or a paraelectric material that comprises SrTiO$_3$, Ba$_{(x)}$Sr$_{(y)}$TiO$_3$, HfZrO$_2$, Hf—Si—O, La-substituted PbTiO$_3$, or a PMN-PT based relaxor ferroelectrics; or a paraelectric material that comprises SrTiO$_3$, Ba$_{(x)}$Sr$_{(y)}$TiO$_3$, HfZrO$_2$, Hf—Si—O, or a PMN-PT based relaxor ferroelectrics.

14. The apparatus of claim 9 further comprising:

means determining a number of lot turns associated with the fabrication process;

for an individual lot turn, means for determining a base cost;

means for computing a total cost as a sum of the base cost for the individual lot turn;

means for updating the notification indicative of the number of lot turns and the total cost; and means for electronically transmitting the notification to the customer, wherein the notification includes the invoice having a second line item associated with the number of lot turns and the total cost.

15. A method for monetizing non-linear polar material process development, the method comprising:

procuring a precursor;

feeding the precursor to a fabrication process to build a device with ferroelectric material;

updating a notification indicative of procurement of a volume of the precursor and feeding of the precursor; and electronically transmitting the notification to a customer, wherein the notification includes an invoice having a first line item associated with a cost of the volume of the precursor and feeding of the precursor.

16. The method of claim 15, wherein the precursor includes one or more of: trimethysilane (3MS) gas, tetramethylsilane (4MS), hexachlorodisilane (HCDS), tetraethylorthosilicate, tris(dimethylamino)silane, tris(trimethylgermyl)arsine, tetrakisdimethylamidotitanium, chemicals from group III/V and II/VI, trimethylgallium, triethylgallium, trimethylindium, trimethylaluminum, tertiarybutylarsine, tertiarybutylphosphine, dimethylhydrazine, tetrabromomethane, diethyltelluride, two-dimensional (2D), molybdenumhexacarbonyl (Mo(CO)$_6$), tungstenhexacarbonyl (W(CO)$_6$), diisopropylselenide (DiPSe), bistert-butyliminobisdimethylaminowolframvi (BTMW), bis(tert-butylimido) bis(dimethylamido)molybdenum (BTMMo), diethyltelluride (DETe), methylallyltelluride (MATe), tris (cyclopentadienyl)scandium (Cp3Sc) and/or trimethylmethylcyclopentadienylplatinumiv (MeCpPtMe3).

17. The method of claim 15 further comprising:

updating the notification and generating an updated notification after completing an iteration of procurement of the precursor and feeding of the precursor; and electronically transmitting the updated notification to the customer to provide in-process invoicing of the fabrication process to build the device with the ferroelectric material, wherein the in-process invoicing comprising the invoice provides cost-aware visibility to the fabrication process.

* * * * *